US011400106B2

(12) United States Patent
Brown et al.

(10) Patent No.: US 11,400,106 B2
(45) Date of Patent: *Aug. 2, 2022

(54) METHODS FOR INHIBITING MICROBE GROWTH

(71) Applicant: MCMASTER UNIVERSITY, Hamilton (CA)

(72) Inventors: Eric Brown, Oakville (CA); Maya Farha, Ancaster (CA); Craig MacNair, Ancaster (CA); Lindsey Carfrae, Mississauga (CA)

(73) Assignee: McMaster University, Hamilton (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/162,142

(22) Filed: Jan. 29, 2021

(65) Prior Publication Data

US 2021/0145854 A1  May 20, 2021

Related U.S. Application Data

(63) Continuation of application No. PCT/CA2019/051059, filed on Aug. 1, 2019.

(Continued)

(51) Int. Cl.
*A61K 31/7052* (2006.01)
*A61P 31/04* (2006.01)
(Continued)

(52) U.S. Cl.
CPC ........ *A61K 31/7052* (2013.01); *A61K 9/0014* (2013.01); *A61K 9/0048* (2013.01);
(Continued)

(58) Field of Classification Search
CPC ........ A01N 59/04; A01N 37/40; A01N 37/52; A01N 43/86; A61K 31/7052; A61K 33/00;
(Continued)

(56) References Cited

U.S. PATENT DOCUMENTS 4,328,245 A  5/1982  Yu et al.
4,409,239 A  10/1983  Yu
(Continued)

FOREIGN PATENT DOCUMENTS

CA  2159984  10/1994
CN  102283799 B  7/2013
(Continued)

OTHER PUBLICATIONS

Baba et al., "Construction of *Escherichia coli* K-12 in-frame, single-gene knockout mutants: the Keio collection," Mol Syst Biol 2, pp. 1-11 (2006).
(Continued)

*Primary Examiner* — Audrea B Coniglio
(74) *Attorney, Agent, or Firm* — Gowling WLG (Canada) LLP

(57) ABSTRACT

Provided herein are methods and compositions useful for inhibiting microbe growth. The methods can comprise contacting the microbe with an antimicrobial agent and bicarbonate. In some embodiments, provided herein are methods for treating or preventing a microbial infection, comprising administering to a subject in need an effective amount of (i) bicarbonate and (ii) an antimicrobial agent.

17 Claims, 41 Drawing Sheets

Related U.S. Application Data

(60) Provisional application No. 62/713,231, filed on Aug. 1, 2018.

(51) Int. Cl.

| | |
|---|---|
| *A61K 9/00* | (2006.01) |
| *A61K 33/00* | (2006.01) |
| *A61K 33/02* | (2006.01) |
| *A61K 33/10* | (2006.01) |
| *A61K 33/30* | (2006.01) |

(52) U.S. Cl.
CPC .............. *A61K 33/00* (2013.01); *A61K 33/02* (2013.01); *A61K 33/10* (2013.01); *A61K 33/30* (2013.01); *A61P 31/04* (2018.01)

(58) Field of Classification Search
CPC ........ A61K 33/02; A61K 33/10; A61K 33/30; A61K 9/0014; A61K 9/0048; A61P 31/04; A61P 31/10; A61P 31/12; A61P 33/00

See application file for complete search history.

(56) References Cited

U.S. PATENT DOCUMENTS

| | | | |
|---|---|---|---|
| 4,410,545 | A | 10/1983 | Yu et al. |
| 6,159,458 | A | 12/2000 | Bowman et al. |
| 6,239,113 | B1 | 5/2001 | Dawson et al. |
| 6,350,458 | B1 | 2/2002 | Modi |
| 6,569,443 | B1 | 5/2003 | Dawson et al. |
| 6,861,411 | B1 | 3/2005 | Ahmed |
| 6,984,403 | B2 | 1/2006 | Hagen et al. |
| 7,056,893 | B2 | 6/2006 | Roy et al. |
| 9,198,862 | B2 | 12/2015 | Pilgaonkar et al. |
| 10,940,163 | B2 | 3/2021 | Brown et al. |
| 2010/0273748 | A1 | 10/2010 | Gallo et al. |
| 2018/0243333 | A1 | 8/2018 | Brown et al. |

FOREIGN PATENT DOCUMENTS

| | | |
|---|---|---|
| CN | 104447918 A | 3/2015 |
| CN | 105010307 A | 11/2015 |
| WO | WO 2018/141063 A1 | 8/2018 |

OTHER PUBLICATIONS

Bakker and Mangerich, "Interconversion of components of the bacterial proton motive force by electrogenic potassium transport," J Bacteriol 1981, 147: 820-826 (1981).

Berge et al, "Pharmaceutical Salts," J. Pharm. Sci. 66(1):1-19 (1977).

Bowman et al., "Development of a Topical Polymeric Mucoadhesive Ocular Delivery System for Azithromycin," Journal of Ocular Pharm and Therapeutics 25(2):133-139 (2009).

Corral et al., "Antimicrobial Activity of Sodium Bicarbonate," Journal of Food Science 53(3):981-982 (1988).

Diver et al., "The accumulation of five quinolone antibacterial agents by *Escherichia coli*.," J Antimicrob Chemother 25:319-333 (1990).

Ejim et al., "Combinations of antibiotics and nonantibiotic drugs enhance antimicrobial efficacy," Nature chemical biology 7:348-350 (2011).

Ersoy et al., "Correcting a Fundamental Flaw in the Paradigm for Antimicrobial Susceptibility Testing," EBioMedicine 20:173-181 (2017).

Farha et al. "Bicarbonate Alters bacterial Susceptibility to Antibiotics by Targeting the Proton Motive Force," ACS Infectious Diseases, pp. A-I (2017).

Farha et al., "Collapsing the proton motive force to identify synergistic combinations against *Staphylococcus aureus*," Chemistry & biology 20:1168-1178 (2013).

French et al., "A robust platform for chemical genomics in bacterial systems," Mol Biol Cell 27:1015-1025 (2016).

Gutierrez-Huante et al., "Bicarbonate enhances the in-vitro antibiotic activity of kanamycin in *Escherichia coli*," Letters in Applied Microbiology 60:440-446 (2015).

Kaushik et al, "Tobramycin and Bicarbonate synergise to kill planktonic Psuedomonas aeruginosa, but antagonise to promote biofilm survival," NPJ Biotilms Microbiomes 2:16006 (2016), 21 pages.

Keseler et al., "EcoCyc: fusing model organism databases with systems biology," Nucleic Acids Res 41:D605-D612 (2013).

Ko et al., "Influence of Zinc, Sodium Bicarbonate, and Citric Acid on the Antibacterial Activity of Ovotransferrin Against *Escherichia coli* 0157:H7 and *Listeria monocytogenes* in Model Systems and Ham," Poultry Science 87:2660-2670 (2008).

Letscher-Bru et al., "Antifungal Activity of Sodium Bicarbonate against Fungal agent causing superficial infections," Mycopathologia 175:153-158 (2013).

Lobritz et al., Antibiotic efficacy is linked to bacterial cellular respiration. Proc Natl Acad Sci USA 112:8173-8180 (2015).

Mangat et al., "Rank ordering plate data facilitates data visualization and normalization in high-throughput screening," J Biomol Screen 19:1314-1320 (2014).

Martinez-Duncker, et al., "Bicarbonate has Varied Effect on the In Vitro Activity of Antibiotics in *Escherichia coli*," Interscience Conference on Antimicrobial Agents and Chemotherapy (ICAAC), San Diego, CA, Abstract C-616, 2 pages (Sep. 19, 2015).

Marvola et al., "Bioavailability of Erythromycin Acistrate from Hard Gelatin Capsules Containing Sodium Bicarbonate," Pharmaceutical Research 8(8):1056-1058 (1991).

Miyasaki et al., "Antimicrobial Properties of Hydrogen Peroxide and Sodium bicarbonate Individually and in Combination against Selected Oral, Gram-negative, Facultative Bacteria," J. Dent. Res. 65(9):1142-1148 (1986).

Mobley et al; "Erythromycin plus sodium bicarbonate in chronic bacterial prostatitis," Urology III(1):60-62 (1974).

Newbrun et al; "Bactericidal Action of Bica rbonate Ion on selected periodontal pathogenic microorganisms," J. Periodontol. 55(11):658-667 (1984).

Piddock et al., "Quinolone accumulation by *Pseudomonas aeruginosa*, *Staphylococcus aureus* and *Escherichia coli*," J Antimicrob Chemother 43:61-70 (1999).

Stokes, et al., "Cold Stress Makes *Escherichia coli* Susceptible to Glycopeptide Antibiotics by Altering Outer Membrane Integrity," Cell Chem. Biol. 23(2):267-277 (2016).

Thompson et al., "Antibacterial Activity of Lidocaine in Combination with a Bicarbonate Buffer," J. Dennatol. Surg. Onco. 19:216-220 (1993).

Zaslaver A. et al, "A comprehensive library of fluorescent transcriptional reporters for *Escherichia coli*," Nat Methods 3:623-628 (2006).

Zasloff, "Antimicrobial Peptides in Health and Disease," N Engl J Med 347: 1199-1200 (2002).

Zhang et al; "Bicarbonate induces high-level resistance to the human antimicrobial peptide LL-37 in *Staphylococcus aureus* small colony variants," Journal of Antimicrobial Chemotherapy 73:615-619 (2018) ( Published on Dec. 4, 2017).

Richter et al., "Predictive rules for compound accumulation yield a broad-spectrum antibiotic," Nature. May 18, 2017; 545(7654): 299-304.

Melissa Archer and Gary Oderda, "Otic Antibiotic-Corticosteroid Drug Class Review," University of Utah College of Pharmacy, University of Utah College of Pharmacy, Feb. 2013, 12 pages.

Prednisolone Ophthalmic Package Insert, Mar. 2014, 7 pages.

AzaSite (azithromycin ophthalmic solution) Prescribing Information, Jul. 2012, 12 pages.

Altabax (retapamulin ointment) prescribing information, Dec. 2012, 12 pages.

Altargo (retapamulin), Product Monograph, Aug. 2018, retrieved Jul. 10, 2019 at https://au.gsk.com/media/212995/altargo_cmi_au_002_approved.pdf, 3 pages.

(56) References Cited

OTHER PUBLICATIONS

Bacitracin Ointment, Updated Oct. 18, 2016, retrieved Jul. 11, 2019, at https://dailymed.nlm.nih.gov/dailymed/drugInfo.cfm?setid=024bc706-2da7-4e41-b1bc-60fa1b351463, 6 pages.
Bactroban Approved Package Insert, 5 pages, dated Dec. 6, 2013.
Besivance Prescribing Information, Apr. 2018, 2 pages.
Ciloxan, dated Nov. 2018, retrieved Jul. 11, 2019, at https://dailymed.nlm.nih.gov/dailymed/drugInfo.cfm?setid=1c292706-a900-4d6f-979e-9c42d6ff2fb2, 7 pages.
Cipro HC, Updated Nov. 14, 2018, retrieved Jul. 11, 2019, at https://dailymed.nlm.nih.gov/dailymed/drugInfo.cfm?setid=70b19501-34b6-4f95-a8dd-dd3e67d22399, 7 pages.
Ciprodex Prescribing Information, Feb. 2019, 13 pages.
Clindamycin 1%, Updated May 9, 2019, retrieved Jul. 11, 2019, at https://dailymed.nlm.nih.gov/dailymed/drugInfo.cfm?setid=887a3793-152c-6b7f-e053-2a95a90ab09b, 8 pages.
Cochereau et al., "3-day treatment with azithromycin 1.5% eye drops versus 7-day treatment with tobramycin 0.3% for purulent bacterial conjunctivitis: multicentre, randomised and controlled trial in adults and children," Br J. Ophthalmol 91:465-469 (2007).
Coly-mycin, dated Feb. 2016, retrieved Jul. 11, 2019, at https://dailymed.nlm.nih.gov/dailymed/drugInfo.cfm?setid=256f4083-5b34-4643-a75a-dd1a59a5d964, 9 pages.
Cortisporin TC Otic description, dated Jan. 15, 2019, retrieved Jul. 11, 2019, at https://dailymed.nlm.nih.gov/dailymed/drugInfo.cfm?setid=9c6fc1c7-3350-42ae-b999-aca48e704bb1, 9 pages.
Eryacne Package Leaflet: Information for the User, approved Sep. 2009, retrieved Jul. 11, 2019, at https://www.drugs.com/uk/eryacne-4-leaflet.html, 2 pages.
Erymed, retrieved Jul. 11, 2019, at https://www.ndrugs.com/?s=erymed%20plus&t=side%20effects, 4 pages.
Erythromycin, dated Jul. 2017, retrieved Jul. 11, 2019, at https://dailymed.nlm.nih.gov/dailymed/drugInfo.cfm?setid=b21d02ea-5394-4f88-8d2b-3a8cd6e807a0, 5 pages.
Floxin OTIC, dated Aug. 24, 2009, retrieved Jul. 11, 2019 at https://dailymed.nlm.nih.gov/dailymed/drugInfo.cfm?setid=b4968de4-3644-953a-d5d1-28f029cb4175, 13 pages.
Fusidic Acid Cream Package Leaflet, dated Jul. 2016, retrieved Jul. 10, 2019, at https://www.drugs.com/uk/fusidic-acid-20-mg-g-cream-leaflet.html, 2 pages.
Gatifloxacin, dated May 3, 2018, retrieved Jul. 11, 2019, at https://dailymed.nlm.nih.gov/dailymed/drugInfo.cfm?setid=14312de6-67d4-4de2-854c-ef764090dd83, A88, 9 pages.
Gentamicin, dated Sep. 26, 2013, retrieved Jul. 11, 2019 at https://dailymed.nlm.nih.gov/dailymed/drugInfo.cfm?setid=84f5c763-1cd3-4d85-9afb-934db8666fbf, 13 pages.
Gentamicin 0.3%—Eye drops, Patient Leaflet, Mar. 2014, retrieved Jul. 11, 2019, at https://www.medicines.org.uk/emc/files/pil.6552.pdf, one page.
Gentamicin Otic, 2019, retrieved Jul. 11, 2019, at https://www.drugs.com/cons/gentamicin-otic.html, 4 pages.
Kugelberg et al., "Establishment of a Superficial Skin Infection Model in Mice by Using *Staphylococcus aureus* and *Streptococcus pyogenes*," Antimicrobial Agents and Chemotherapy 49(8):3435-3441 (2005).
Marquardt,"Animal Models of Bacterial Keratitis," Hindawi Publishing Corporation, Journal of Biomedicine and Biotechnology, vol. 2011, Article ID 680642, 12 pages (2011).
Neosporin, dated Oct. 3, 2006, retrieved Jul. 11, 2019, at https://dailymed.nlm.nih.gov/dailymed/drugInfo.cfm?setid=7e971c99-1f3f-4a9f-5084-fbe5b9f1a9e1, 5 pages.
Neosporin (Bacitracin, Neomycin, and Polymyxin B, Pramoxine hcl), dated Jun. 8, 2017, retrieved Jul. 11, 2019, at https://dailymed.nlm.nih.gov/dailymed/drugInfo.cfm?setid=41c49d4f-201e-4aa9-b6a6-ea61edaf9530, 4 pages.

Ocuflox, dated Apr. 14, 2017, retrieved Jul. 11, 2019 at https://dailymed.nlm.nih.gov/dailymed/drugInfo.cfm?setid=7aab4449-3dda-4e2c-8e40-b3244a548bf5, 8 pages.
Okamycin webpages, dated 2017, retrieved Jul. 11, 2019, at http://www.instantremedies.net/okamycin-500, 3 pages.
Opitz and Harthan, "Review of Azithromycin Ophthalmic 1% solution (Azasite®) for the Treatment of Ocular Infections," Ophthalmology and Eye Diseases 4:1-14 (2012).
Otiprio Prescribing Information, dated Mar. 2018, retrieved Jul. 10, 2019, at https://otiprio.com/prescribing-information.pdf, 4 pages.
Otovel Prescribing Information, Apr. 2016, 20 pages.
Polymyxin B, dated Jun. 21, 2011, retrieved Jul. 11, 2019, at https://www.accessdata.fda.gov/drugsatfda_docs/label/2012/060716Orig1s020Lbl.pdf, 3 pages.
Polysporin, dated Dec. 1, 2016, retrieved Jul. 11, 2019, at https://dailymed.nlm.nih.gov/dailymed/drugInfo.cfm?setid=e0fcf83e-a374-4fc0-a629-873033054392, 4 pages.
Quixin Prescribing Information, dated Aug. 1, 2018, retrieved Jul. 11, 2019, at https://www.drugs.com/pro/quixin.html, 10 pages.
Sulfamethoxazole and Trimethoprim, dated Dec. 30, 2013, retrieved Jul. 11, 2019, at https://dailymed.nlm.nih.gov/dailymed/drugInfo.cfm?setid=804f8363-8ea1-4a57-bbd1-7fd9b6b4d29b, 16 pages.
TobraDex (tobramycin and dexamethas one ophthalmic suspension) sterile, May 2018, 4 pages.
Tobrex, dated Dec. 3, 2018, retrieved Jul. 11, 2019, at https://dailymed.nlm.nih.gov/dailymed/drugInfo.cfm?setid=cdd423c5-a231-47d4-bf51-00b5c29e6a60, 6 pages.
Vigamox Product Monograph including Patient Medication Information (Moxifloxacin Ophthalmic Solution), dated Dec. 1, 2017, 27 pages.
Zineryt Package Leaflet, dated, retrieved online Jul. 11, 2019, at https://www.medicines.org.uk/emc/files/pil.5488.pdf, 2 pages.
Ala-Quin webpage, dated Jun. 5, 2019, retrieved online Jul. 9, 2019 at https://www.drugs.com/mtm/ala-quin.html, 4 pages.
Mycolog II webpage, dated Dec. 3, 2018, retrieved online Jul. 9, 2019 at https://www.drugs.com/mtm/mycolog-ii-topical.html, 4 pages.
Xerese Cream webpage, dated Jun. 5, 2019, retrieved Jul. 9, 2019 at https://www.drugs.com/xerese.html, 4 pages.
Lotrisone webpage, dated Apr. 28, 2019, retrieved Jul. 9, 2019, at https://www.drugs.com/lotrisone.html, 4 pages.
Alcortin webpage, dated Jan. 14, 2019, retrieved Jul. 9, 2019, at https://www.drugs.com/mtm/alcortin-a-topical.html, 4 pages.
Cortisporin Cream webpage, dated Apr. 1, 2018, retrieved Jul. 9, 2019, at https://www.drugs.com/pro/cortisporin-cream.html, 8 pages.
Cortisporin Ointment webpage, dated Apr. 1, 2018, retrieved Jul. 9, 2019, at https://www.drugs.com/pro/cortisporin-ointment.html, 9 pages.
Dermazene webpage, dated May 7, 2019, retrieved Jul. 9, 2019, at https://www.drugs.com/cdi/dermazene.html, 4 pages.
Mytrex webpage, dated Dec. 3, 2018, retrieved Jul. 9, 2019, at https://www.drugs.com/mtm/mytrex-topical.html, 4 pages.
Neo-Synalar webpage, dated Nov. 16, 2018, retrieved Jul. 9, 2019, at https://www.drugs.com/mtm/neo-synalar.html, 4 pages.
Vytone webpage, dated May 7, 2019, retrieved Jul. 9, 2019 at https://www.drugs.com/cdi/vytone.html, 4 pages.
Xolegel CorePak webpage, dated Feb. 9, 2019, retrieved Jul. 9, 2019, at https://www.drugs.com/cdi/xolegel-corepak.html, 5 pages.
Promega, Buffers for Biochemical Reactions, copyright 2004-2012, pp. 15-1 to 15-5 (Year: 2012).
Dorschner et al., "The Mammalian Ionic Environment Dictates Microbial Susceptibility to Antimicrobial Defense Peptides," The FASEB Journal, vol. 20, 8 pages (2006).
Ersoy et al., Bicarbonate Resensitization of Methicillin-Resistant *Staphylococcus aureus* to -Lactam Antibiotics, Antimicrob. Ag. Chemother., 24 63(7):E00496-19, pp. 1-16 (2019).
Sigma Life Science (Cell Culture Manual, 2011-2014, pp. 1-380) (2014).

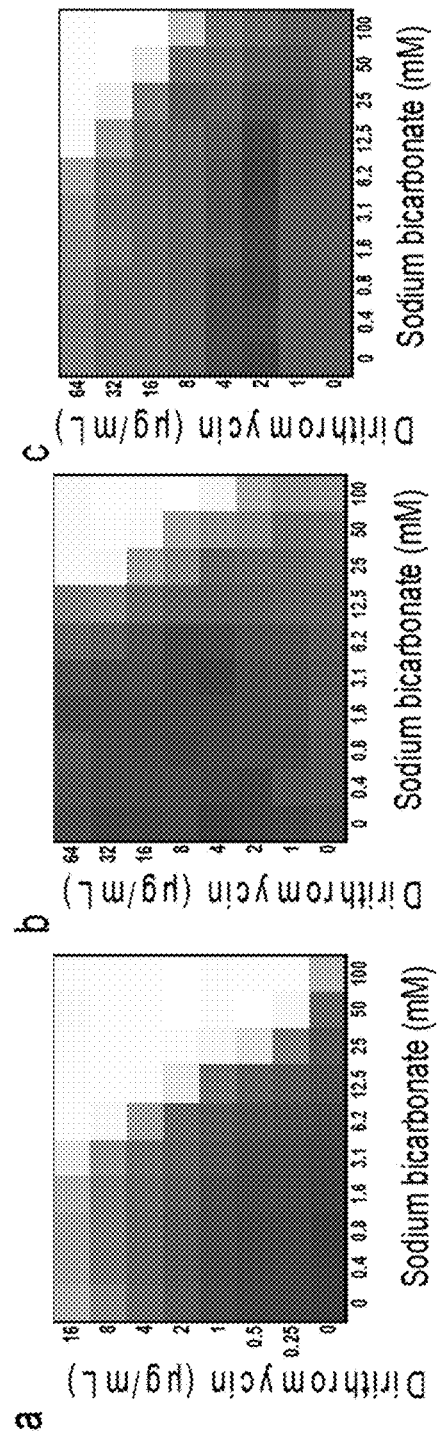
FIG. 8C, Panels a-c

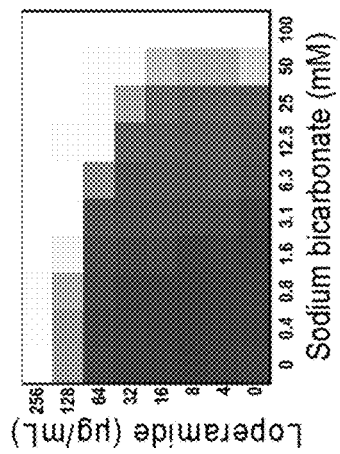
FIG. 18B
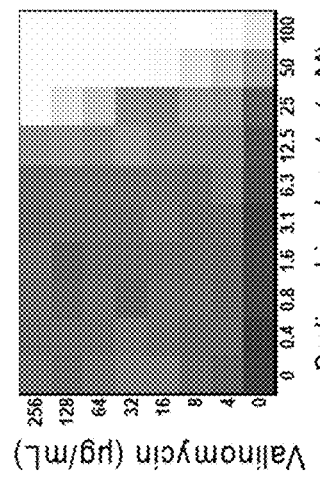
FIG. 18A
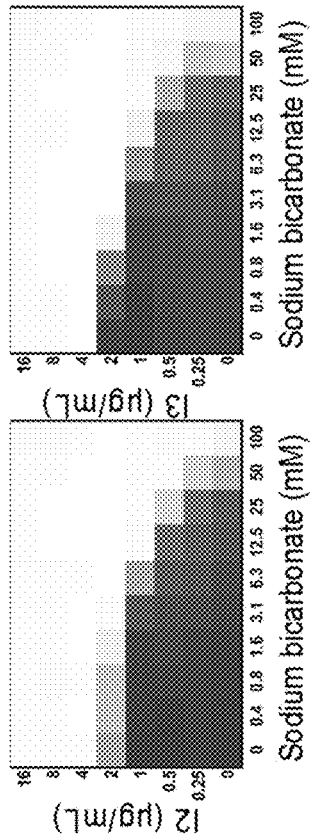
FIG. 18E
FIG. 18D
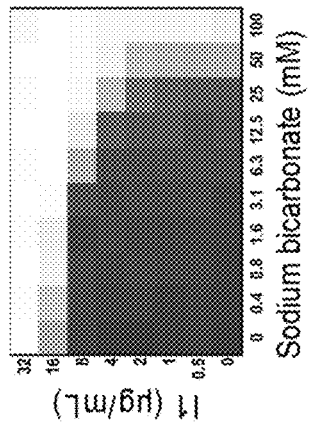
FIG. 18C

US 11,400,106 B2

METHODS FOR INHIBITING MICROBE GROWTH

This application is a continuation of International Patent Application No. PCT/CA2019/051059, filed Aug. 1, 2019, which claims the benefit of U.S. Provisional Patent Application No. 62/713,231, filed Aug. 1, 2018, the disclosure of each of which is hereby incorporated by reference herein in its entirety.

FIELD OF THE INVENTION

The present application relates to compositions and methods useful for inhibiting microbe growth and use of bicarbonate to enhance the activity of antimicrobial agents.

BACKGROUND OF THE INVENTION

There has been a steady increase in the use of antimicrobial agents, such as antibiotic agents and anti-fungal agents. Over the past 20 years, there has been an explosion in the prevalence of antibiotic resistant bacterial infections, both in the hospital and in the general community. Notably, the ESKAPE pathogens (*Enterococcus faecium, Staphylococcus aureus, Klebsiella pneumoniae, Acinetobacter baumannii, Pseudomonas aeruginosa*, and *Enterobacter* species) are responsible for a substantial percentage of nosocomial infections and present serious therapeutic challenges for physicians. These multi-drug resistant infections increase morbidity and mortality and require broad-spectrum antimicrobial coverage, or the increased usage of antibiotic agents.

Needed are ways than can further potentiate the response of microbes to various antimicrobial agents, in order to achieve control of activity of antimicrobial agents, useful in various contexts.

For example, needed are methods to potentiate the response of a microbe to an antimicrobial agent, allowing for either a greater response at a given concentration of the antimicrobial agent, or an increased response at a lower concentration of the antimicrobial agent. This could, for example, establish a way by which to preserve the efficacy of existing antimicrobial agents that may work better in a host than originally thought or a means to use molecules that had not been previously used as antimicrobial agents.

SUMMARY OF THE INVENTION

The invention provides methods for inhibiting growth of a microbe, comprising contacting the microbe with an effective amount of (i) bicarbonate and (ii) an antimicrobial agent,
wherein:
the bicarbonate is present in a composition
(a) at a concentration of about 1 millimoles/L to about 900 millimoles/L of the composition; or
(b) in an amount of about 0.01 wt % to about 8.4 wt % of the composition; and the antimicrobial agent is present in a composition
(a') in an amount of about 0.01 mg to about 25.0 mg of antimicrobial agent/mL of the composition; or
(b') in an amount of about 0.01 mg to about 25.0 mg antimicrobial agent/g of composition.
The invention also provides methods for treating or preventing a microbial infection, comprising administering to a subject in need thereof an effective amount of (i) bicarbonate and (ii) an antimicrobial agent;
wherein:
the bicarbonate is present in a composition
(a) at a concentration of about 1 millimoles/L to about 900 millimoles/L of the composition; or
(b) in an amount of about 0.01 wt % to about 8.4 wt % of the composition; and the antimicrobial agent is present in a composition
(a') in an amount of about 0.01 mg to about 25.0 mg of antimicrobial agent/mL of the composition; or
(b') in an amount of about 0.01 mg to about 25.0 mg antimicrobial agent/g of composition.

The invention provides methods for inhibiting growth of a microbe, comprising contacting the microbe with an effective amount of (i) bicarbonate and (ii) an antimicrobial agent;
wherein the antimicrobial agent is furadinozoline, gramicidin, hygromycin B, thiostrepton, bromocriptine mesylate, aminacrine, acrisorcin, mitoxantrone hydrochloride, amsacrine, homidium bromide, sulfamethazine, sulfaphenazole, chloroxine, acriflavinium hydrochloride, diminazene aceturate, sulfapyridine, ropinirole hydrochloride, sulfaguanidine, metergoline, closantel, sulfameter, cefalonium, sulfadoxine, doxorubicin, cetrimonium bromide, phenylmercuric acetate, dequalinium chloride, clioquinol, amiodarone hydrochloride, monobenzone, proflavine hemi sulfate, nisoldipine, methylbenzethonium chloride, cephalothin sodium, fluvoxamine maleate, tacrine hydrochloride, guanabenz acetate, ramoplanin, orlistat, clofoctol, puromycin hydrochloride, broxaldine, sanguinarine sulfate, dihydrostreptomycin sulfate, octisalate, ethacridine lactate, bithionate sodium, montelukast sodium, oltipraz, ipratropium bromide, ipriflavone, enalapril maleate, flopropione, sulfaquinoxaline sodium, bisoctrizole, azathioprine, enalaprilat, exalamide, benzalkonium chloride, benzethonium chloride, cetrimonium bromide, cetylpyridinium chloride, chlorhexidine, dibrompropamidine diisetionate, hexadecyltrimethylammonium bromide, p-hydroxybenzoate, polyhexanide or a polyvinylpyrrolidone iodine complex, or a pharmacetically acceptable salt thereof.

The invention also provides methods for treating or preventing a microbial infection, comprising administering to a subject in need thereof an effective amount of (i) bicarbonate and (ii) an antimicrobial agent;
wherein the antimicrobial agent is furadinozoline, gramicidin, hygromycin B, thiostrepton, bromocriptine mesylate, aminacrine, acrisorcin, mitoxantrone hydrochloride, amsacrine, homidium bromide, sulfamethazine, sulfaphenazole, chloroxine, acriflavinium hydrochloride, diminazene aceturate, sulfapyridine, ropinirole hydrochloride, sulfaguanidine, metergoline, closantel, sulfameter, cefalonium, sulfadoxine, doxorubicin, cetrimonium bromide, phenylmercuric acetate, dequalinium chloride, clioquinol, amiodarone hydrochloride, monobenzone, proflavine hemisulfate, nisoldipine, methylbenzethonium chloride, cephalothin sodium, fluvoxamine maleate, tacrine hydrochloride, guanabenz acetate, ramoplanin, orlistat, clofoctol, puromycin hydrochloride, broxaldine, sanguinarine sulfate, dihydrostreptomycin sulfate, octisalate, ethacridine lactate, bithionate sodium, montelukast sodium, oltipraz, ipratropium bromide, ipriflavone, enalapril maleate, flopropione, sulfaquinoxaline sodium, bisoctrizole, azathioprine, enalaprilat, exalamide, benzalkonium chloride, benzethonium chloride, cetrimonium bromide, cetylpyridinium chloride, chlorhexidine, dibrompropamidine diisetionate, hexadecyltrimethylammonium bromide, p-hydroxybenzoate, polyhexanide or a polyvinylpyrrolidone iodine complex, or a pharmaceutically acceptable salt thereof.

The invention also provides compositions comprising:
an effective amount of (i) bicarbonate and (ii) an antimicrobial agent;
wherein:
the bicarbonate is present in the composition
(a) at a concentration of about 1 millimoles to about 900 millimoles/L of the composition; or
(b) in an amount of about 0.01 wt % to about 8.4 wt % of the composition; and
the antimicrobial agent is present in the composition
(a') in an amount of about 0.01 mg to about 25.0 mg of antimicrobial agent/mL of the composition; or
(b') in an amount of about 0.01 mg to about 25.0 mg antimicrobial agent/g of composition.

The invention also provides compositions comprising:
an effective amount of (i) bicarbonate and (ii) an antimicrobial agent;
wherein the antimicrobial agent is furadinozoline, gramicidin, hygromycin B, thiostrepton, bromocriptine mesylate, aminacrine, acrisorcin, mitoxantrone hydrochloride, amsacrine, homidium bromide, sulfamethazine, sulfaphenazole, chloroxine, acriflavinium hydrochloride, diminazene aceturate, sulfapyridine, ropinirole hydrochloride, sulfaguanidine, metergoline, closantel, sulfameter, cefalonium, sulfadoxine, doxorubicin, cetrimonium bromide, phenylmercuric acetate, dequalinium chloride, clioquinol, amiodarone hydrochloride, monobenzone, proflavine hemisulfate, nisoldipine, methylbenzethonium chloride, cephalothin sodium, fluvoxamine maleate, tacrine hydrochloride, guanabenz acetate, ramoplanin, orlistat, clofoctol, puromycin hydrochloride, broxaldine, sanguinarine sulfate, dihydrostreptomycin sulfate, octisalate, ethacridine lactate, bithionate sodium, montelukast sodium, oltipraz, ipratropium bromide, ipriflavone, enalapril maleate, flopropione, sulfaquinoxaline sodium, bisoctrizole, azathioprine, enalaprilat, exalamide, benzalkonium chloride, benzethonium chloride, cetrimonium bromide, cetylpyridinium chloride, chlorhexidine, dibrompropamidine diisetionate, hexadecyltrimethylammonium bromide, p-hydroxybenzoate, polyhexanide or a polyvinylpyrrolidone iodine complex, or a pharmaceutically acceptable salt thereof.

BRIEF DESCRIPTION OF THE DRAWINGS

Embodiments of the invention are shown in more depth by the following descriptions of their respective drawings listed below.

FIG. 8C, Panels a-c, show the of dirithromycin in the presence of sodium bicarbonate against multi-drug resistant clinical isolates of (a) *Acinetobacter baumannii* (b) *Klebsiella pneumoniae* and (c) *Pseudomonas aeruginosa*. The extent of inhibition of bacterial growth in each checkerboard is shown as a heat plot, such that the darkest checkerboard square represents full bacterial growth.

*S. aureus* (white bar) and sodium bicarbonate-treated *S. aureus* (gray bar), measured by a luciferin-luciferase bioluminescence assay.

Figure 17A:
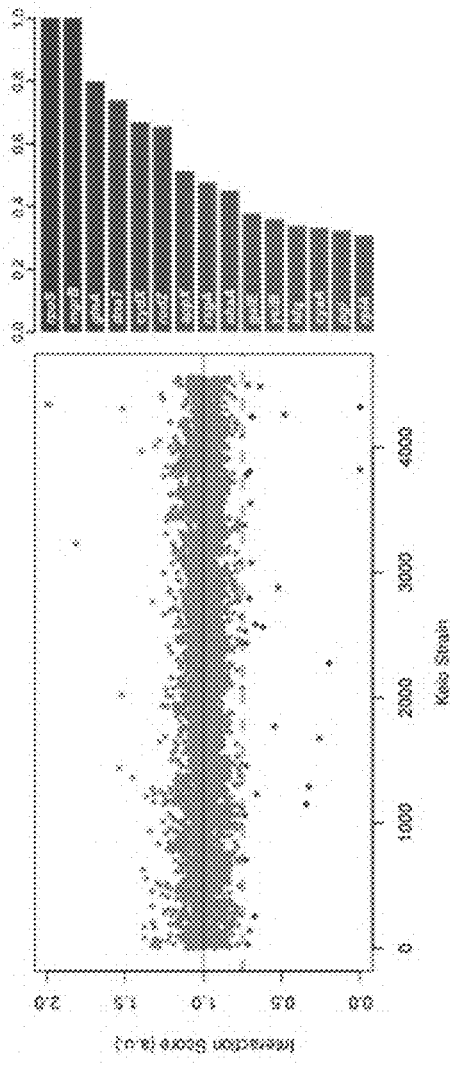
Figure 17B:
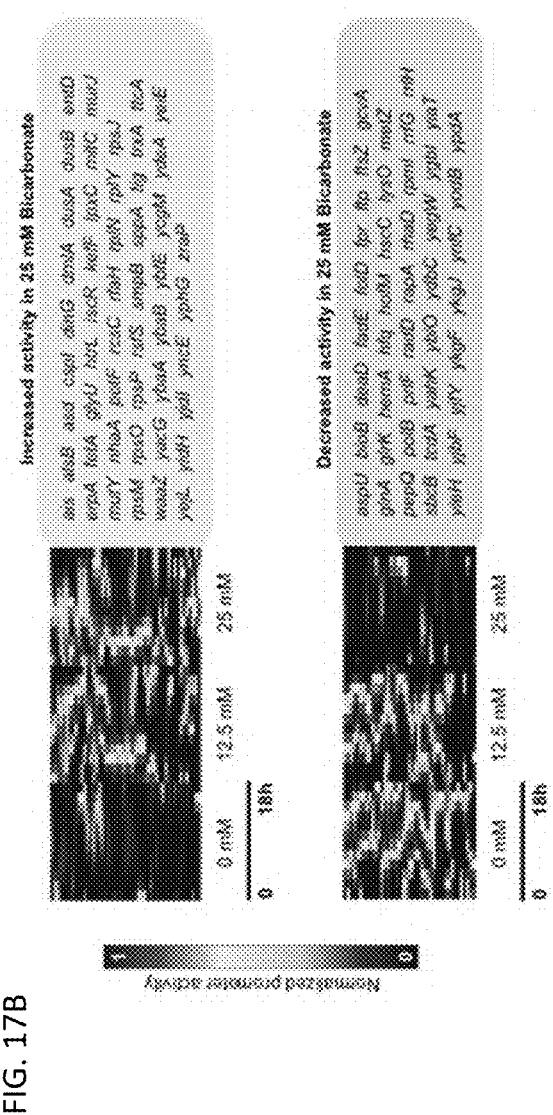

FIGS. 17A-17B show chemical-genomic interactions with 25 mM bicarbonate in *E. coli* K12.

FIGS. 18A-18E depict microdilution checkerboard analyses for molecules shown to dissipate ΔΨ, each in the presence of sodium bicarbonate. FIG. 18A shows valinomycin in *S. aureus*. FIG. 18B shows loperamide in *E. coli*. FIGS. 18C-18E show compounds I1 (FIG. 18C), I2 (FIG. 18D) and I3 (FIG. 18E) in *S. aureus*. The extent of inhibition of bacterial growth in each checkerboard is shown as a heat plot, such that the darkest checkerboard square represents full bacterial growth.

Figure 19A:
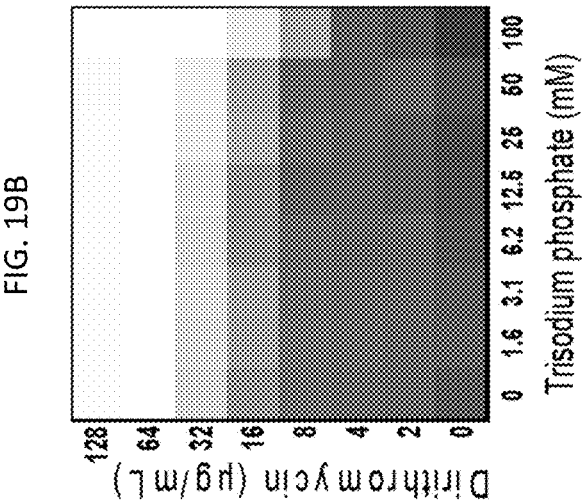
Figure 19B:
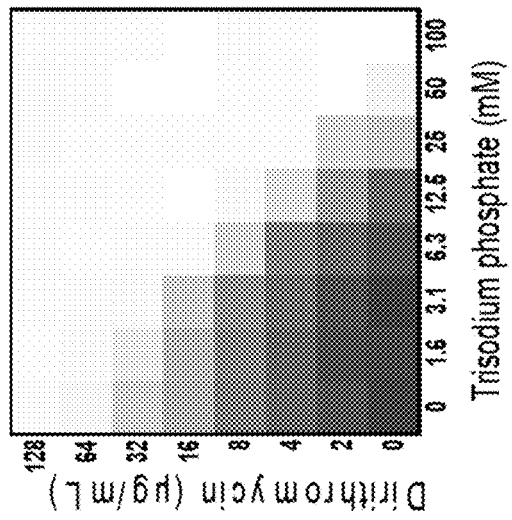

FIGS. 19A-19B show the effect of pH-adjusting media on dirithromycin in the presence of trisodium phosphate. The extent of inhibition of bacterial growth in each checkerboard is shown as a heat plot, such that the darkest checkerboard square represents full bacterial growth.

Figure 20:
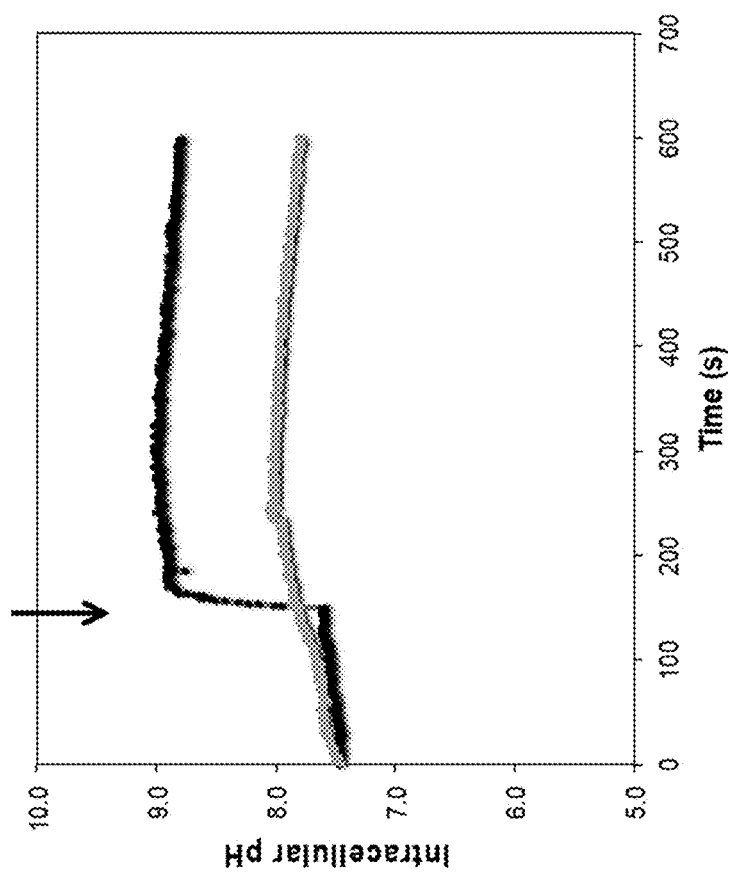

FIG. 20 is a line graph showing changes in intracellular pH upon treatment of *S. aureus* with bicarbonate.

Figure 21A:
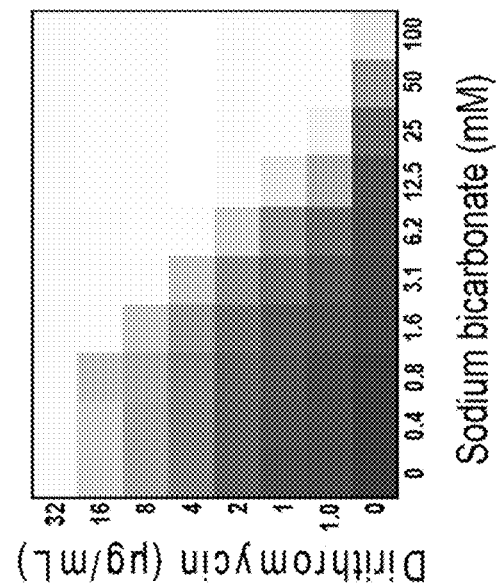
Figure 21B:
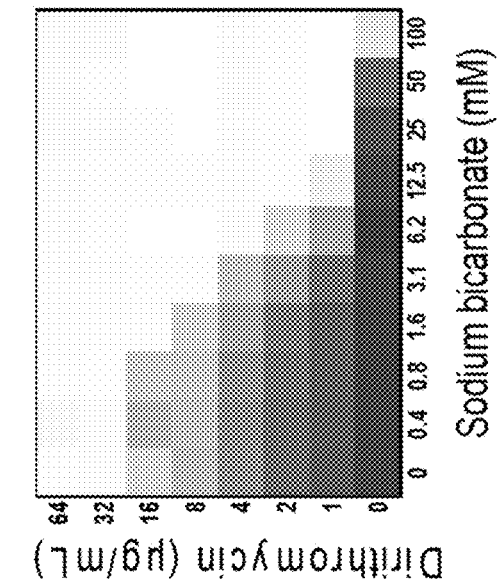

FIGS. 21A-21B show growth inhibition of wild type *E. coli* (FIG. 21A) and *E. coli* ΔychM (FIG. 21B) by dirithromycin in the presence of sodium bicarbonate. The extent of inhibition of bacterial growth in each checkerboard is shown as a heat plot, such that the darkest checkerboard square represents full bacterial growth.

Figure 22:
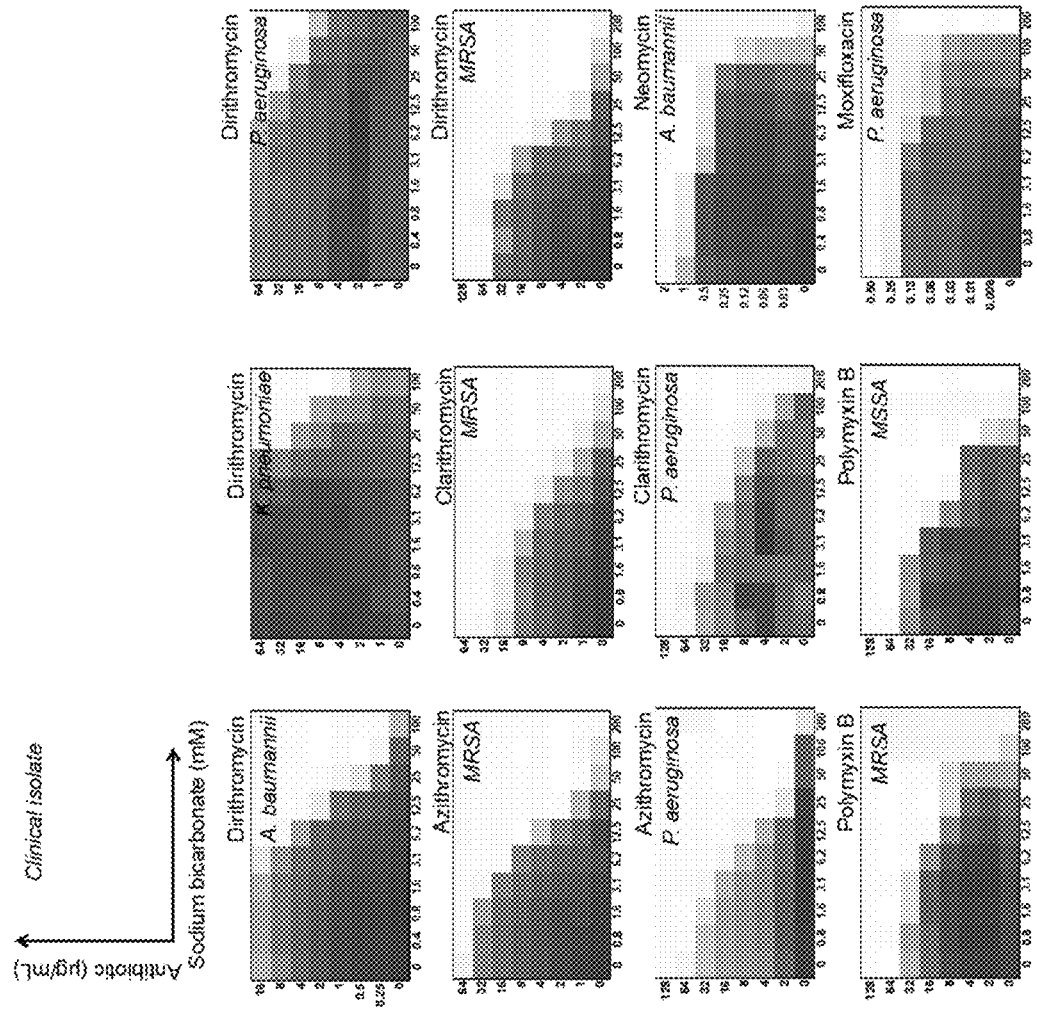

FIG. 22 shows microdilution checkerboard analyses of illustrative antibiotic agents in the presence of various sodium bicarbonate concentrations on clinical isolates of various bacteria. The extent of inhibition of bacterial growth in each checkerboard is shown as a heat plot, such that the darkest checkerboard square represents full bacterial growth.

Figure 23:
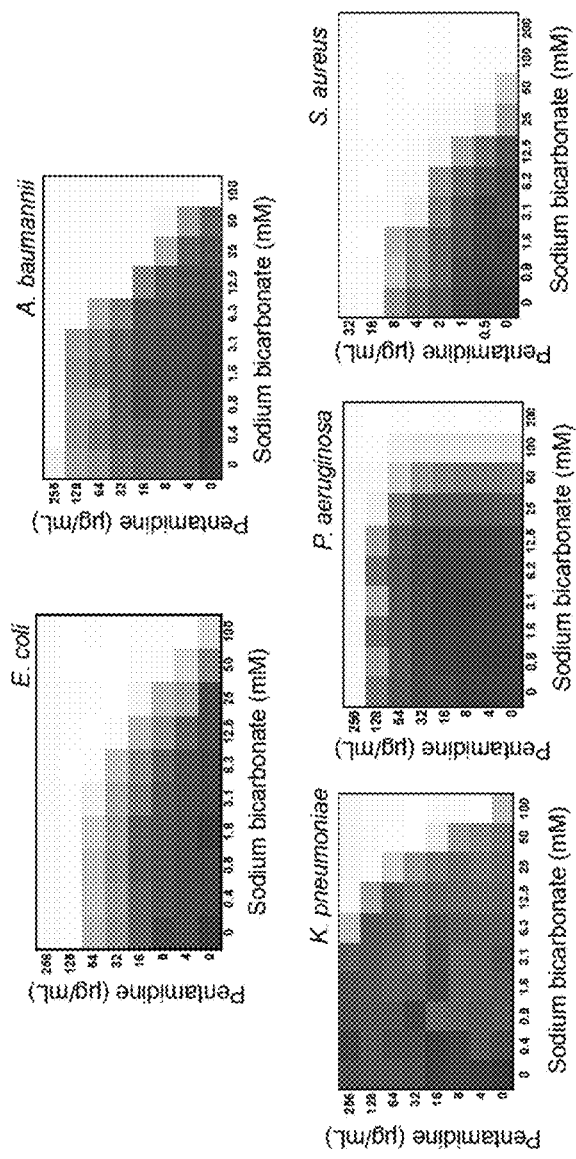

FIG. 23 shows microdilution checkerboard analyses of pentamidine in the presence of sodium bicarbonate concentrations on various bacteria. The extent of inhibition of bacterial growth in each checkerboard is shown as a heat plot, such that the darkest checkerboard square represents full bacterial growth.

Figure 24:
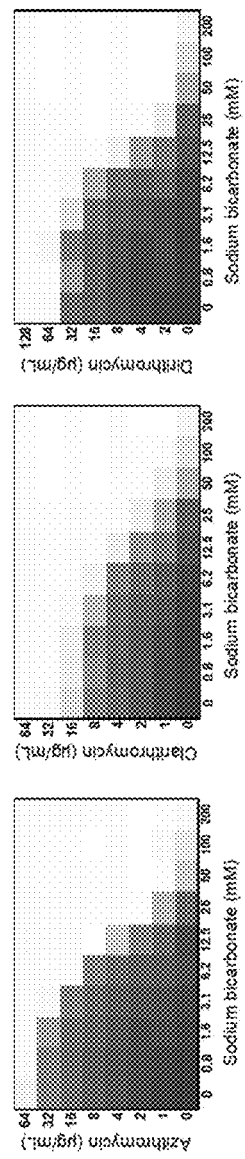

FIG. 24 shows microdilution checkerboard analyses of illustrative antibiotic agents in the presence of various sodium bicarbonate concentrations on MRSA. The extent of inhibition of bacterial growth in each checkerboard is shown as a heat plot, such that the darkest checkerboard square represents full bacterial growth.

Figure 25:
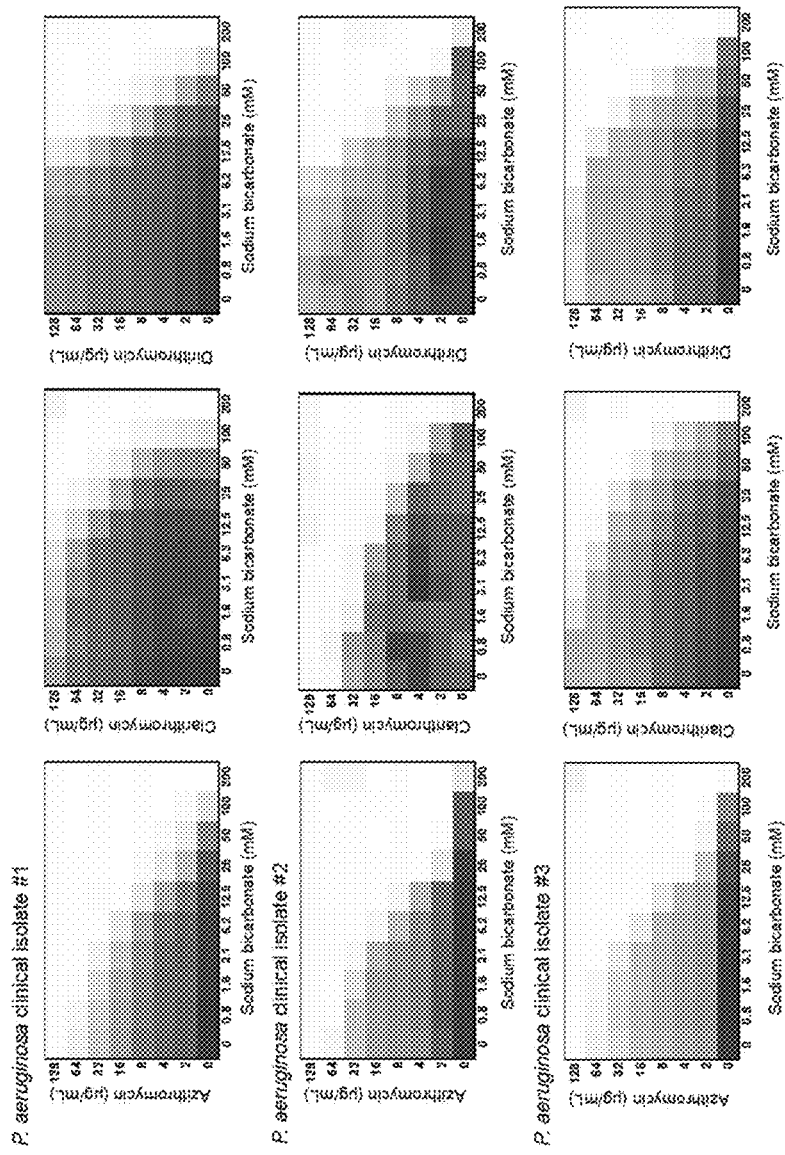

FIG. 25 shows microdilution checkerboard analyses of illustrative antibiotic agents in the presence of various sodium bicarbonate concentrations on clinical isolates of *P. aeruginosa*. The extent of inhibition of bacterial growth in each checkerboard is shown as a heat plot, such that the darkest checkerboard square represents full bacterial growth.

Figure 26:
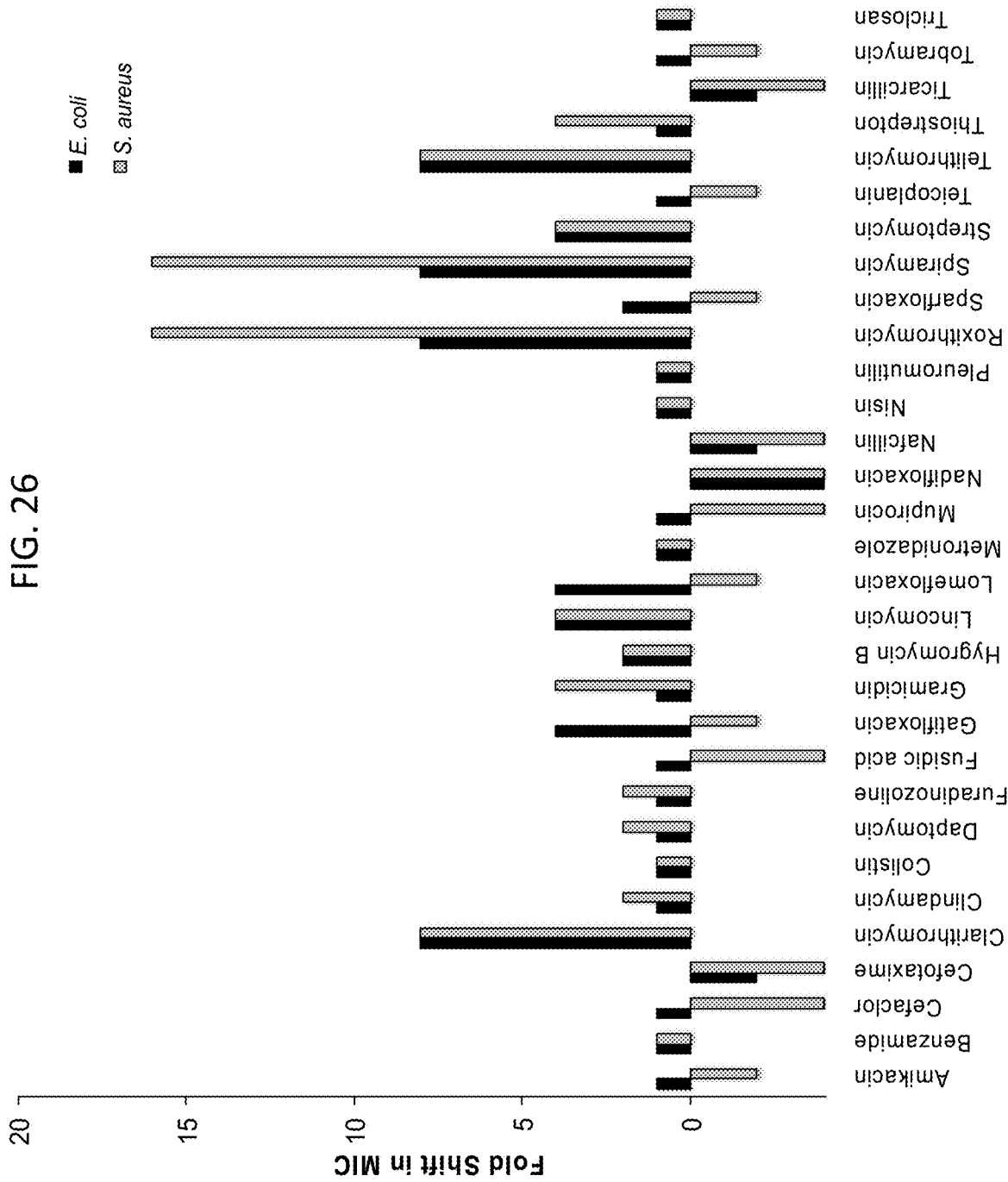

FIG. 26 shows a bar graph depicting the effect of bicarbonate on the activity of illustrative antibiotic agents on *E. coli* (black) and *S. aureus* (Newman strain) (MSSA) (gray).

Figure 27:
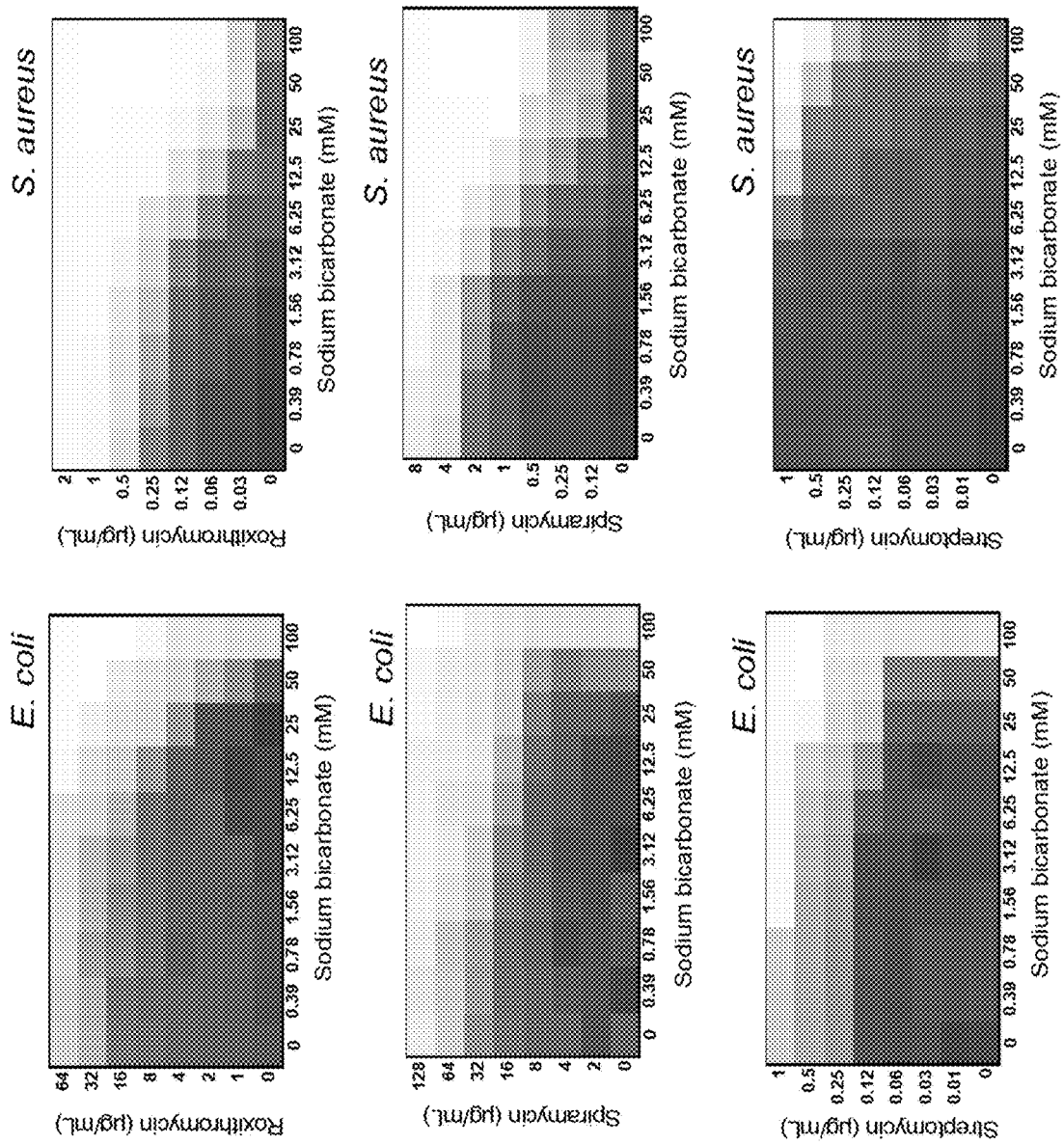

FIG. 27 shows microdilution checkerboard analyses of illustrative antibiotic agents in the presence of various sodium bicarbonate concentrations on *E. coli* and *S. aureus* (Newman strain) (MSSA). Shown are representative antibiotic agents whose activity was altered in the presence of 25 mM sodium bicarbonate. The extent of inhibition of bacterial growth in each checkerboard is shown as a heat plot, such that the darkest checkerboard square represents full bacterial growth.

Figure 28:
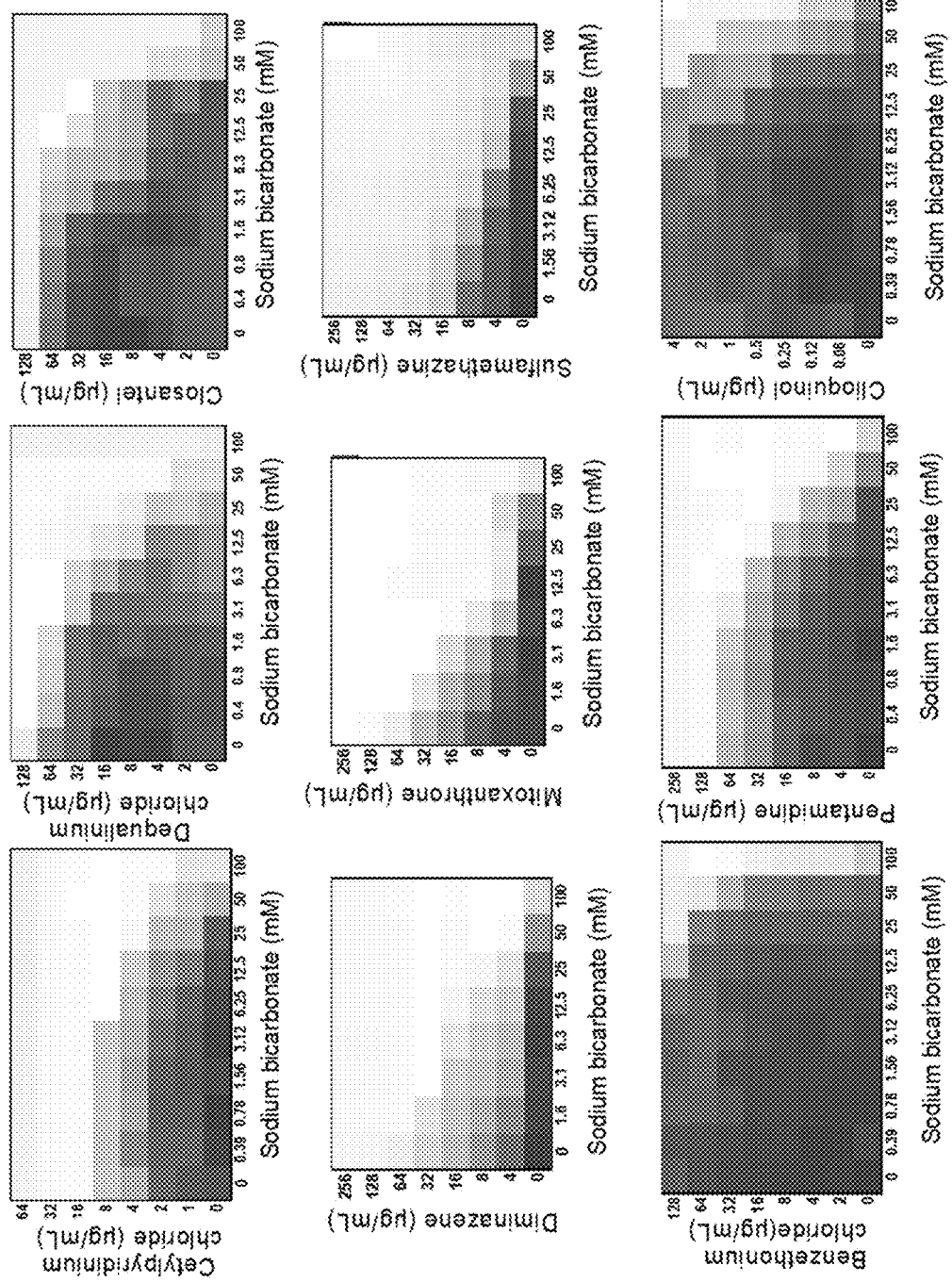

FIG. 28 shows microdilution checkerboard analyses of illustrative antibiotic agents in the presence of various sodium bicarbonate concentrations on *E. coli*. Shown are representative antibiotic agents whose activity was previously shown to be altered in the presence of 25 mM sodium bicarbonate. The extent of inhibition of bacterial growth in each checkerboard is shown as a heat plot, such that the darkest checkerboard square represents full bacterial growth.

Figure 29:
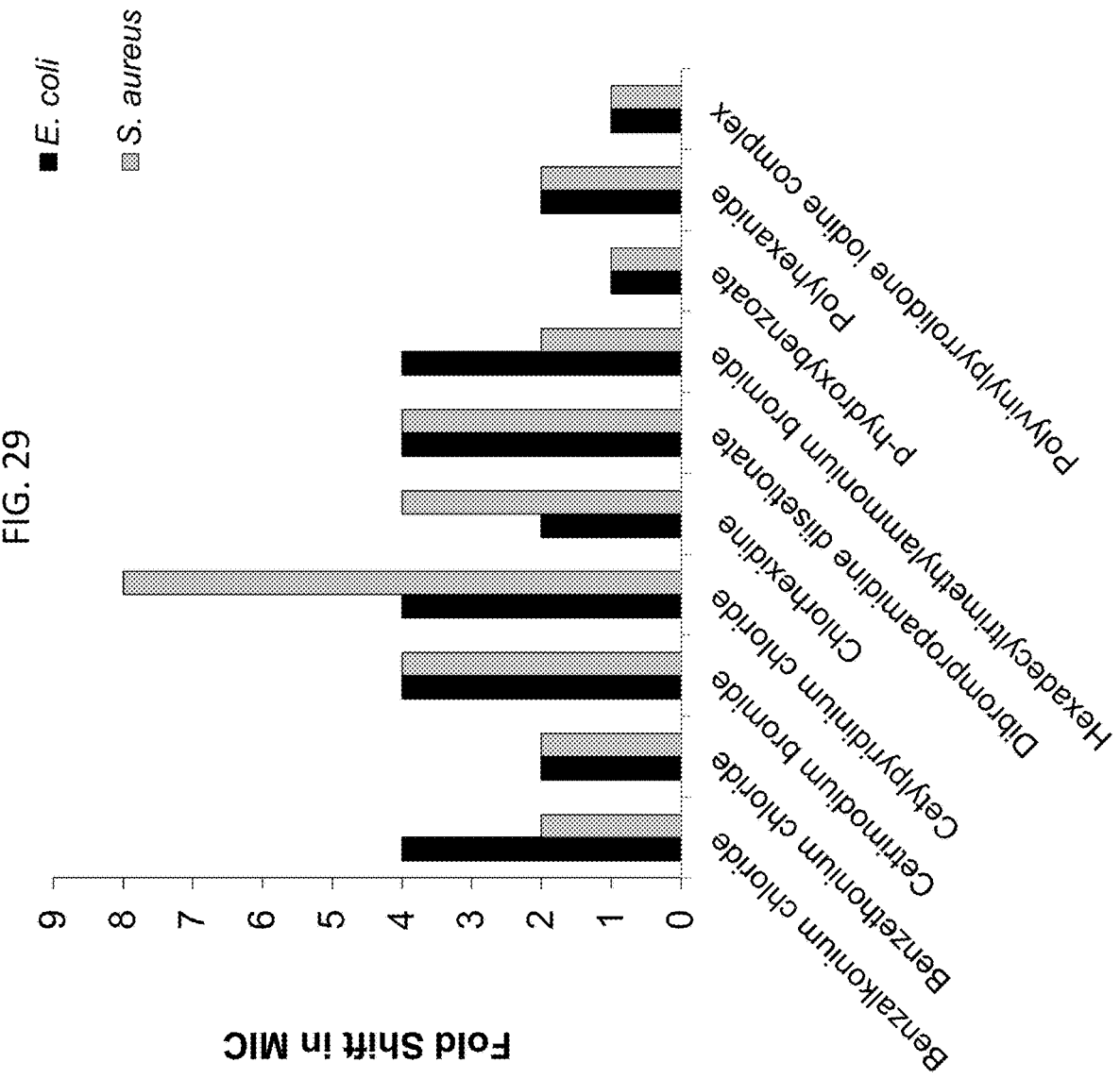

FIG. 29 is a bar graph depicting potentiation of illustrative antiseptic agents in the presence of bicarbonate on *E. coli* (black) and *S. aureus* (Newman strain) (MSSA) (gray).

Figure 30:
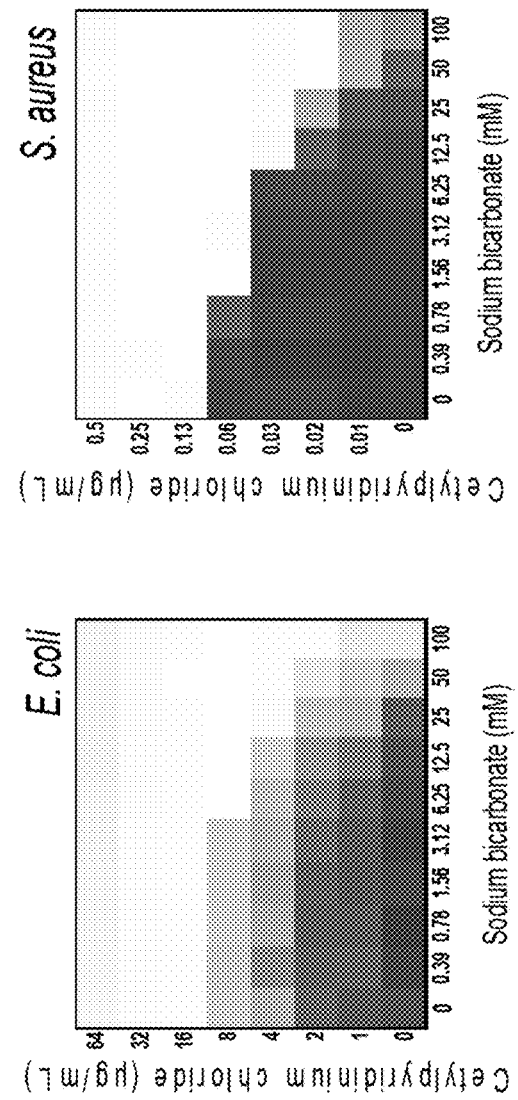

FIG. 30 shows microdilution checkerboard analyses of cetylpyridinium chloride in the presence of various sodium bicarbonate concentrations on *E. coli* and *S. aureus* (Newman strain) (MSSA). The extent of inhibition of bacterial growth in each checkerboard is shown as a heat plot, such that the darkest checkerboard square represents full bacterial growth.

Figure 31:
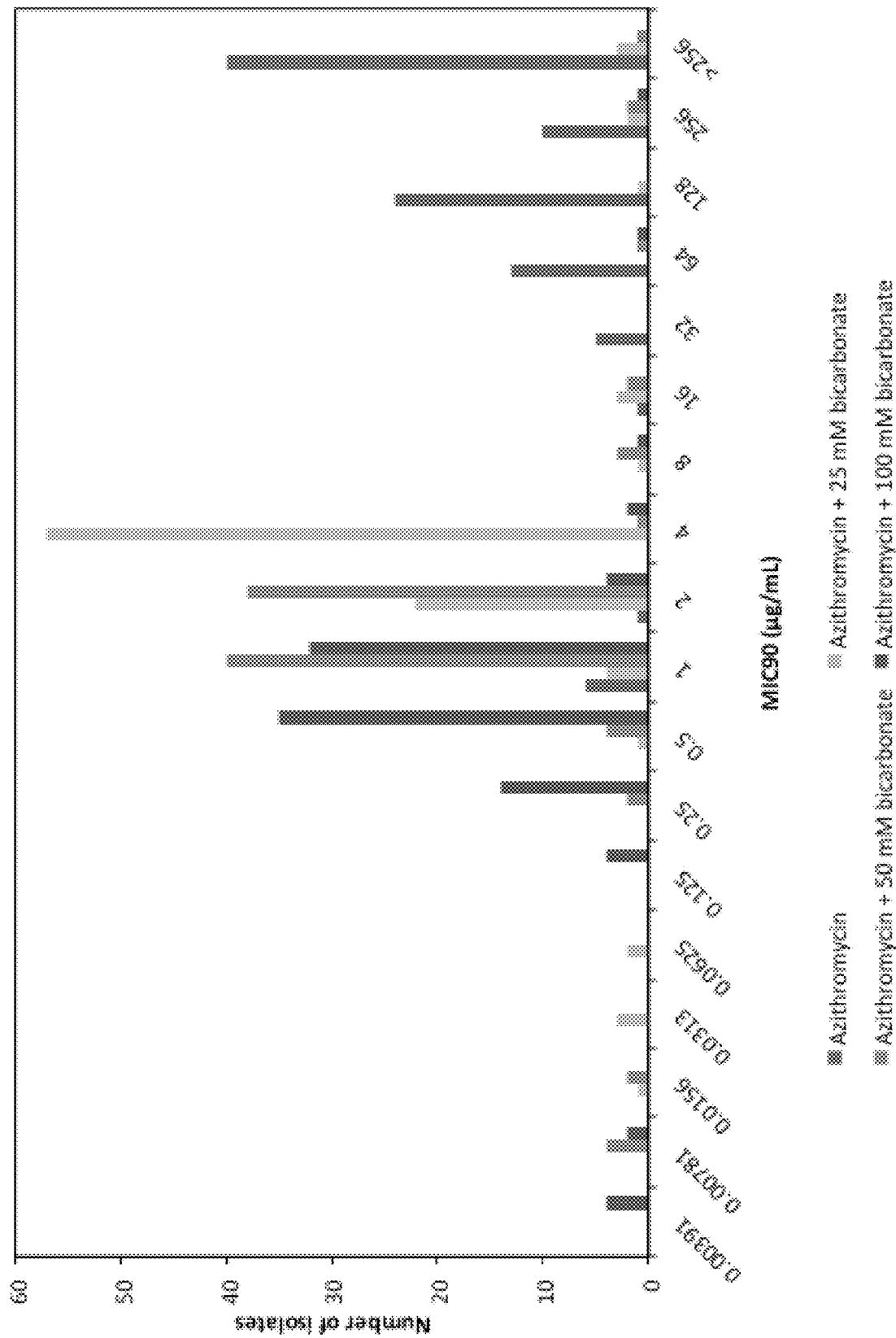

FIG. 31 is a bar graph depicting a distribution (number of isolates) of $MIC_{90}$ values for azithromycin in the absence or in the presence of various concentrations of bicarbonate on *S. aureus* (MRSA) (n=100).

Figure 32:
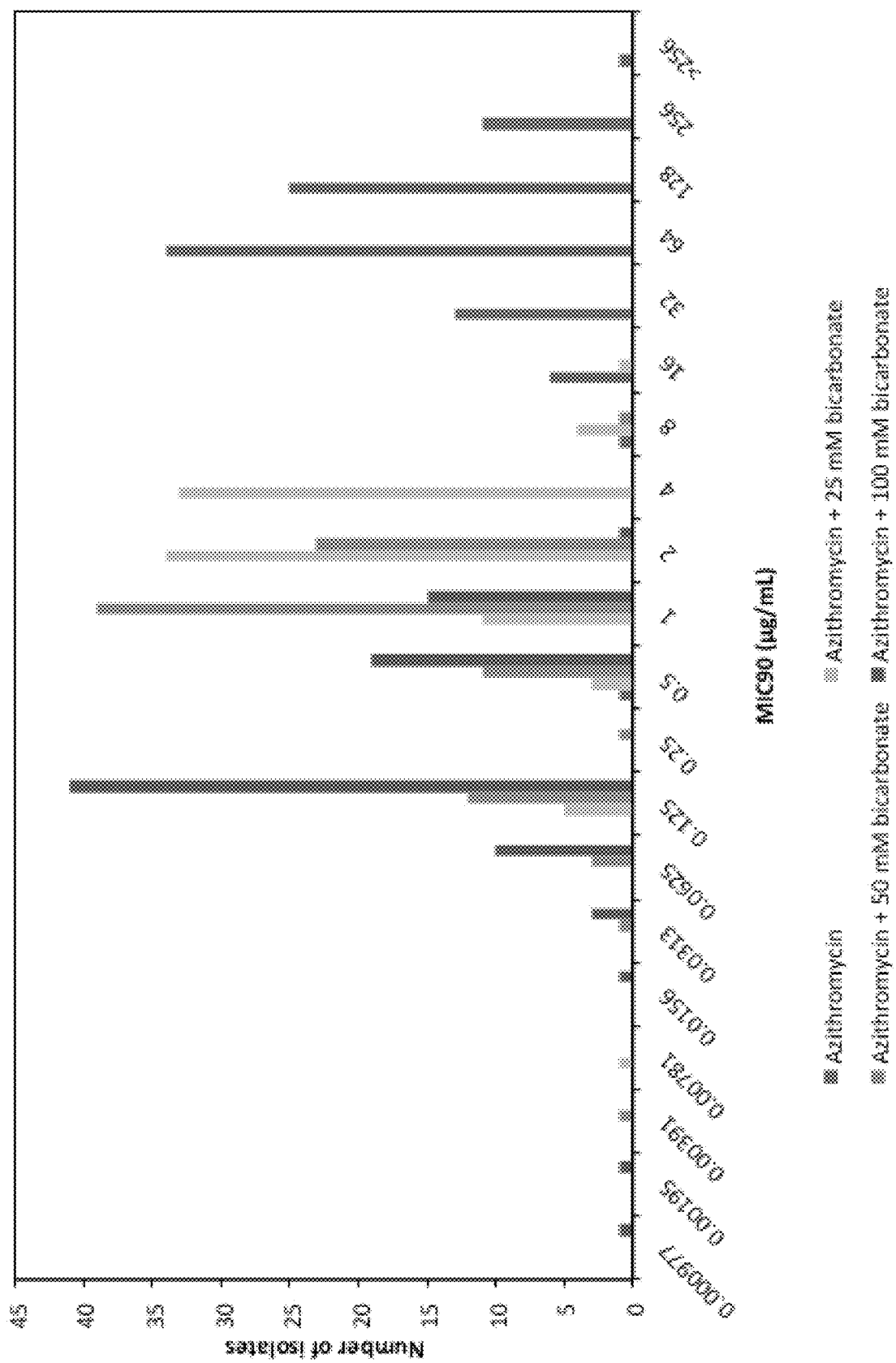

FIG. 32 is a bar graph depicting a distribution (number of isolates) of $MIC_{90}$ values for azithromycin in the absence or in the presence of various concentrations of bicarbonate on *P. aeruginosa* (n=92).

Figure 33:
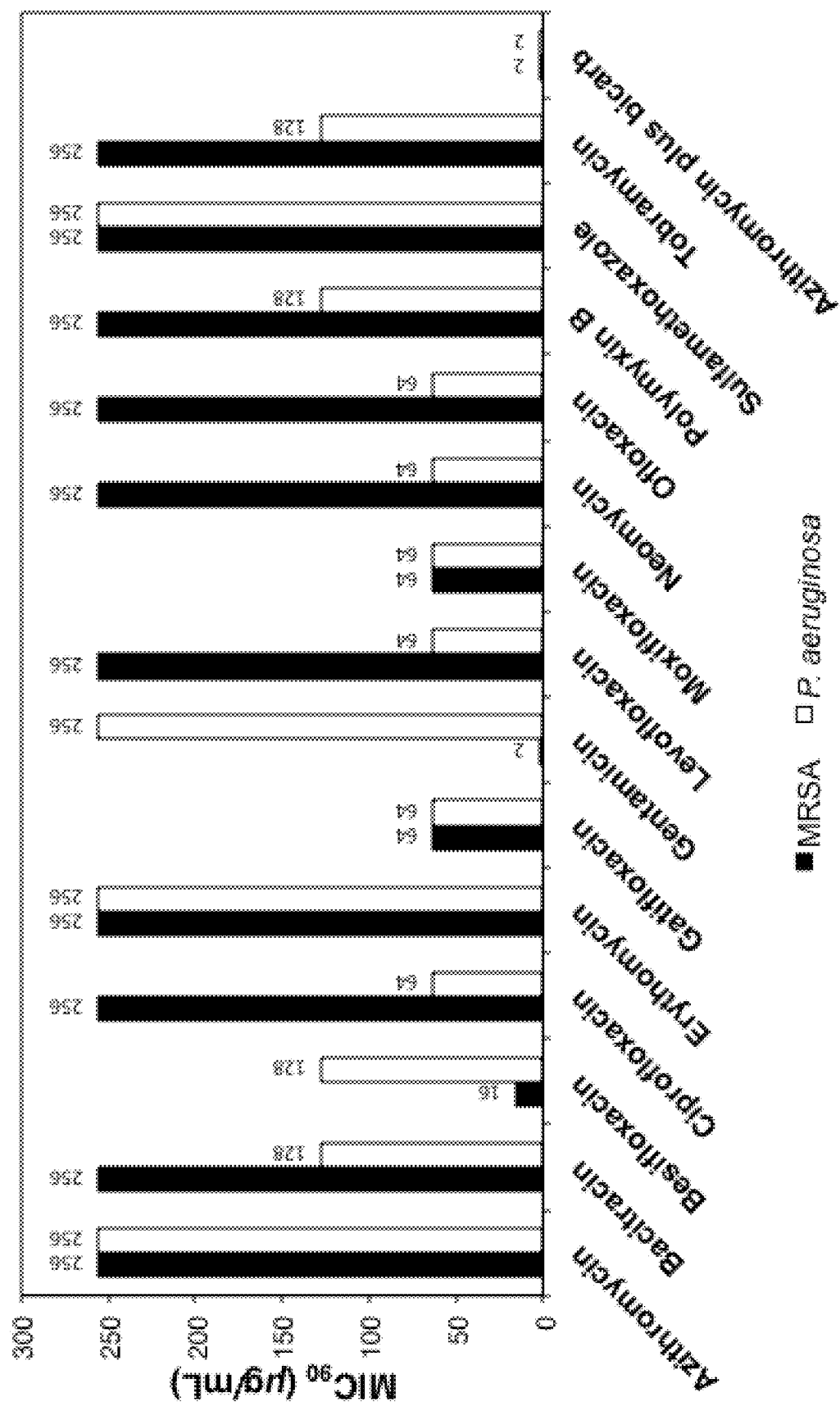

FIG. 33 is a bar graph depicting an assessment of $MIC_{90}$ values of antimicrobial agents in the absence of bicarbonate in comparison to treatment with "Azithromycin plus bicarb" (azithromycin and 50 mM sodium bicarbonate). The $MIC_{90}$ values against MRSA (n=100) are shown in black and those against *P. aeruginosa* (n=92) in white.

Figure 34B:
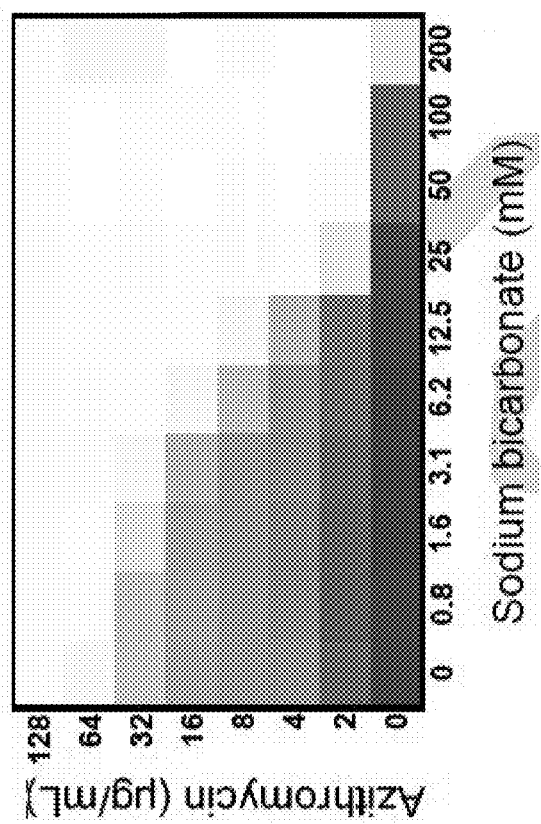
Figure 34A:
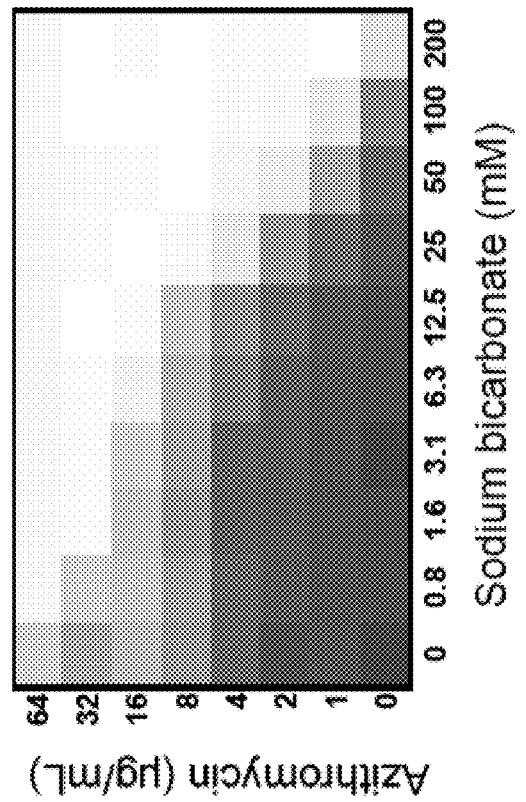

FIG. 34A and FIG. 34B show microdilution checkerboard analyses of azithromycin in the presence of various sodium bicarbonate concentrations on *S. aureus* (MRSA) (FIG. 34A) and *P. aeruginosa* (FIG. 34B). The extent of inhibition of bacterial growth in each checkerboard is shown as a heat plot, such that the darkest checkerboard square represents full bacterial growth.

Figure 35:
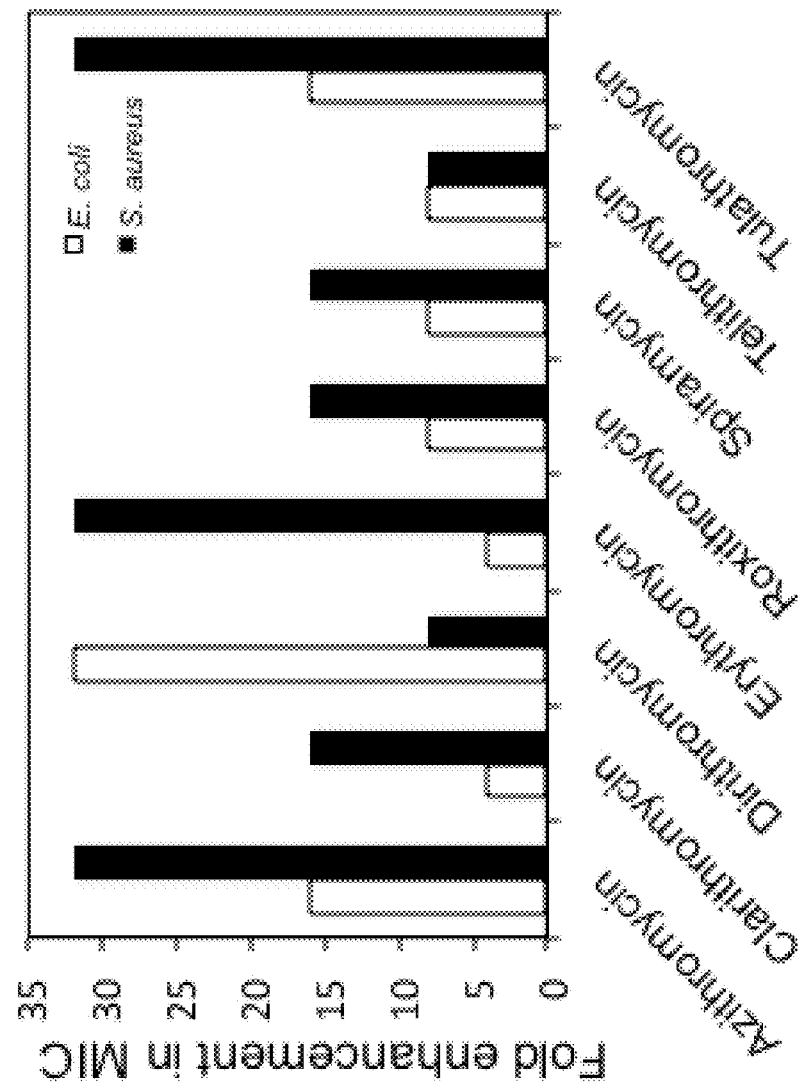

FIG. 35 is a bar graph depicting fold enhancement by 25 mM sodium bicarbonate of the MIC of various macrolide antibiotics against *E. coli* (white) and *S. aureus* (MRSA) (black).

Figure 36:
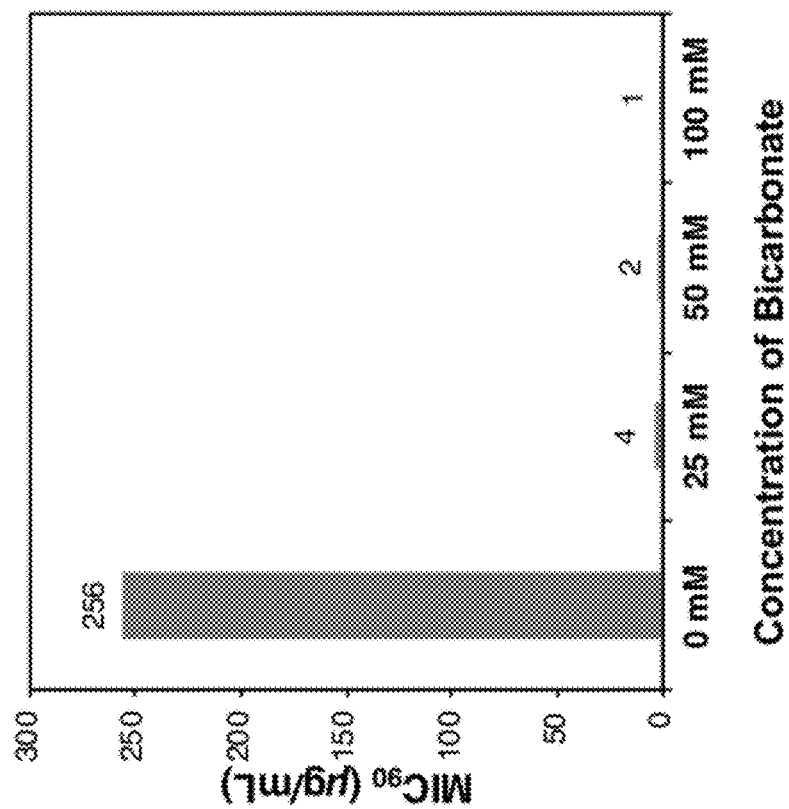

FIG. 36 is a bar graph depicting $MIC_{90}$ measurements for azithromycin against *S. aureus* (MRSA) as a function of sodium bicarbonate concentration.

Figure 37:
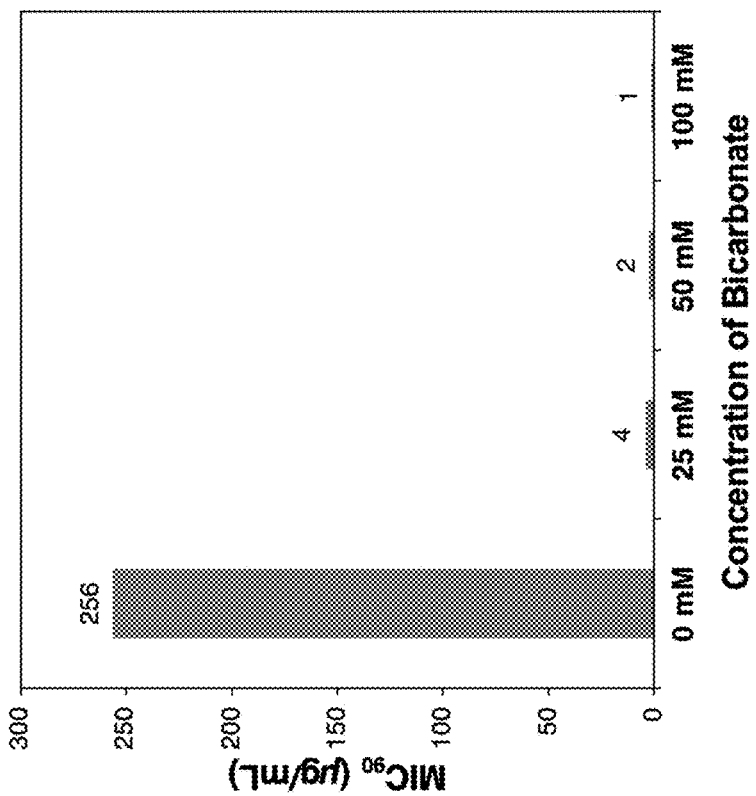

FIG. 37 is a bar graph depicting $MIC_{90}$ measurements for azithromycin against *P. aeruginosa* as a function of sodium bicarbonate concentration.

Figure 38:
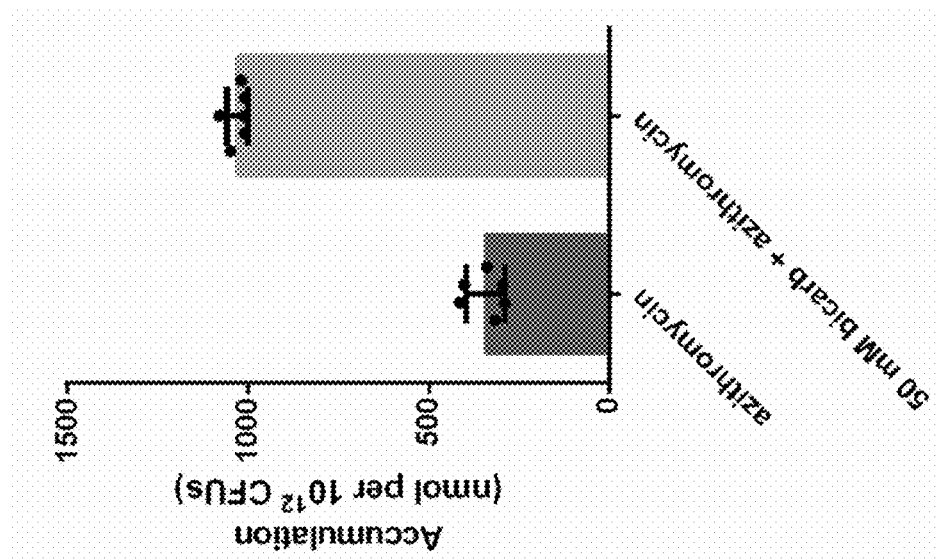

FIG. 38 is a bar graph depicting cellular accumulation of azithromycin into a macrolide-resistant strain of MRSA in the absence or presence of 50 mM sodium bicarbonate. "CFUs" refers to "colony-forming units".

Figure 39:
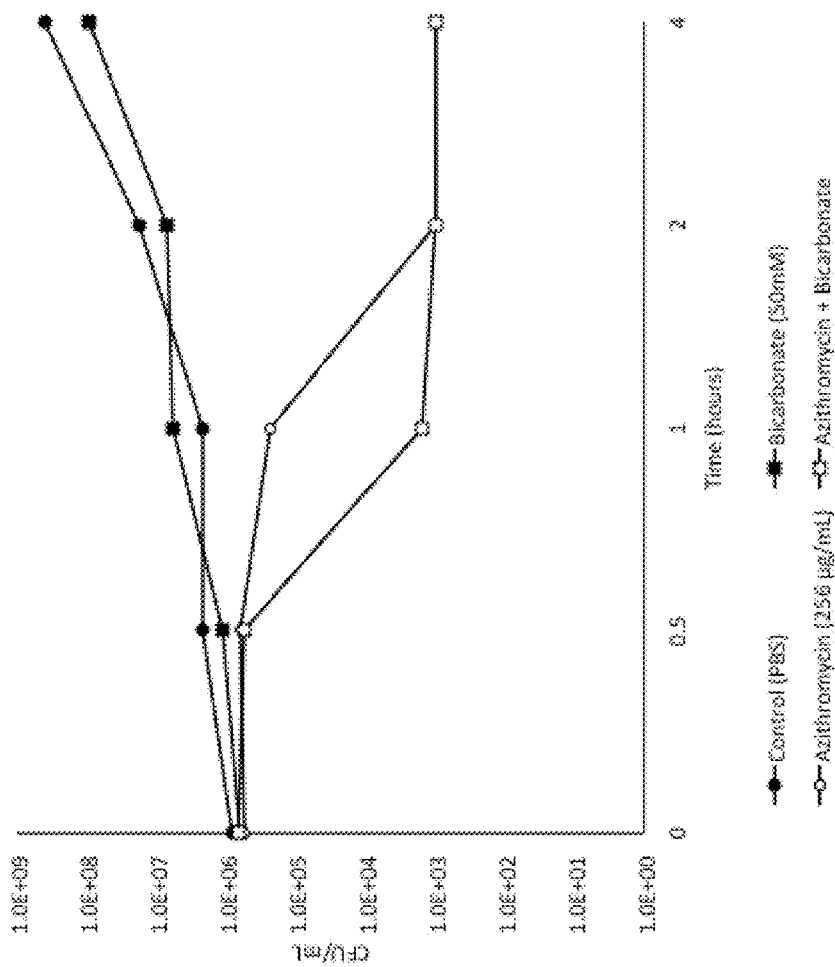

FIG. 39 is a line graph depicting time kill curves of azithromycin against MRSA in the absence or presence of 50 mM sodium bicarbonate, 50 mM sodium bicarbonate in the absence of azithromycin and a PBS control. "CFU" refers to "colony-forming unit".

Figure 40:
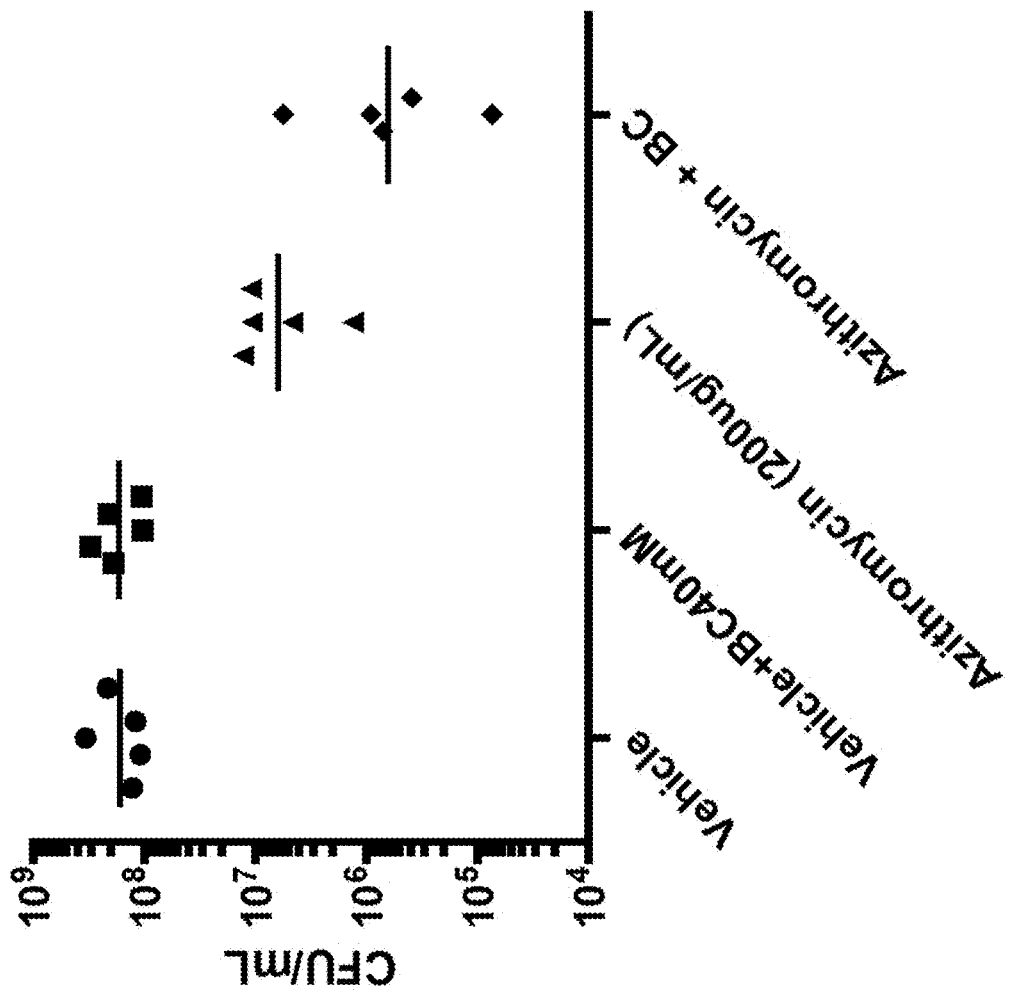

FIG. 40 is a graph depicting the effect of azithromycin in the absence or presence of sodium bicarbonate in an animal model of skin infection with *P. aeruginosa*. "CFU" refers to "colony-forming unit". The following were applied to the wound area: Vehicle (5 mg/mL methylcellulose, 1% DMSO); Vehicle+BC40 mM (5 mg/mL methylcellulose, 1% DMSO, 40 mM sodium bicarbonate); Azithromycin (5 mg/mL methylcellulose, 200 µg/mL Azithromycin) and Azithromycin+BC (5 mg/mL methylcellulose, 200 µg/mL Azithromycin, 40 mM sodium bicarbonate) (n=5).

DETAILED DESCRIPTION OF THE INVENTION

The compositions and methods of the invention are useful for inhibiting growth of a microbe. The compositions and methods of the invention are further useful for treating or preventing a microbial infection.

Definitions

The term "about" when immediately preceding a numerical value means±0% to 10% of the numerical value, ±0% to 10%, ±0% to 9%, ±0% to 8%, ±0% to 7%, ±0% to 6%, ±0% to 5%, ±0% to 4%, ±0% to 3%, ±0% to 2%, ±0% to 1%, ±0% to less than 1%, or any other value or range of values therein. For example, "about 40" means±0% to 10% of 40 (i.e., from 36 to 44).

In some embodiments referencing an "additional" or "second" component, such as an additional or second antimicrobial agent, the second component is non-identical to the other components or first component. In some embodiments, a "third" component is non-identical to the other, first, and second components, and in some embodiments, further enumerated or "additional" components are similarly different.

The term "microbial infection" as used herein refers to an infection by a microbe.

The term "subject" as used herein means a human, a non-human primate, a horse, a cow, a sheep, a goat, a pig, a dog, a cat, a rabbit, a hamster, a guinea pig, a rat or a mouse.

The term "pharmaceutically acceptable salt" means an acid addition salt of a basic active agent, including a basic antimicrobial agent, or a base addition salt of an acidic active agent, including an acidic antimicrobial agent.

Basic active agents that form an acid addition salt include, for example, those comprising an amino group. Illustrative inorganic acids that form acid addition salts with basic active agents include hydrochloric, hydrobromic, sulfuric, nitric and phosphoric acids, as well as acidic metal salts such as sodium monohydrogen orthophosphate and potassium hydrogen sulfate. Illustrative organic acids that form acid addition salts with basic active agents include mono-, di- and tricarboxylic acids. Illustrative of such organic acids are, for example, acetic, trifluoroacetic, propionic, glycolic, lactic, pyruvic, malonic, succinic, glutaric, fumaric, malic, oxalic, tartaric, citric, ascorbic, maleic, hydroxymaleic, benzoic, hydroxybenzoic, phenylacetic, cinnamic, mandelic, salicylic, 2-phenoxybenzoic, isethionic, p-toluenesulfonic acid and other sulfonic acids such as methanesulfonic acid, ethanesulfonic acid and 2-hydroxyethanesulfonic acid. Either the mono- or di-acid salts can be formed, and such salts can exist in either a hydrated, solvated or substantially anhydrous form.

Acidic active agents that form a base addition salt include, for example, compounds comprising a carboxylic acid group. Illustrative inorganic bases that form base addition salts with acidic acid agents include lithium, sodium, potassium, calcium, magnesium or barium hydroxides, carbonates and bicarbonates, as well as ammonia. Illustrative organic bases that form base addition salts with acidic active agents include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, EGFRaine, ethylenediamine, glucosamine, methylglucamine, theobromine, purines, piperazine, piperidine, N-ethylpiperidine, polyamine resins, and the like. Illustrative organic bases are isopropylamine, diethylamine, ethanolamine, trimethylamine, dicyclohexylamine, choline, and caffeine. (See, for example, S. M. Berge, et al, "Pharmaceutical Salts," *J. Pharm. Sci.* 1977, 66, 1-19).

The formation of a desired compound salt is achieved using standard techniques. For example, the neutral compound is treated with an acid or base in a suitable solvent and the formed salt is isolated by filtration, extraction or any other suitable method.

As used herein, the term "effective amount" means an amount that is effective for inhibiting growth of a microbe or for treating or preventing a microbial infection. In some embodiments, the effective amount of the antimicrobial agent and bicarbonate is the total amount of antimicrobial agent and bicarbonate.

The term "bicarbonate" as used herein refers to a compound of the formula $XHCO_3$, wherein X is a suitable cation. In some embodiments, "bicarbonate" refers to $HCO_3^-$ together with a cation. In some embodiments, a cation is an alkali metal cation. In some embodiments, the alkali metal is sodium, lithium or potassium. In some embodiments, a cation is an alkaline earth metal cation. In some embodiments, the alkaline earth metal is magnesium or calcium. In other embodiments, bicarbonate is ammonium bicarbonate or zinc bicarbonate.

The language "cytoplasmic membrane potential" as used herein refers to difference in electric potential across the cytoplasmic membrane of a bacterium.

The language "proton motive force" ("PMF") as used herein refers to the measure of the potential energy stored as a combination of proton and voltage (electrical potential) gradients across a cell membrane. The electrical gradient is a consequence of the charge separation across the cell membrane (when the protons $H^+$ move without a counterion, such as chloride $Cl^-$).

The language "psi component of the proton motive force (PMF)" or "$\Delta\psi$", as used herein refers to transmembrane electrical potential, i.e., the difference in electrical potential across a membrane.

The term "MIC", as used herein, refers to the "minimal inhibitory concentration" of an antimicrobial agent. The term "$MIC_x$", as used herein, refers to the minimal concentration of an antimicrobial agent effective to inhibit the growth of x % of a population of microbes or of x/100 strains of a microbe.

The term "microbe", as used herein, refers to an organism or a virus that is microscopic. Microbes include single-celled and multicellular organisms.

The term "potentiate", as used herein, means increase an antimicrobial agent's antimicrobial effect on a microbe.

The term "MRSA", as used herein, refers to methicillin-resistant *Staphylococcus aureus*.

The term "MSSA", as used herein, refers to methicillin-sensitive *Staphylococcus aureus*.

The term "*E. coli* ΔtolcC", as used herein, refers to an *E. coli* mutant strain lacking the outer membrane channel of the Resistance-Nodulation-Division (RND)-system AcrAB-TolC tripartite efflux system.

The term "*E. coli* ΔychM", as used herein, refers to an *E. coli* mutant strain lacking the ychM transporter.

The term "MHB", as used herein, refers to Mueller-Hinton broth.

The term "I1", as used herein, refers to a compound whose structure is shown below.

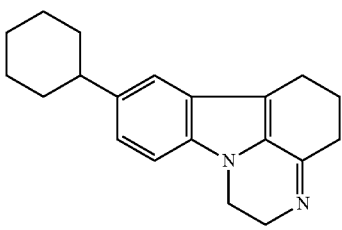

The term "I2", as used herein, refers to a compound whose structure is shown below.

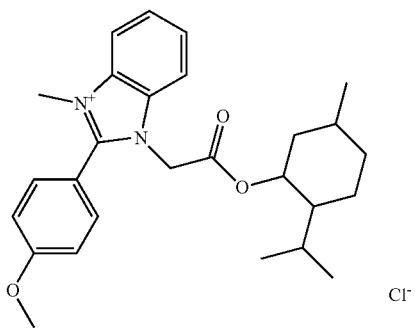

The term "I3", as used herein, refers to a compound whose structure is shown below.

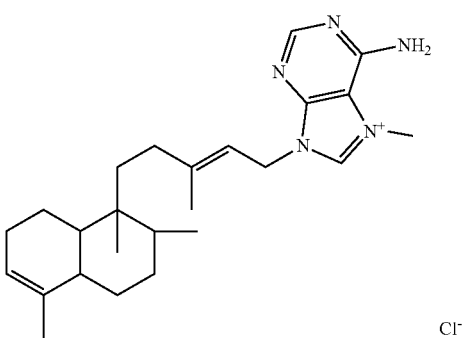

Antimicrobial Agents

In some embodiments, an antimicrobial agent is an antiviral agent, an antibiotic agent, an antiseptic agent, an anti-fungal agent, an anti-parasitic agent or an innate immunity factor. In some embodiments, an antimicrobial agent is a therapeutic agent that does not have antimicrobial activity in the absence of bicarbonate.

In some embodiments, the antimicrobial agent causes a decrease in the pH gradient across the microbe's cytoplasmic membrane. In some embodiments, the antimicrobial agent causes a decrease in the microbe's cytoplasmic membrane potential. In some embodiments, the antimicrobial agent is a cationic antimicrobial agent, an antimicrobial agent that is an energy dependent efflux substrate, an antimicrobial agent for which entry depends on membrane potential, or an antimicrobial agent that disrupts cytoplasmic membrane potential as a primary mechanism of action.

In some embodiments, an antimicrobial agent is benzamide, furadinozoline, gramicidin, hygromycin B, nadifloxacin, nisin, pleuromutilin, thiostrepton, triclosan, bromocriptine mesylate, aminacrine, acrisorcin, mitoxantrone hydrochloride, amsacrine, homidium bromide, sulfamethazine, sulfaphenazole, chloroxine, acriflavinium hydrochloride, diminazene (e.g., diminazene aceturate or diminazene diaceturate), sulfapyridine, ropinirole hydrochloride, sulfaguanidine, metergoline, closantel, sulfameter, cefalonium, sulfadoxine, doxorubicin, cetrimonium bromide, phenylmercuric acetate, dequalinium chloride, clioquinol, amiodarone hydrochloride, monobenzone, proflavine hemisulfate, nisoldipine, methylbenzethonium chloride, cephalothin sodium, fluvoxamine maleate, tacrine hydrochloride, guanabenz acetate, ramoplanin, orlistat, clofoctol, puromycin hydrochloride, broxaldine, sanguinarine sulfate, dihydrostreptomycin sulfate, octisalate, ethacridine lactate, bithionate sodium, montelukast sodium, oltipraz, ipratropium bromide, ipriflavone, enalapril maleate, flopropione, sulfaquinoxaline sodium, bisoctrizole, azathioprine, enalaprilat, exalamide, benzalkonium chloride, benzethonium chloride, cetrimonium bromide, cetylpyridinium chloride, chlorhexidine, dibrompropamidine diisetionate, hexadecyltrimethylammonium bromide, p-hydroxybenzoate, polyhexanide, a polyvinylpyrrolidone iodine complex, amikacin, azithromycin, clarithromycin, clindamycin, polymyxin B, colistin, daptomycin, fusidic acid, gatifloxacin, lincomycin, lomefloxacin, metronidazole, mupirocin, roxithromycin, sparfloxacin, spiramycin, streptomycin, teicoplanin, telithromycin or tobramycin, or a pharmaceutically acceptable salt thereof.

Antiseptic Agents

In some embodiments, an antimicrobial agent is an antiseptic agent. In some embodiments, an antimicrobial agent is a cationic antiseptic agent. In some embodiments, an antiseptic agent is benzalkonium chloride, benzethonium chloride, cetrimonium bromide, cetylpyridinium chloride, chlorhexidine, dibrompropamidine diisetionate, hexadecyltrimethylammonium bromide, p-hydroxybenzoate, polyhexanide or a polyvinylpyrrolidone iodine complex.

Antibiotic Agents

In some embodiments, an antimicrobial agent is an antibiotic agent.

In some embodiments, an antimicrobial agent is a bactericide. In some embodiments, an antimicrobial agent is a bacteriostat.

In some embodiments, the antibiotic agent is a macrolide, an aminoglycoside, a peptide, a glycopeptide, a quinolone, a fluoroquinolone or a rifampin, or a pharmaceutically acceptable salt thereof.

In some embodiments, the antibiotic agent is an aminoglycoside. Aminoglycosides include, but are not limited to, apramycin, gentamicin, kanamycin, neomycin, paromycin, and spectinomycin. In some embodiments, the antibiotic is apramycin, gentamicin, kanamycin, neomycin, paromycin or spectinomycin, or a pharmaceutically acceptable salt thereof. In some embodiments, the antibiotic agent is not kanamycin or a pharmaceutically acceptable salt thereof. In some embodiments, the antibiotic agent is not gentamicin or a pharmaceutically acceptable salt thereof. In some embodiments, the antibiotic agent is not pentamidine or a pharmaceutically acceptable salt thereof.

In some embodiments, the antibiotic agent is not an aminoglycoside or a pharmaceutically acceptable salt thereof.

In some embodiments the antibiotic agent is a macrolide. In some embodiments, the macrolide is azithromycin, clarithromycin, dirithromycin, erythromycin, roxithromycin, spiramycin, telithromycin, or tulathromycin, or a pharmaceutically acceptable salt thereof. In some embodiments, the antibiotic agent is azithromycin, or a pharmaceutically acceptable salt thereof. In some embodiments, the antibiotic agent is dirithromycin or erythromycin, or a pharmaceutically acceptable salt thereof.

In some embodiment, the antibiotic agent is not a macrolide or a pharmaceutically acceptable salt thereof.

In some embodiments the antibiotic agent is not a tetracycline or a pharmaceutically acceptable salt thereof.

In some embodiments the antibiotic agent is not a penicillin or a pharmaceutically acceptable salt thereof. In some embodiments the antibiotic agent is not ampicillin, amoxicillin, cloxacillin, nafcillin, piperacillin or oxacillin, or a pharmaceutically acceptable salt thereof.

In some embodiments the antibiotic agent is a quinolone or fluoroquinolone, or a pharmaceutically acceptable salt thereof. In some embodiments, the antibiotic agent is ciprofloxacin, besifloxacin, enoxacin, nalidixic acid, norfloxacin, levofloxacin, moxifloxacin or pefloxin, or a pharmaceutically acceptable salt thereof.

In some embodiments the antibiotic agent is not a quinolone or fluoroquinolone, or a pharmaceutically acceptable salt thereof. In some embodiments the antibiotic agent is not ciprofloxacin or a pharmaceutically acceptable salt thereof.

In some embodiments the antibiotic agent is not a cephalosporin or a pharmaceutically acceptable salt thereof. In some embodiments the antibiotic is not ceftriaxone or cefoperazone, or a pharmaceutically acceptable salt thereof.

In some embodiments the antibiotic agent is a peptide or glycopeptide, or a pharmaceutically acceptable salt thereof. In some embodiments, the antibiotic is vancomycin or polymyxin B, or a pharmaceutically acceptable salt thereof. In some embodiments, the antibiotic agent is a cathelicidin peptide or a pharmaceutically acceptable salt thereof.

In some embodiments the antibiotic agent is not a peptide or glycopeptide, or a pharmaceutically acceptable salt thereof. In some embodiments, the antibiotic agent is not a cathelicidin peptide or a pharmaceutically acceptable salt thereof.

In some embodiments, the antibiotic agent is chloramphenicol, dirithromycin, erythromycin, linezolid, bacitracin, fosfomycin, fosmidomycin, vancomycin, polymyxin B, ciprofloxacin, besifloxacin, enoxacin, nalidixic acid, norfloxacin, levofloxacin, moxifloxacin, pefloxin, novobiocin, pentamidine, rifampicin, trimethoprim or sulfamethoxazole, or a pharmaceutically acceptable salt thereof.

In some embodiments, the antibiotic agent is apramycin, neomycin, paromycin, spectinomycin, chloramphenicol, dirithromycin, erythromycin, linezolid, bacitracin, fosfomycin or fosmidomycin, or a pharmaceutically acceptable salt thereof.

In some embodiments, the antibiotic agent is erythromycin, dirithromycin, levofloxacin, norfloxacin, ciprofloxacin, enoxacin, moxifloxacin, besifloxacin or polymyxin B, or a pharmaceutically acceptable salt thereof.

In some embodiments, the antibiotic agent is novobiocin or a pharmaceutically acceptable salt thereof.

In some embodiments, the antibiotic agent is Amikacin, Apramycin, Gentamicin, Kanamycin, Neomycin, Tobramycin, Paromomycin, Streptomycin, Spectinomycin, Ertapenem, Doripenem, Imipenem/Cilastatin, Meropenem, Teicoplanin, Vancomycin, Telavancin, Clindamycin, Lincomycin, Lipopeptide, Daptomycin, Azithromycin, Clarithromycin, Dirithromycin, Erythromycin, Roxithromycin, Tulathromycin, Troleandomycin, Telithromycin, Spiramycin, Aztreonam, Linezolid, Posizolid, Radezolid, Torezolid, Bacitracin, Colistin (Polymyxin E), Polymyxin B, Besifloxacin, Ciprofloxacin, Enoxacin, Gatifloxacin, Gemifloxacin, Levofloxacin, Lomefloxacin, Moxifloxacin, Nalidixic acid, Norfloxacin, Ofloxacin, Pefloxacin, Trovafloxacin, Grepafloxacin, Sparfloxacin, Temafloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Sulfonamidochrysoidine, Arsphenamine, Chloramphenicol, Fosfomycin, Fusidic acid, Metronidazole, Mupirocin, Platensimycin, Quinupristin/Dalfopristin, Thiamphenicol, Tigecycline, Tinidazole, Trimethoprim, Clofazimine, Dapsone, Capreomycin, Cycloserine, Ethambutol, Ethionamide, Isoniazid, Pyrazinamide, Rifampicin, Rifabutin, Rifapentine or Streptomycin, or a pharmaceutically acceptable salt thereof.

In some embodiments, the antibiotic agent is a cationic antibiotic agent, an antibiotic agent that is an energy dependent efflux substrate, an antibiotic agent for which entry depends on membrane potential, or an antibiotic agent that disrupts membrane potential as a primary mechanism of action.

Innate Immunity Factors

In some embodiments, the antimicrobial agent is an innate immunity factor.

Examples of innate immunity factors include antimicrobial peptides, such as defensins; antimicrobial enzymes, such as lysozyme; antimicrobial secretions, such as hyaluronic acid; and pharmaceutically acceptable salts thereof.

Accordingly, in some embodiments, the innate immunity factor is an antimicrobial peptide, an antimicrobial enzyme, or an antimicrobial secretion. In some embodiments, the innate immunity factor is LL-37, indolicidin, bactenesin, defensin, alpha-defensin, a bile salt, lysozyme, protegrin, or hyaluronic acid, or a pharmaceutically acceptable salt thereof. In some embodiments, the innate immunity factor is a cathelicidin peptide or a pharmaceutically acceptable salt thereof. In some embodiments, the innate immunity factor is not a cathelicidin peptide or a pharmaceutically acceptable salt thereof. In some embodiments, the innate immunity factor is not LL-37 or a pharmaceutically acceptable salt thereof.

Antiviral Agents

In some embodiments, the antimicrobial agent is an antiviral agent.

In some embodiments, an antiviral agent is Abacavir, Acyclovir, Adefovir, Amantadine, Amprenavir, Ampligen, Arbidol, Atazanavir, Atripla, Balavir, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Fusion inhibitor, Ganciclovir, Ibacitabine, Imunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nitazoxanide, Nucleoside analogues, Norvir, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Sofosbuvir, Stavudine, Synergistic enhancer (antiretroviral), Telaprevir, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir or Zidovudine, or a pharmaceutically acceptable salt thereof.

Anti Fungal Agents

In some embodiments, the antimicrobial agent is an anti-fungal agent.

In some embodiments, an anti-fungal agent is Amphotericin B, Candicidin, Filipin, Hamycin, Natamycin, Nystatin, Rimocidin, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Efinaconazole, Epoxiconazole, Fluconazole, Isavuconazole, Itraconazole, Posaconazole, Propiconazole, Ravuconazole, Terconazole, Voriconazole, Abafungin, Amorolfin, Butenafine, Naftifine, and Terbinafine, Anidulafungin, Caspofungin, Micafungin, Aurones, Benzoic acid, Ciclopirox, Flucytosine, Griseofulvin, Haloprogin, Tolnaftate, Undecylenic acid, Crystal violet, Orotomide or Miltefosine, or a pharmaceutically acceptable salt thereof.

Anti Parasitic Agents

In some embodiments, the antimicrobial agent is an anti-parasitic agent.

In some embodiments, an anti-parasitic agent is Nitazoxanide, Melarsoprol, Eflornithine, Metronidazole, Tinidazole, Miltefosine, *Ancylostoma caninum*, Mebendazole, Pyrantel pamoate, Thiabendazole, Diethylcarbamazine, Ivermectin, Niclosamide, Praziquantel, Albendazole, Antitrematodes, Praziquantel, Rifampin, Amphotericin B or Fumagillin, or a pharmaceutically acceptable salt thereof.

Other Antimicrobial Agents

In some embodiments, the antimicrobial agent is diamidine or a pharmaceutically acceptable salt thereof. In some embodiments, the antimicrobial agent is diminazene or a pharmaceutically acceptable salt thereof. In some embodiments, the antimicrobial agent is diminazene aceturate or diminazene diaceturate. The structure of diminazene is shown below:

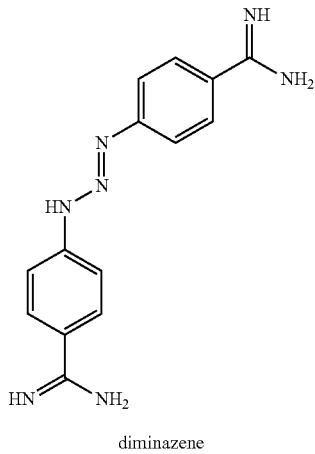 [SMILES: N=C(N)c1ccc(/N=N/Nc2ccc(C(=N)N)cc2)cc1]

diminazene

In some embodiments, the antimicrobial agent is propamidine or a pharmaceutically acceptable salt thereof. In some embodiments, the antimicrobial agent is pentamidine or a pharmaceutically acceptable salt thereof. In some embodiments, the antimicrobial agent is pentamidine isethionate. The structure of pentamidine is shown below:

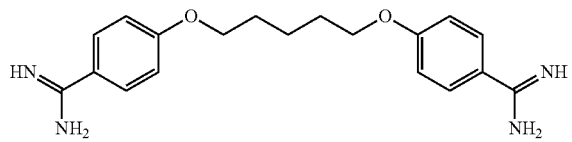

pentamidine

In some embodiments, the antimicrobial agent is a compound of Formula I:

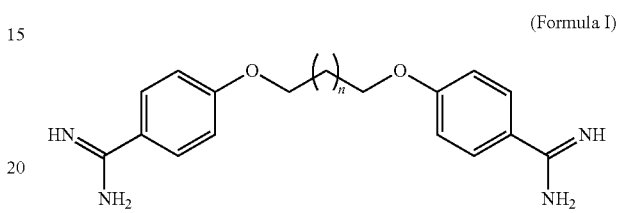

(Formula I)

or a pharmaceutically acceptable salt thereof, wherein n is 0, 1, 2, 3, 4, 5, 6, 7 or 8. In some embodiments, n is 1. In some embodiments, n is an integer ranging from 2 to 4.

In some embodiments, an antimicrobial agent is not a diamidine, or a pharmaceutically acceptable salt thereof. In some embodiments, an antimicrobial agent is not pentamidine, or a pharmaceutically acceptable salt thereof.

Microbes

In some embodiments, the microbe is a bacterium. In some embodiments, the bacterium is a Gram negative bacterium. In some embodiments, the bacterium is a Gram positive bacterium. In some embodiments, the bacterium is a spiral-shaped bacterium, a filamentous bacterium, a pleomorphic bacterium or a rectangular bacterium. In other embodiments, the bacterium is a sphere-shaped bacterium, a rod-shaped bacterium, a spiral-shaped bacterium, a filamentous bacterium, a pleomorphic bacterium or a rectangular bacterium. In some embodiments, the bacterium is a Gram positive rod-shaped bacterium. In another embodiments, the bacterium is a Gram negative rod-shaped bacterium. In yet other embodiments, the bacterium is a Gram positive sphere-shaped bacterium. In further embodiments, the bacterium is a Gram negative sphere-shaped bacterium.

In some embodiments, the bacterium is an obligate aerobe or an obligate anaerobe. In other embodiments, the bacterium is a facultative anaerobe.

In some embodiments, the bacterium is a species of *Acinetobacter, Actinomyces, Aerococcus, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum,* Spirochaetes, *Staphylococcus, Stenotrophomonas, Streptobacillus, Streptococcus, Tetragenococcus, Treponema, Vibrio, Viridans, Wolbachia* or *Yersinia*.

In some embodiments, the bacterium is *Acetobacter aurantius, Acinetobacter baumannii, Actinomyces israelii, Aerococcus viridans, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus thuringiensis, Bacteroides fragilis, Bacteroides gingivalis, Bacteroides melaninogenicus, Bartonella henselae, Bartonella quintana, Bordetella bronchiseptica, Bordetella pertussis, Borrelia burgdorferi. Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Clostridium perfringens, Clostridium tetani, Corynebacterium diphtheriae, Corynebacterium fusiforme,* CDC coryneform group G, *Coxiella burnetii, Ehrlichia chaffeensis, Enterobacter cloacae, Enterococcus avium, Enterococcus durans, Enterococcus faecalis, Enterococcus faecium, Enterococcus gallinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica, Pseudomonas aeruginosa, Rhizobium radiobacter, Rickettsia prowazekii, Rickettsia psittaci, Rickettsia quintana, Rickettsia rickettsii, Rickettsia trachomas, Rochalimaea henselae, Rochalimaea quintana, Rothia dentocariosa, Salmonella enteritidis, Salmonella typhi, Salmonella typhimurium, Serratia marcescens, Shigella dysenteriae, Spirillum volutans, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus fetus, Streptococcus gallinarum, Streptococcus lactis, Streptococcus mitior, Streptococcus mitis, Streptococcus mutans, Streptococcus oxalis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Viridans streptococci, Wolbachia, Yersinia enterocolitica, Yersinia pestis* or *Yersinia pseudotuberculosis.*

In some embodiments, the bacterium is *Escherichia coli, Acinetobacter baumannii, Klebsiella pneumoniae, Pseudomonas aeruginosa, Burkhloderia cenocepacia, Burkhloderia multivorans, Enterococcus faecalis* or *Staphylococcus aureus.* In some embodiments, the bacterium is *Escherichia coli.* In some embodiments, the bacterium is *Staphylococcus aureus.* In some embodiments of the methods described herein, the bacterium is MRSA or MSSA.

In some embodiments, the bacterium is *Staphylococcus aureus,* MRSA, *Staphylococcus epidermidis, Streptococcus pneumoniae, Haemophilus influenza, Pseudomonas aeruginosa, Chlamydia trachomatis, Moraxella* sp., *Neisseria gonorrhoeae, Corynebacterium diphtheriae,* Group A Streptococci, *Streptococcus pyogenes, Streptococcus agalactiae, Klebsiella pneumoniae, Enterobacter aerogene, Proteus vulgaris, Mycobacterium leprae, Propionibacterium acnes, Erysipelothrix rhusiopathiae, Corynebacterium minutissimum, Corynebacterium tenuis, Brevibacterium, Mycobacterium tuberculosis, Mycobacterium marinum,* or *Mycobacterium ulcerans.*

In some embodiments, the bacterium is *Staphylococcus aureus,* MRSA, *Staphylococcus epidermidis, Streptococcus pneumoniae, Haemophilus influenza, Pseudomonas aeruginosa, Chlamydia trachomatis, Moraxella* sp., *Neisseria gonorrhoeae,* or *Corynebacterium diphtheriae.*

In some embodiments, the bacterium is *Pseudomonas aeruginosa, Chlamydophila pneumoniae, Prevotella* sp., *Mycobacterium, Moraxella catarrhalis, Stenotrophomonas maltophilia, Mycoplasma pneumoniae, Mycobacterium abscessus, Veillonella, Chlamydophila pneumoniae, Chlamydia psittaci, Chlamydia trachomatis, Klebsiella pneumoniae, Mycoplasma pneumoniae, Haemophilus influenzae, Streptococcus pneumoniae, Moraxella catarrhalis, Corynebacterium diphtheria, Bordetella pertussis, Coxiella burnetii, Streptococcus pyogenes,* or *Mycobacterium tuberculosis.*

In some embodiments, the bacterium is *Staphylococcus aureus, Pseudomonas aeruginosa, Haemophilus* influenza, MRSA, *S. maltophillia,* or *Burkholderia* (ceno)*cepacia.*

In some embodiments, the bacterium is not *Escherichia coli, Acinetobacter baumannii, Klebsiella pneumoniae, Pseudomonas aeruginosa, Burkhloderia cenocepacia, Burkhloderia multivorans, Enterococcus faecalis* or *Staphylococcus aureus.* In some embodiments, the bacterium is not *Escherichia coli.* In some embodiments, the bacterium is not *Staphylococcus aureus.* In some embodiments, the bacterium is not MRSA or MSSA.

In some embodiments, a bacterial infection is an infection by *Escherichia coli, Acinetobacter baumannii, Klebsiella pneumoniae, Pseudomonas aeruginosa, Burkhloderia cenocepacia, Burkhloderia multivorans, Enterococcus faecalis* or *Staphylococcus aureus* (e.g., MRSA or MSSA).

In some embodiments, the microbial infection is a bacterial infection, and the antimicrobial agent is an antibiotic agent. In some embodiments, the antibiotic agent is a macrolide, peptide, glycopeptide, quinolone or fluoroquinolone, or a pharmaceutically acceptable salt thereof. In some embodiments, the antibiotic agent is pentamidine, erythromycin, dirithromycin, levofloxacin, norfloxacin, ciprofloxacin, enoxacin, moxifloxacin, besifloxacin or polymyxin B, or a pharmaceutically acceptable salt thereof.

In some embodiments, the microbe is a microorganism of the domain Archaea.

In some embodiments, the microbe is a virus. In some embodiments, the virus is an Adenoviridae, Herpesviridae, Poxviridae, Papillomaviridae, Polyomaviridae, Parvoviridae, Reoviridae, Astroviridae, Caliciviridae, Picornaviridae, Coronaviridae, Hepeviridae, Flaviviridae, Togaviridae, Arenaviridae, Bunyaviridae, Filoviridae, Paramyxoviridae, Rhabdoviridae, Orthomyxoviridae, Retroviridae or Hepadnaviridae family member. In some embodiments, the virus is Adenovirus, Herpes simplex virus type 1, Herpes simplex virus type 2, Varicella-zoster virus, Epstein-Barr virus, Human cytomegalovirus, Human herpesvirus type 8, Smallpox, Human papillomavirus, BK virus, JC virus, Parvovirus B19, Rotavirus, Orbivirus, Coltivirus, Banna virus, Human astrovirus, Norwalk virus, coxsackievirus, Hepatitis A virus, Hepatitis B virus, Hepatitis C virus, Hepatitis D virus, Hepatitis E virus, poliovirus, rhinovirus, Severe acute respiratory syndrome virus, yellow fever virus, dengue virus, West Nile virus, TBE virus, Rubella virus, Lassa virus, Crimean-Congo hemorrhagic fever virus, Hantaan virus, Ebola virus, Marburg virus, Measles virus, Mumps virus, Parainfluenza virus, Respiratory syncytial virus, Rabies virus, Influenza virus or Human immunodeficiency virus (HIV).

In some embodiments, the microbial infection is a viral infection, and the antimicrobial agent is an antiviral agent.

In some embodiments, the microbe is an alga.

In some embodiments, the microbe is a fungus. In some embodiments, a fungus is a yeast. In some embodiments, the fungus is *Pneumocystis jirovecii* (formerly known as *Pneumocystis carinii*). In some embodiments, the microbial infection is a *Pneumocystis jirovecii* infection, and the disorder caused by the microbial infection is pneumocystis pneumonia (PCP).

In some embodiments, the fungus is an *Agaricus* species, *Amanita* species, *Armillaria* species, *Aspergillus* species, *Boletus* species, *Caloplaca* species, *Candida* species, *Cladonia* species, *Coprinellus* species, *Coprinopsis* species, *Cortinarius* species, *Cyathus* species, *Deadly fungus* species, *Entoloma* species, *Fusarium* species, *Gymnopilus* species, *Gymnopus* species, *Hebeloma* species, *Hygrocybe* species, *Hygrophorus* species, *Inocybe* species, *Lactarius* species, *Lactifluus* species, *Lecanora* species, *Lepiota* species, *Leucoagaricus* species, *Lichen* species of Montana, *Leccinum* species, *Marasmius* species, *Pleurotus* species, *Mycosphaerella* species, Panaeolus species, *Penicillium* species, *Peniophora* species, *Pertusaria* species, *Phaeocollybia* species, *Pholiota* species, *Pholiotina* species, *Pluteus* species, *Poisonous fungus* species, *Psathyrella* species, *Psilocybe* species, *Psilocybin mushroom* species, *Puccinia* species, *Russula* species, *Scleroderma* species, *Serpula* species, *Trametes* species, *Tricholoma* species, *Tuber* species, or Tulostoma species.

In some embodiments, the microbial infection is a fungal or yeast infection, and the antimicrobial agent is an anti-fungal agent.

In some embodiments, the microbe is a parasite. In some embodiments, a parasite is a protozoan. In some embodiments, a parasite is a multicellular animal parasite. In some embodiments, a parasite is a helminth (e.g., a helminth larva).

In some embodiments, the parasite is an *Acanthamoeba* species, *Balamuthia mandrillaris*, *B. divergens*, *B. bigemina*, *B. equi*, *B. microfti*, *B. duncani*, *Balantidium coli*, a *Blastocystis* species, a *Cryptosporidium* species, *Cyclospora cayetanensis*, *Dientamoeba fragilis*, *Entamoeba histolytica*, *Giardia lamblia*, *Isospora belli*, a *Leishmania* species, *Naegleria fowleri*, *Plasmodium falciparum*, *Plasmodium vivax*, *Plasmodium ovale* curtisi, *Plasmodium ovale* wallikeri, *Plasmodium malariae*, *Plasmodium knowlesi*, *Rhinosporidium seeberi*, *Sarcocystis bovihominis*, *Sarcocystis suihominis*, *Toxoplasma gondii*, *Trichomonas vaginalis*, *Trypanosoma brucei*, *Trypanosoma cruzi*, *Cestoda*, *Taenia multiceps*, *Diphyllobothrium latum*, *Echinococcus granulosus*, *Echinococcus multilocularis*, *E. vogeli*, *E. oligarthrus*, *Hymenolepis nana*, *Hymenolepis diminuta*, *Taenia saginata*, *Taenia solium*, *Bertiella mucronata*, *Bertiella studeri*, *Spirometra erinaceieuropaei*, *Echinostoma echinatum*, *Schistosoma mekongi*, *Opisthorchis viverrini*, *Opisthorchis felineus*, *Clonorchis sinensis*, *Clonorchis sinensis*; *Clonorchis viverrini*, *Fasciolopsis buski*, *Schistosoma mansoni*, *Schistosoma intercalatum*, *Dicrocoelium dendriticum*, *Fasciola hepatica*, *Fasciola gigantica*, *Metagonimus yokogawai*, *Metorchis conjunctus*, *Paragonimus westermani*, *Paragonimus africanus*, *Paragonimus caliensis*, *Paragonimus kellicotti*, *Paragonimus skrjabini*, *Paragonimus uterobilateralis*, *Schistosoma japonicum*, a *Schistosoma* species, *Trichobilharzia regenti*, Schistosomatidae, *Schistosoma haematobium*, *Ancylostoma duodenale*, *Necator americanus*, *Angiostrongylus costaricensis*, an *Anisakis Ascaris* species, *Ascaris lumbricoides*, *Baylisascaris procyonis*, *Brugia malayi*, *Brugia timori*, *Dioctophyme renale*, *Dracunculus medinensis*, *Enterobius vermicularis*, *Enterobius gregorii*, *Gnathostoma spinigerum*, *Gnathostoma hispidum*, *Halicephalobus gingivali*, *Loa loa* filarial, *Mansonella streptocerca*, *Onchocerca volvulus*, *Strongyloides stercoralis*, *Thelazia californiensis*, *Thelazia callipaeda*, *Toxocara canis*, *Toxocara cati*, *Trichinella spiralis*, *Trichinella britovi*, *Trichinella nelsoni*, *Trichinella native*, *Trichuris trichiura*, *Trichuris vulpis*, *Wuchereria bancrofti*, *Archiacanthocephala*, *Moniliformis moniliformis*, *Linguatula serrate*, *Oestroidea*, *Calliphoridae*, *Sarcophagidae*, *Cochliomyia hominivorax*, *Tunga penetrans*, *Dermatobia hominis*, *Pediculus humanus* capitis, *Pediculus humanus humanus*, *Pthirus pubis*, *Demodex folliculorum/brevis/canis*, *Sarcoptes scabiei*, an Arachnida class member, Trombiculidae, *Pulex irritans*, Cimicidae, *Cimex lectularius*, an Ixodidae family member or an Argasidae family member. In some embodiments, the parasite is *Acanthamoeba*.

In some embodiments, the microbial infection is a parasitic infection, and the antimicrobial agent is an anti-parasitic agent.

In some embodiments, the microbial infection is a diabetic foot infection. In some embodiments, the subject has a diabetic foot ulcer. In some embodiments, the microbe exists in a diabetic foot ulcer.

The invention further provides methods for inhibiting the growth of a microbe present in a diabetic foot infection, comprising contacting the microbe with an effective amount of (i) bicarbonate and (ii) an antimicrobial agent disclosed herein. The invention further provides methods for treating a diabetic foot infection, comprising administering to a subject in need thereof an effective amount of (i) bicarbonate and (ii) an antimicrobial agent disclosed herein. The invention further provides methods for treating a diabetic foot ulcer, comprising administering to a subject in need thereof an effective amount of (i) bicarbonate and (ii) an antimicrobial agent disclosed herein.

The invention further provides methods for potentiating the activity of an antimicrobial agent, comprising administering to a subject in need thereof an effective amount of (i) bicarbonate and (ii) an antimicrobial agent, wherein the antimicrobial agent is an antimicrobial agent whose concentration in a cell of a microbe is increased by one or both of (1) a decrease in pH gradient across the microbe's cytoplasmic membrane; and (2) an increase in the microbe's cytoplasmic membrane potential; or wherein the antimicrobial agent decreases the microbe's cytoplasmic membrane potential.

The invention further provides compositions comprising sodium bicarbonate and an antimicrobial agent, wherein the antimicrobial agent's concentration in a cell of a microbe is increased by one or both of (1) a decrease in pH gradient across the microbe's cytoplasmic membrane; and (2) an increase in the microbe's cytoplasmic membrane potential; or wherein the antimicrobial agent decreases the microbe's cytoplasmic membrane potential.

In some embodiments, the methods of the invention comprise administering to a subject in need thereof an effective amount of (i) bicarbonate and (ii) an antimicrobial agent, wherein the antimicrobial agent is an antimicrobial agent whose concentration in a cell of the microbe is increased as a result of one or both of (1) decrease in pH gradient across the microbe's cytoplasmic membrane; and (2) increase in the microbe's cytoplasmic membrane potential; or wherein the antimicrobial agent decreases the microbe's cytoplasmic membrane potential; and wherein the antimicrobial agent is not an aminoglycoside.

In some embodiments, the methods for treating or preventing a microbial infection or a disorder caused by a microbial infection comprise administering to a subject in need thereof an effective amount of (i) bicarbonate and (ii) an antimicrobial agent, wherein the microbial infection is by a microbe, and wherein the antimicrobial agent is a cationic antimicrobial agent, antimicrobial agent that is an energy dependent efflux substrate, antimicrobial agent for which entry depends on membrane potential, or an antimicrobial agent that disrupts membrane potential as a primary mechanism of action.

In some embodiments of the methods of the invention, the bicarbonate and antimicrobial agent decrease the microbe's growth. In some embodiments, the bicarbonate and antimicrobial agent decrease the microbe's growth by at least 10-fold compared to the microbe's growth in response to the antimicrobial agent in the absence of bicarbonate. In some embodiments, the bicarbonate and antimicrobial agent decrease the microbe's growth by at least 20-fold compared to the microbe's growth in response to the antimicrobial agent in the absence of bicarbonate. In some embodiments, the bicarbonate and antimicrobial agent decrease the microbe's growth by at least 30-fold compared to the microbe's growth in response to the antimicrobial agent in the absence of bicarbonate.

In some embodiments, the bicarbonate and antimicrobial agent increase the microbe's growth. In some embodiments, the bicarbonate and antimicrobial agent increase the microbe's growth by at least 10-fold compared to the microbe's growth in response to the antimicrobial agent in the absence of bicarbonate.

In some embodiments of the methods of the invention, the bicarbonate or antimicrobial agent inhibits growth of a microbe. In some embodiments of the methods of the invention, the bicarbonate and antimicrobial agent inhibit growth of a microbe.

In some embodiments of the methods of the invention, a microbe is present on a substrate. In some embodiments, the substrate is glass, metal, plastic, latex, ceramic, cement, wood, grout, stone or biological tissue. In some embodiments, the biological tissue is ex vivo. In some embodiments, the biological tissue is in vitro. In some embodiments, the microbe is present on or in a surgical instrument. In some embodiments, the microbe is present on or in a catheter, an implant, a stent or a surgical mesh.

In some embodiments, a subject is infected with the microbe. In some embodiments, the subject is a mammal. In some embodiments, the subject is a human. In some embodiments, the subject has a microbial infection. In some embodiments, the microbial infection is a systemic, pulmonary, lung, otic, oral, nasal, sinus, ophthalmic, intraocular, dermal, cardiovascular, kidney, urinary, gastrointestinal, rectal, vaginal or neurological infection. In some embodiments, the microbial infection is an infection of a mucous membrane.

Bicarbonate

In some embodiments, the bicarbonate potentiates antimicrobial activity by increasing the effective intracellular levels of various antimicrobial agents or enhancing their ability to collapse PMF.

In some embodiments, the bicarbonate is potassium, lithium, calcium, magnesium, sodium, ammonium or zinc bicarbonate. In some embodiments, the bicarbonate is sodium bicarbonate or ammonium bicarbonate. In some embodiments, the bicarbonate is sodium bicarbonate.

In some embodiments, the dosage or amount of the bicarbonate is an amount that provides a physiological concentration of bicarbonate. In some embodiments, the dosage or amount of the bicarbonate is about 25 mM of bicarbonate. In some embodiments, the bicarbonate is present in a composition. In some embodiments, the composition is an aqueous composition. In some embodiments, the composition comprises bicarbonate at a concentration of about 1 mM to about 900 mM. In some embodiments, the composition comprises bicarbonate at a concentration of about 1 mM to about 150 mM bicarbonate, about 25 mM to about 100 mM bicarbonate, about 30 mM to about 100 mM bicarbonate, or about 20 mM to about 50 mM bicarbonate. In some embodiments, the composition comprises bicarbonate at a concentration of about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM or about 150 mM. In some embodiments, the composition comprises bicarbonate at a concentration of about 175 mM to about 900 mM. In some embodiments, the composition comprises bicarbonate at a concentration of about 175 mM to about 225 mM, about 200 mM to about 300 mM, about 300 mM to about 400 mM, about 400 mM to about 500 mM, about 500 mM to about 600 mM, about 600 mM to about 700 mM, about 700 mM to about 800 mM or about 800 mM to about 900 mM. Where the composition comprises bicarbonate at a particular M or mM concentration, the M or mM concentration is moles or millimoles, respectively, of bicarbonate per liter of water. In some embodiments, the composition comprises bicarbonate in an amount of about 0.01 wt % to about 8.4 wt % of the composition. In some embodiments, the composition comprises bicarbonate in an amount of about 0.01 wt % to about 1.0 wt %, or about 0.20 wt % to about 0.5 wt % of the composition. In some embodiments, the composition comprises bicarbonate in a composition in an amount of about 1.75 wt % to about 8.4 wt % of the composition.

In some embodiments, the effective amount or dosage of bicarbonate is about 0.01 mg to about 1 mg per kg of body weight of the subject. In some embodiments, the compositions of the invention comprise about 0.01 mg to about 1 mg of bicarbonate.

In some embodiments, the bicarbonate is a component of a buffer.

Methods of the Invention

The invention provides methods for inhibiting growth of a microbe, comprising contacting the microbe with an effective amount of (i) bicarbonate and (ii) an antimicrobial agent. In some embodiments, the microbe is a virus, bacterium, fungus or parasite. In some embodiments, the antimicrobial agent is an antiseptic agent, an antibiotic agent, an innate immunity factor, an antiviral agent, an anti-fungal agent or an anti-parasitic agent.

Provided herein are methods for inhibiting growth of a microbe, comprising contacting the microbe with an effective amount of (i) bicarbonate and (ii) an antimicrobial agent, wherein the antimicrobial agent is benzamide, furadinozoline, gramicidin, hygromycin B, nadifloxacin, nisin, pleuromutilin, thiostrepton, triclosan, bromocriptine mesylate, aminacrine, acrisorcin, mitoxantrone hydrochloride, amsacrine, homidium bromide, sulfamethazine, sulfaphenazole, chloroxine, acriflavinium hydrochloride, diminazene (e.g., diminazene aceturate or diminazene diaceturate), sulfapyridine, ropinirole hydrochloride, sulfaguanidine, metergoline, closantel, sulfameter, cefalonium, sulfadoxine, doxorubicin, cetrimonium bromide, phenylmercuric acetate, dequalinium chloride, clioquinol, amiodarone hydrochloride, monobenzone, proflavine hemisulfate, nisoldipine, methylbenzethonium chloride, cephalothin sodium, fluvoxamine maleate, tacrine hydrochloride, guanabenz acetate, ramoplanin, orlistat, clofoctol, puromycin hydrochloride, broxaldine, sanguinarine sulfate, dihydrostreptomycin sulfate, octisalate, ethacridine lactate, bithionate sodium, montelukast sodium, oltipraz, ipratropium bromide, ipriflavone, enalapril maleate, flopropione, sulfaquinoxaline sodium, bisoctrizole, azathioprine, enalaprilat, exalamide, benzalkonium chloride, benzethonium chloride, cetrimonium bromide, cetylpyridinium chloride, chlorhexidine, dibrompropamidine diisetionate, hexadecyltrimethylammonium bromide, p-hydroxybenzoate, polyhexanide or a polyvinylpyrrolidone iodine complex, or a pharmaceutically acceptable salt thereof.

Provided herein are methods for inhibiting growth of a microbe, comprising contacting the microbe with an effective amount of (i) bicarbonate and (ii) an antimicrobial agent, wherein the bicarbonate is sodium bicarbonate and the antimicrobial agent is diminazene (e.g., diminazene aceturate or diminazene diaceturate), cetylpyridinium chloride, dequalinium chloride, aminacrine, amsacrine or mitoxanthrone, or a pharmaceutically acceptable salt thereof. The use of any one of these antimicrobial agents and sodium bicarbonate for inhibiting growth of a microbe is part of the invention.

Also provided herein are methods for inhibiting growth of a microbe, comprising contacting the microbe with an effective amount of (i) bicarbonate and (ii) an antimicrobial agent, wherein the antimicrobial agent is amikacin, azithromycin, clarithromycin, clindamycin, polymyxin B, colistin, daptomycin, fusidic acid, gatifloxacin, lincomycin, lomefloxacin, metronidazole, mupirocin, roxithromycin, sparfloxacin, spiramycin, streptomycin, teicoplanin, telithromycin or tobramycin, or a pharmaceutically acceptable salt thereof and wherein the bicarbonate is present in a composition (a) at a concentration of about 1 mM to about 900 mM; or (b) in an amount of about 0.01 wt % to about 8.4 wt % of the composition.

Also provided herein are methods for inhibiting growth of a microbe, comprising contacting the microbe with an effective amount of (i) bicarbonate and (ii) an antimicrobial agent, wherein the bicarbonate is sodium bicarbonate and the antimicrobial agent is azithromycin, clarithromycin, roxithromycin, spiramycin, telithromycin, moxifloxacin, besifloxacin, streptomycin, spectinomycin, polymyxin B or pentamidine (e.g., pentamidine isethionate), or a pharmaceutically acceptable salt thereof and (a) wherein the bicarbonate is present in the composition at a concentration of about 1 mM to about 900 mM; or (b) wherein the bicarbonate is present in the composition in an amount of about 0.01 wt % to about 8.4 wt % of the composition. The use of any one of these antimicrobial agents and sodium bicarbonate for inhibiting growth of a microbe is part of the invention. In some embodiments, the bicarbonate is present at a concentration of about 175 mM to about 900 mM. In some embodiments, the bicarbonate is present at a concentration of about 175 mM to about 225 mM, about 200 mM to about 300 mM, about 300 mM to about 400 mM, about 400 mM to about 500 mM, about 500 mM to about 600 mM, about 600 mM to about 700 mM, about 700 mM to about 800 mM or about 800 mM to about 900 mM.

Further provided herein are methods for treating or preventing a microbial infection, comprising administering to a subject in need thereof an effective amount of (i) bicarbonate and (ii) an antimicrobial agent, wherein the antimicrobial agent is benzamide, furadinozoline, gramicidin, hygromycin B, nadifloxacin, nisin, pleuromutilin, thiostrepton, triclosan, bromocriptine mesylate, aminacrine, acrisorcin, mitoxantrone hydrochloride, amsacrine, homidium bromide, sulfamethazine, sulfaphenazole, chloroxine, acriflavinium hydrochloride, diminazene (e.g., diminazene aceturate or diminazene diaceturate), sulfapyridine, ropinirole hydrochloride, sulfaguanidine, metergoline, closantel, sulfameter, cefalonium, sulfadoxine, doxorubicin, cetrimonium bromide, phenylmercuric acetate, dequalinium chloride, clioquinol, amiodarone hydrochloride, monobenzone, proflavine hemi sulfate, nisoldipine, methylbenzethonium chloride, cephalothin sodium, fluvoxamine maleate, tacrine hydrochloride, guanabenz acetate, ramoplanin, orlistat, clofoctol, puromycin hydrochloride, broxaldine, sanguinarine sulfate, dihydrostreptomycin sulfate, octisalate, ethacridine lactate, bithionate sodium, montelukast sodium, oltipraz, ipratropium bromide, ipriflavone, enalapril maleate, flopropione, sulfaquinoxaline sodium, bisoctrizole, azathioprine, enalaprilat, exalamide, benzalkonium chloride, benzethonium chloride, cetrimonium bromide, cetylpyridinium chloride, chlorhexidine, dibrompropamidine diisetionate, hexadecyltrimethylammonium bromide, p-hydroxybenzoate, polyhexanide or a polyvinylpyrrolidone iodine complex, or a pharmaceutically acceptable salt thereof.

Provided herein are methods for treating or preventing a microbial infection, comprising administering to a subject in need thereof an effective amount of (i) bicarbonate and (ii) an antimicrobial agent, wherein the bicarbonate is sodium bicarbonate and the antimicrobial agent is diminazene (e.g., diminazene aceturate or diminazene diaceturate), cetylpyridinium chloride, dequalinium chloride, aminacrine, amsacrine or mitoxanthrone, or a pharmaceutically acceptable salt thereof. The use of any one of these antimicrobial agents and sodium bicarbonate for treating or preventing a microbial infection is part of the invention.

Further provided herein are methods for treating or preventing a microbial infection, comprising administering to a subject in need thereof an effective amount of (i) bicarbonate and (ii) an antimicrobial agent, wherein the antimicrobial agent is amikacin, azithromycin, clarithromycin, clindamycin, polymyxin B, colistin, daptomycin, fusidic acid, gatifloxacin, lincomycin, lomefloxacin, metronidazole, mupirocin, roxithromycin, sparfloxacin, spiramycin, streptomycin, teicoplanin, telithromycin or tobramycin, or a pharmaceutically acceptable salt thereof; and wherein the bicarbonate is present in a composition (a) at a concentration of about 1 mM to about 900 mM; or (b) in an amount of about 0.01 wt % to about 8.4 wt % of the composition.

Also provided herein are methods for treating or preventing a microbial infection, comprising administering to a subject in need thereof an effective amount of (i) bicarbonate and (ii) an antimicrobial agent, wherein the bicarbonate is sodium bicarbonate and the antimicrobial agent is azithromycin, clarithromycin, roxithromycin, spiramycin, telithromycin, moxifloxacin, besifloxacin, streptomycin, spectinomycin, polymyxin B or pentamidine (e.g., pentamidine isethionate), or a pharmaceutically acceptable salt thereof; and (a) wherein the bicarbonate is present in the composition at a concentration of about 1 mM to about 900 mM; or (b) wherein the bicarbonate is present in the composition in an amount of about 0.01 wt % to about 8.4 wt % of the composition. The use of any one of these antimicrobial agents and sodium bicarbonate for inhibiting growth of a microbe is part of the invention. In some embodiments, the bicarbonate is present in the composition at a concentration of about 175 mM to about 900 mM. In some embodiments, the bicarbonate is present in the composition at a concentration of about 175 mM to about 225 mM, about 200 mM to about 300 mM, about 300 mM to about 400 mM, about 400 mM to about 500 mM, about 500 mM to about 600 mM, about 600 mM to about 700 mM, about 700 mM to about 800 mM or about 800 mM to about 900 mM.

In some embodiments, provided herein are methods for inhibiting growth of a microbe, comprising contacting the microbe with an effective amount of (i) bicarbonate and (ii) an antimicrobial agent, wherein the microbe is:

(a) a rod-shaped bacterium, a sphere-shaped bacterium, a spiral-shaped bacterium, a filamentous bacterium, a pleomorphic bacterium or a rectangular bacterium;

(b) a facultative anaerobe, an obligate aerobe or an obligate anaerobe;

(c) a Gram positive bacterium or a Gram negative bacterium; or (d) a species of *Acetobacter, Acinetobacter, Actinomyces, Aerococcus, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Escherichia, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum, Spirochaetes, Staphylococcus, Stenotrophomonas, Streptobacillus, Streptococcus, Tetragenococcus, Treponema, Vibrio, Viridans, Wolbachia* or *Yersinia*.

Provided herein are methods for inhibiting growth of *Staphylococcus aureus*, comprising contacting the *Staphylococcus aureus* with an effective amount of (i) bicarbonate and (ii) pentamidine or a pharmaceutically acceptable salt thereof.

Additionally provided herein are methods for treating or preventing a microbial infection, comprising administering to a subject in need thereof an effective amount of (i) bicarbonate and (ii) an antimicrobial agent, wherein the microbial infection is an infection by a virus, a bacterium, a fungus or a parasite; and wherein the bacterium is:

(a) a spiral-shaped bacterium, a filamentous bacterium, a pleomorphic bacterium or a rectangular bacterium;

(b) an obligate aerobe or an obligate anaerobe;

(c) a Gram positive rod-shaped bacterium;

(d) a Gram negative sphere-shaped bacterium;

(e) a species of *Acinetobacter, Actinomyces, Aerococcus, Agrobacterium, Anaplasma, Azorhizobium, Azotobacter, Bacillus, Bacteroides, Bartonella, Bordetella, Borrelia, Brucella, Burkholderia, Calymmatobacterium, Campylobacter, Chlamydia, Chlamydophila, Clostridium, Corynebacterium, Coxiella, Ehrlichia, Enterobacter, Enterococcus, Francisella, Fusobacterium, Gardnerella, Haemophilus, Helicobacter, Klebsiella, Lactobacillus, Lactococcus, Legionella, Listeria, Methanobacterium, Microbacterium, Micrococcus, Moraxella, Mycobacterium, Mycoplasma, Neisseria, Pasteurella, Pediococcus, Peptostreptococcus, Porphyromonas, Prevotella, Pseudomonas, Rhizobium, Rickettsia, Rochalimaea, Rothia, Salmonella, Serratia, Shigella, Sarcina, Spirillum, Spirochaetes, Stenotrophomonas, Streptobacillus, Streptococcus, Tetragenococcus, Treponema, Vibrio, Viridans, Wolbachia* or *Yersinia*; or (f) *Staphylococcus epidermidis*.

Further provided herein are methods for inhibiting growth of a microbe, comprising contacting the microbe with an effective amount of (i) bicarbonate and (ii) an antimicrobial agent, wherein the antimicrobial agent is an antiviral agent, an anti-fungal agent, an anti-parasitic agent, an antibiotic agent, or an innate immunity factor; and wherein the antibiotic agent is a macrolide, a quinolone, a rifampin or a fluoroquinolone, or a pharmaceutically acceptable salt thereof.

Further provided herein are methods for treating or preventing a microbial infection, comprising administering to a subject in need thereof an effective amount of (i) bicarbonate and (ii) an antimicrobial agent;

wherein the microbial infection is an infection by a virus, a bacterium, a fungus or a parasite, wherein the antimicrobial agent is an antiviral agent, an anti-fungal agent, an anti-parasitic agent, an antibiotic agent, or an innate immunity factor; and wherein the antibiotic agent is a macrolide, a quinolone, a rifampin or a fluoroquinolone, or a pharmaceutically acceptable salt thereof.

Further provided herein are methods for treating or preventing a microbial infection, comprising administering to a subject in need thereof an effective amount of (i) bicarbonate and (ii) an antimicrobial agent, wherein the microbial infection is an infection by a bacterium, and wherein the bacterium is *Acetobacter aurantius, Acinetobacter baumannii, Actinomyces israelii, Aerococcus viridans, Agrobacterium radiobacter, Agrobacterium tumefaciens, Anaplasma phagocytophilum, Azorhizobium caulinodans, Azotobacter vinelandii, Bacillus anthracis, Bacillus brevis, Bacillus cereus, Bacillus fusiformis, Bacillus licheniformis, Bacillus megaterium, Bacillus mycoides, Bacillus stearothermophilus, Bacillus subtilis, Bacillus thuringiensis, Bacteroides fragilis, Bacteroides gingivalis, Bacteroides melaninogenicus, Bartonella henselae, Bartonella quintana, Bordetella bronchiseptica, Bordetella pertussis, Borrelia burgdorferi. Brucella abortus, Brucella melitensis, Brucella suis, Burkholderia mallei, Burkholderia pseudomallei, Burkholderia cepacia, Calymmatobacterium granulomatis, Campylobacter coli, Campylobacter fetus, Campylobacter jejuni, Campylobacter pylori, Chlamydia trachomatis, Chlamydophila pneumoniae, Chlamydophila psittaci, Clostridium botulinum, Clostridium difficile, Clostridium perfringens, Clostridium tetani, Corynebacterium diphtheriae, Corynebacterium fusiforme*, CDC coryneform group G, *Coxiella burnetii, Ehrlichia chaffeensis, Enterobacter cloacae, Enterococcus avium, Enterococcus durans, Enterococcus faecalis, Enterococcus faecium,*

*Enterococcus gallinarum, Enterococcus maloratus, Escherichia coli, Francisella tularensis, Fusobacterium nucleatum, Gardnerella vaginalis, Haemophilus ducreyi, Haemophilus influenzae, Haemophilus parainfluenzae, Haemophilus pertussis, Haemophilus vaginalis, Helicobacter pylori, Klebsiella pneumoniae, Lactobacillus acidophilus, Lactobacillus bulgaricus, Lactobacillus casei, Lactococcus lactis, Legionella pneumophila, Listeria monocytogenes, Methanobacterium extroquens, Microbacterium multiforme, Micrococcus luteus, Moraxella catarrhalis, Mycobacterium avium, Mycobacterium bovis, Mycobacterium diphtheriae, Mycobacterium intracellulare, Mycobacterium leprae, Mycobacterium lepraemurium, Mycobacterium phlei, Mycobacterium smegmatis, Mycobacterium tuberculosis, Mycoplasma fermentans, Mycoplasma genitalium, Mycoplasma hominis, Mycoplasma penetrans, Mycoplasma pneumoniae, Neisseria gonorrhoeae, Neisseria meningitidis, Pasteurella multocida, Pasteurella tularensis, Peptostreptococcus, Porphyromonas gingivalis, Prevotella melaninogenica, Pseudomonas aeruginosa, Rhizobium radiobacter, Rickettsia* prow *azekii, Rickettsia psittaci, Rickettsia quintana, Rickettsia rickettsii, Rickettsia trachomas, Rochalimaea henselae, Rochalimaea quintana, Rothia dentocariosa, Salmonella enteritidis, Salmonella typhi, Salmonella typhimurium, Serratia marcescens, Shigella dysenteriae, Spirillum volutans, Staphylococcus aureus, Staphylococcus epidermidis, Stenotrophomonas maltophilia, Streptococcus agalactiae, Streptococcus avium, Streptococcus bovis, Streptococcus cricetus, Streptococcus faceium, Streptococcus faecalis, Streptococcus ferus, Streptococcus gallinarum, Streptococcus lactis, Streptococcus mitior, Streptococcus mitis, Streptococcus mutans, Streptococcus oralis, Streptococcus pneumoniae, Streptococcus pyogenes, Streptococcus rattus, Streptococcus salivarius, Streptococcus sanguis, Streptococcus sobrinus, Treponema pallidum, Treponema denticola, Vibrio cholerae, Vibrio comma, Vibrio parahaemolyticus, Vibrio vulnificus, Viridans streptococci, Wolbachia, Yersinia enterocolitica, Yersinia pestis* or *Yersinia pseudotuberculosis.*

Also provided herein are methods for treating or preventing a microbial infection, comprising administering to a subject in need thereof an effective amount of (i) bicarbonate and (ii) an antimicrobial agent, wherein the microbial infection is an infection by a Gram negative bacterium, and wherein the antimicrobial agent is azithromycin. In some embodiments, the Gram negative bacterium is *Pseudomonas aeruginosa.*

Further provided herein are methods for treating or preventing a microbial infection, comprising administering to a subject in need thereof an effective amount of (i) bicarbonate and (ii) an antimicrobial agent, wherein the microbial infection is an infection by a bacterium, and wherein the bacterium is *Staphylococcus aureus*, MRSA, *Staphylococcus epidermidis, Streptococcus pneumoniae, Haemophilus influenza, Pseudomonas aeruginosa, Chlamydia trachomatis, Moraxella* sp., *Neisseria gonorrhoeae, Corynebacterium diphtheriae*, Group A Streptococci, *Streptococcus pyogenes, Streptococcus agalactiae, Klebsiella pneumoniae, Enterobacter aerogene, Proteus vulgaris, Mycobacterium leprae, Propionibacterium acnes, Erysipelothrix rhusiopathiae, Corynebacterium minutissimum, Corynebacterium tenuis, Brevibacterium, Mycobacterium tuberculosis, Mycobacterium marinum,* or *Mycobacterium ulcerans*. In some embodiments, the microbial infection is a dermal infection.

Also provided herein are methods for treating or preventing a microbial infection, comprising administering to a subject in need thereof an effective amount of (i) bicarbonate and (ii) an antimicrobial agent, wherein the microbial infection is an infection by a bacterium, and wherein the bacterium is *Staphylococcus aureus*, MRSA, *Staphylococcus epidermidis, Streptococcus pneumoniae, Haemophilus influenza, Pseudomonas aeruginosa, Chlamydia trachomatis, Moraxella* sp., *Neisseria gonorrhoeae,* or *Corynebacterium* diphtherias. In some embodiments, the microbial infection is an ophthalmic infection.

Further provided herein are methods for treating or preventing a microbial infection, comprising administering to a subject in need thereof an effective amount of (i) bicarbonate and (ii) an antimicrobial agent, wherein the microbial infection is an infection by a bacterium, and wherein the bacterium is *Pseudomonas aeruginosa, Chlamydophila pneumoniae, Prevotella* sp., *Mycobacterium, Moraxella catarrhalis, Stenotrophomonas maltophilia, Mycoplasma pneumoniae, Mycobacterium abscessus, Veillonella, Chlamydophila pneumoniae, Chlamydia psittaci, Chlamydia trachomatis, Klebsiella pneumoniae, Mycoplasma pneumoniae, Haemophilus influenzae, Streptococcus pneumoniae, Moraxella catarrhalis, Corynebacterium diphtheria, Bordetella pertussis, Coxiella burnetii, Streptococcus pyogenes,* or *Mycobacterium tuberculosis*. In some embodiments, the microbial infection is a lung infection.

Also provided herein are methods for treating or preventing a microbial infection, comprising administering to a subject in need thereof an effective amount of (i) bicarbonate and (ii) an antimicrobial agent, wherein the microbial infection is an infection by a parasite, and wherein the parasite is *Acanthamoeba*. In some embodiments, the microbial infection is an ophthalmic infection.

Further provided herein are methods of modulating a microbe's response to an antimicrobial agent. The methods comprise contacting a microbe with an antimicrobial agent in the presence of bicarbonate, whereby the bicarbonate modulates the microbe's response to the antimicrobial agent. In some embodiments, the bicarbonate potentiates the microbe's response to the antimicrobial agent, resulting in an increased response. In some embodiments, the antimicrobial agent is an innate immunity factor or a macrolide, peptide, glycopeptide, quinolone, rifampin, fluoroquinolone, an antifungal agent or aminoglycoside antibiotic agent. In some embodiments, the antimicrobial agent is not an aminoglycoside.

In some embodiments, a microbe is resistant to an antimicrobial agent in the absence of bicarbonate. In some embodiments, the microbe is more resistant to an antimicrobial agent in the absence of bicarbonate than in the presence of bicarbonate. In some embodiments, the microbe is sensitive to the antimicrobial agent in the presence of bicarbonate. In some embodiments, the microbe is more sensitive to the antimicrobial agent in the presence of bicarbonate than in the absence of bicarbonate.

In some embodiments, a microbe's growth is reduced by the antimicrobial agent in the presence of the bicarbonate to a greater extent than by the antimicrobial agent in the absence of the bicarbonate. In some embodiments, a microbe's growth is reduced by the antimicrobial agent in the presence of the bicarbonate by at least 2-fold, at least 4-fold, at least 5-fold, at least 8-fold, at least 10-fold, at least 15-fold, at least 20-fold, or at least 30-fold greater than by the antimicrobial agent in the absence of the bicarbonate. In some embodiments, a microbe's growth is reduced by the antimicrobial agent in the presence of the bicarbonate to 75%, to 50%, to 25%, to 20%, to 12.5%, to 10% or to 5% of the microbe's growth in the presence of the antimicrobial agent and in the absence of the bicarbonate.

In some embodiments, the presence of bicarbonate changes (e.g., decreases) the MIC of the antimicrobial agent relative to the MIC of the antimicrobial agent in the absence of the bicarbonate by at least 2-fold, at least 4-fold, at least 5-fold, at least 8-fold, at least 10-fold, at least 15-fold, at least 20-fold, or at least 30-fold. In some embodiments, MIC is the lowest detectable concentration of the antimicrobial agent that inhibits microbial growth under standard growth conditions. In some embodiments, $MIC_x$ is the lowest concentration of an antimicrobial agent that inhibits microbial growth x % of a population of microbes or of x/100 strains of a microbe.

In some embodiments, the MIC of the antimicrobial agent is determined in MHB media and compared to the MIC in MHB supplemented with a physiological concentration of sodium bicarbonate (25 mM). A fold shift in MIC is a comparison of the MIC in MHB in the presence of sodium carbonate to the MIC in MHB in the absence of sodium bicarbonate. A positive fold shift greater than +1 in MIC indicates enhancement of antimicrobial activity in the presence of sodium bicarbonate. A negative fold shift in MIC indicates suppression of antimicrobial activity in the presence of sodium bicarbonate. For example, a fold shift of +2 indicates that the MIC of an antimicrobial agent in MHB in the presence of sodium bicarbonate is half the MIC of the same antimicrobial agent in MHB in the absence of sodium bicarbonate. A fold shift of −2 indicates that the MIC of an antimicrobial agent in MHB in the presence of sodium bicarbonate is twice the MIC of the same antimicrobial agent in MHB in the absence of sodium bicarbonate. A fold shift of +1 indicates no difference between the MIC in MHB in the presence of sodium bicarbonate compared to the MIC in MHB in the absence of sodium bicarbonate.

In some embodiments, the methods of the invention are useful for treating or preventing a *Staphylococcus aureus* infection, comprising administering to a subject in need thereof an effective amount of (i) bicarbonate and (ii) pentamidine or a pharmaceutically acceptable salt thereof.

In some embodiments, the methods described herein comprise administering to a subject in need thereof an effective amount of (i) bicarbonate and (ii) indolicidin, bactenesin, defensin, alpha-defensin, a bile salt, lysozyme, protegrin, or hyaluronic acid, or a pharmaceutically acceptable salt thereof.

The present invention provides methods for potentiating an antimicrobial agent comprising administering to a subject in need thereof an effective amount of (i) bicarbonate and (ii) the antimicrobial agent, wherein the antimicrobial agent is an antimicrobial agent whose concentration in a cell of the microbe is increased by one or both of (1) decrease in pH gradient across the microbe's cytoplasmic membrane; and (2) increase in the microbe's cytoplasmic membrane potential. In some embodiments, the antimicrobial agent is a macrolide, peptide, glycopeptide, quinolone, fluoroquinolone, rifampin or innate immunity factor, or a pharmaceutically acceptable salt thereof. In some embodiments, the antimicrobial agent is not an aminoglycoside or a pharmaceutically acceptable salt thereof.

In some embodiments, the bicarbonate and the antimicrobial agent are present in the same composition. In some embodiments, the bicarbonate and the antimicrobial agent are not present in the same composition. In some embodiments, the bicarbonate is present in a first composition and the antimicrobial agent is present in a second composition. In some embodiments, the same composition, the first composition or the second composition is an ex-vivo composition. In some embodiments, the ex-vivo composition is a synthetic composition. In some embodiments, the same composition, the first composition or the second composition is a solution, a gel, a cream, a lotion, a suspension, an aerosol, a nebulized spray or an ointment. In some embodiments, the same composition, the first composition or the second composition is a solution of one or both of bicarbonate and an antimicrobial agent. In some embodiments, the same composition, the first composition or the second composition is a suspension of one or both of bicarbonate and an antimicrobial agent. In some embodiments, the bicarbonate and the antimicrobial agent are present in the same composition, the composition is a suspension, and the antimicrobial agent is suspended in the suspension. In some embodiments, the bicarbonate and the antimicrobial agent are present in the same composition, the composition is a suspension, and the bicarbonate is suspended in the suspension. In some embodiments, the bicarbonate and the antimicrobial agent are present in the same composition, the composition is a suspension, and the bicarbonate and antimicrobial agent are suspended in the suspension.

In some embodiments, the dosage or amount of the bicarbonate present in the composition is an amount that provides a physiological concentration of bicarbonate. In some embodiments, the bicarbonate is present in the composition at a concentration of about 25 mM. In some embodiments, the bicarbonate is present in the composition at a concentration of about 1 mM to about 900 mM. In some embodiments, the bicarbonate is present in the composition at a concentration of about 1 mM to about 150 mM, about 25 mM to about 100 mM, about 30 mM to about 100 mM, or about 20 mM to about 50 mM. In some embodiments, the bicarbonate is present in the composition at a concentration of about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM or about 150 mM. In some embodiments, the bicarbonate is present in the composition at a concentration of about 175 mM to about 900 mM. In some embodiments, the bicarbonate is present in the composition at a concentration of about 175 mM to about 225 mM, about 200 mM to about 300 mM, about 300 mM to about 400 mM, about 400 mM to about 500 mM, about 500 mM to about 600 mM, about 600 mM to about 700 mM, about 700 mM to about 800 mM or about 800 mM to about 900 mM.

In some embodiments, the bicarbonate is present in the composition in an amount of about 0.01 wt % to about 8.4 wt % of the composition. In some embodiments, the bicarbonate is present in the composition in an amount of about 0.01 wt % to about 1.0 wt %, or about 0.20 wt % to about 0.5 wt % of the composition. In some embodiments, the bicarbonate is present in the composition in an amount of about 1.75 wt % to about 8.4 wt % of the composition.

In some embodiments, the effective amount or dosage of the antimicrobial agent is about 25 mg, about 50 mg, about 75 mg, about 100 mg, about 150 mg, about 200 mg, about 250 mg, about 300 mg, about 400 mg, about 500 mg, about 600 mg, about 700 mg, about 800 mg or about 900 mg. In some embodiments, the effective amount or dosage of the antimicrobial agent is about 0.25 mg to about 1.0 mg per kg of body weight of the subject (mg/kg). In some embodiments, the effective amount or dosage of the antimicrobial agent is about 0.5 to about 1.0 mg/kg, about 0.75 to about 1.5 mg/kg, about 1.0 to about 2.0 mg/kg, about 1.5 to about 3.0 mg/kg, about 2.0 to about 5.0 mg/kg, about 5.0 to about 10.0 mg/kg, about 10.0 to about 15.0 mg/kg, about 15.0 to about 20.0 mg/kg, about 20.0 to about 25.0 mg/kg, or about 25.0 to about 50.0 mg/kg. In some embodiments, the antimicrobial agent is polymyxin B, colistin, azithromycin or diminazene, or a pharmaceutically acceptable salt thereof.

In some embodiments, the invention provides methods for inhibiting growth of a microbe, comprising contacting the microbe with an effective amount of (i) bicarbonate and (ii) an antimicrobial agent, wherein: the bicarbonate is present in a composition (a) at a concentration of about 1 millimoles/L to about 900 millimoles/L of the composition or (b) in an amount of about 0.01 wt % to about 8.4 wt % of the composition; and the antimicrobial agent is present in a composition (a') in an amount of about 0.01 mg to about 25.0 mg of antimicrobial agent/mL of the composition or (b') in an amount of about 0.01 mg to about 25.0 mg antimicrobial agent/g of composition.

In some embodiments, the invention provides methods for treating or preventing a microbial infection, comprising administering to a subject in need thereof an effective amount of (i) bicarbonate and (ii) an antimicrobial agent, wherein: the bicarbonate is present in a composition (a) at a concentration of about 1 millimoles/L to about 900 millimoles/L of the composition or (b) in an amount of about 0.01 wt % to about 8.4 wt % of the composition; and the antimicrobial agent is present in a composition (a') in an amount of about 0.01 mg to about 25.0 mg of antimicrobial agent/mL of the composition or (b') in an amount of about 0.01 mg to about 25.0 mg antimicrobial agent/g of composition.

In some embodiments, the antimicrobial agent is present in a composition in an amount of about 0.01 mg antimicrobial agent/mL of composition; about 0.02 mg antimicrobial agent/mL of composition; about 0.03 mg antimicrobial agent/mL of composition; about 0.04 mg antimicrobial agent/mL of composition; about 0.05 mg antimicrobial agent/mL of composition; about 0.1 mg antimicrobial agent/mL of composition; about 0.2 mg antimicrobial agent/mL of composition; about 0.3 mg antimicrobial agent/mL of composition; about 0.4 mg antimicrobial agent/mL of composition; about 0.5 mg antimicrobial agent/mL of composition; about 1 mg antimicrobial agent/mL of composition; about 1.5 mg antimicrobial agent/mL of composition; about 2.0 mg antimicrobial agent/mL of composition; about 3.0 mg antimicrobial agent/mL of composition; about 4.0 mg antimicrobial agent/mL of composition; about 5.0 mg antimicrobial agent/mL of composition; about 6.0 mg antimicrobial agent/mL of composition; about 7.0 mg antimicrobial agent/mL of composition; about 8.0 mg antimicrobial agent/mL of composition; about 9.0 mg antimicrobial agent/mL of composition; about 10.0 mg antimicrobial agent/mL of composition; about 12.5 mg antimicrobial agent/mL of composition; about 15.0 mg antimicrobial agent/mL of composition; about 20.0 mg antimicrobial agent/mL of composition; or about 25.0 mg antimicrobial agent/mL of composition.

In some embodiments, the antimicrobial agent is present in a composition in an amount of about 0.01 mg antimicrobial agent/g of composition; about 0.02 mg antimicrobial agent/g of composition; about 0.03 mg antimicrobial agent/g of composition; about 0.04 mg antimicrobial agent/g of composition; about 0.05 mg antimicrobial agent/g of composition; about 0.1 mg antimicrobial agent/g of composition; about 0.2 mg antimicrobial agent/g of composition; about 0.3 mg antimicrobial agent/g of composition; about 0.4 mg antimicrobial agent/g of composition; about 0.5 mg antimicrobial agent/g of composition; about 1 mg antimicrobial agent/g of composition; about 1.5 antimicrobial agent/g of composition; about 2.0 mg antimicrobial agent/g of composition; about 3.0 mg antimicrobial agent/g of composition; about 4.0 mg antimicrobial agent/g of composition; about 5.0 mg antimicrobial agent/g of composition; about 6.0 mg antimicrobial agent/g of composition; about 7.0 mg antimicrobial agent/g of composition; about 8.0 mg antimicrobial agent/g of composition; about 9.0 mg antimicrobial agent/g of composition; about 10.0 mg antimicrobial agent/g of composition; about 12.5 mg antimicrobial agent/g of composition; about 15.0 mg antimicrobial agent/g of composition; about 20.0 mg antimicrobial agent/g of composition; or about 25.0 mg antimicrobial agent/g of composition.

In some embodiments, the methods are useful for treating or preventing a microbial infection, comprising administering to a subject in need thereof an effective amount of (i) bicarbonate and (ii) an antimicrobial agent, wherein the microbial infection is a dermal infection. In some embodiments, the bicarbonate and the antibacterial agent are administered topically. In some embodiments, the bicarbonate and the antibacterial agent are administered systemically. In some embodiments, the bicarbonate is administered systemically, and the antibacterial agent is administered topically. In some embodiments, the bicarbonate is administered topically, and the antibacterial agent is administered systemically. In some embodiments, the antibacterial agent is polymyxin B, colistin, azithromycin or diminazene, or a pharmaceutically acceptable salt thereof.

In some embodiments, the methods are useful for treating or preventing a microbial infection, comprising administering to a subject in need thereof an effective amount of (i) bicarbonate and (ii) an antimicrobial agent, wherein: the bicarbonate is administered in nebulized form, for example, as a nebulized solution or suspension; the antibacterial agent is administered intraperitoneally or in nebulized form, for example, as a nebulized solution or suspension; and wherein the microbial infection is a lung infection. In some embodiments, the antibacterial agent is polymyxin B, colistin, azithromycin or diminazene, or a pharmaceutically acceptable salt thereof.

In some embodiments, the methods are useful for treating or preventing a microbial infection, comprising administering to a subject in need thereof an effective amount of (i) bicarbonate and (ii) an antimicrobial agent, wherein the microbial infection is a systemic infection. In some embodiments, the antibacterial agent is polymyxin B, azithromycin, pentamidine or diminazene, or a pharmaceutically acceptable salt thereof. In some embodiments, the bicarbonate or the antibacterial agent is administered systemically (e.g., intravenously or intramuscularly).

In some embodiments, the methods are useful for treating or preventing a microbial infection, comprising administering to a subject in need thereof an effective amount of (i) bicarbonate and (ii) an antimicrobial agent, wherein the subject has cystic fibrosis. In some embodiments, the microbial infection is a lung infection. In some embodiments, the lung infection is by *Staphylococcus aureus*, methicillin-resistant *Staphylococcus aureus, Pseudomonas aeruginosa, Haemophilus* influenza, S. maltophillia, *Burkholderia* (ceno)*cepacia*. In some embodiments, one or both of the bicarbonate and the antimicrobial agent are administered to the subject in nebulized form, for example, as a nebulized solution or suspension. In some embodiments, the bicarbonate is administered as an 8.4% nebulized solution or suspension. In some embodiments, the antibacterial agent is administered intravenously, orally, intramuscularly or subcutaneously. In some embodiments, the antibacterial agent is polymyxin B, azithromycin or diminazene, or a pharmaceutically acceptable salt thereof.

In some embodiments, the methods are useful for surgical prophylaxis or treatment of a surgical complication. In some embodiments, the methods are useful for preventing or treating a microbial infection that is a complication of refractive, cataract or vitreo-retinal surgery, comprising administering to a subject in need thereof an effective amount of (i) bicarbonate and (ii) an antimicrobial agent. In some embodiments, an effective amount of (i) bicarbonate and (ii) an antimicrobial agent is administered to a subject during surgery. In some embodiments, an effective amount of (i) bicarbonate and (ii) an antimicrobial agent is administered to a subject prior to surgery. In some embodiments, an effective amount of (i) bicarbonate and (ii) an antimicrobial agent is administered to a subject after surgery. In some embodiments, an effective amount of (i) bicarbonate and (ii) an antimicrobial agent is administered to a subject prior to and during surgery. In some embodiments, an effective amount of (i) bicarbonate and (ii) an antimicrobial agent is administered to a subject prior to and after surgery. In some embodiments, an effective amount of (i) bicarbonate and (ii) an antimicrobial agent is administered to a subject during and after surgery. In some embodiments, an effective amount of (i) bicarbonate and (ii) an antimicrobial agent is administered to a subject prior to, during and after surgery.

In some embodiments, the antimicrobial agent is pentamidine, erythromycin, dirithromycin, levofloxacin, norfloxacin, ciprofloxacin, enoxacin, moxifloxacin, besifloxacin or polymyxin B, or a pharmaceutically acceptable salt thereof. In some embodiments, the invention provides compositions comprising pentamidine, erythromycin, dirithromycin, levofloxacin, norfloxacin, ciprofloxacin, enoxacin, moxifloxacin, besifloxacin or polymyxin B, or a pharmaceutically acceptable salt thereof, in an amount of about 0.1 wt % to about 1.0 wt %, or about 0.5 wt % of the composition, and bicarbonate in an amount of about 0.01 wt % to about 1.0 wt %, in some embodiments, about 0.20 wt % to about 0.5 wt %, of the composition.

In some embodiments, a microbial infection is pneumonia (e.g., *Pneumocystis* pneumonia (PCP)), meningitis, gastritis, ear infection (e.g., otitis, acute otitis externa, otitis media, otitis media with tympanostomy), an eye infection (e.g., bacterial conjunctivitis, pink eye, keratitis (also known as a corneal ulcer), trachoma, endophthalmitis, blepharitis, uveitis), a urinary tract infection, a kidney infection (e.g., pyelonephritis), liver infection (e.g., hepatitis), a skin infection (e.g., skin and skin structure infections, pimples, leprosy, carbuncle, boils, cellulitis, impetigo, pilonidal cyst, pilonidal abscess, erysipelas, folliculitis, furuncle, ecthyma), a fungal infection (e.g., athlete's foot, jock itch, ringworm, yeast infection, sporotrichosis, fungal nail infection), myositis, a respiratory tract infection, sinusitis, bronchitis, a sexually transmitted infection, or bacterial vaginosis. In some embodiments, the bacterial conjunctivitis is caused by an isolate of one of the following microbes: CDC coryneform group G, *Haemophilus influenzae, Staphylococcus aureus, Streptococcus mitis* group, and *Streptococcus pneumoniae*.

Further provided herein are methods for treating or preventing an ophthalmic infection, comprising administering to a subject in need thereof a an effective amount of (i) bicarbonate and (ii) an antimicrobial agent. In some embodiments, the ophthalmic infection is bacterial conjunctivitis. In some embodiments, the bacterial conjunctivitis is caused by one or more of the following microorganisms: CDC coryneform group G, *Haemophilus influenzae, Staphylococcus aureus, Streptococcus mitis* group, and *Streptococcus pneumoniae*. In some embodiments, the microorganisms are susceptible isolates. In some embodiments, the bicarbonate and antimicrobial agent are present in a composition. In some embodiments, the composition further comprises a pharmaceutically acceptable carrier or vehicle. In some embodiments, the methods comprise instilling 1 drop of the composition in the affected eye or eyes twice daily, eight to twelve hours apart for the first two days and then instilling 1 drop of the composition in the affected eye or eyes once daily for the next five days. In some embodiments, the ophthalmic infection is bacterial conjunctivitis. In some embodiments, the antimicrobial agent is present in the composition in an amount from about 5 mg to about 25 mg of antimicrobial agent/mL of composition. In some embodiments, the antimicrobial agent is present in the composition in an amount from about 5 mg to about 25 mg of antimicrobial agent/g of composition. In some embodiments, the antibacterial agent is a macrolide. In some embodiments, the macrolide is azithromycin.

Also provided herein are methods for treating or preventing an ophthalmic infection, comprising administering to a subject in need thereof an effective amount of (i) bicarbonate and (ii) an antimicrobial agent. In some embodiments, the ophthalmic infection is bacterial conjunctivitis. In some embodiments, the bacterial conjunctivitis is caused by one or more of the following microorganisms: CDC coryneform group G, *Haemophilus influenzae, Staphylococcus aureus, Streptococcus mitis* group, and *Streptococcus pneumoniae*. In some embodiments, the microorganisms are susceptible isolates. In some embodiments, the bicarbonate and antimicrobial agent are present in a composition. In some embodiments, the composition further comprises a pharmaceutically acceptable carrier or vehicle. In some embodiments, the method comprises instilling 1 drop of the composition in the affected eye or eyes three times a day for seven days. In some embodiments, an ophthalmic infection is bacterial conjunctivitis. In some embodiments, the antimicrobial agent is present in the composition in an amount from about 5 mg to about 25 mg of antimicrobial agent/mL of composition. In some embodiments, the antimicrobial agent is present in the composition in an amount from about 5 mg to about 25 mg of antimicrobial agent/g of composition. In some embodiments, the antibacterial agent is a macrolide. In some embodiments, the macrolide is azithromycin.

Additionally provided herein are methods for treating or preventing an ophthalmic infection, comprising administering to a subject in need thereof an effective amount of (i) bicarbonate and (ii) an antimicrobial agent. In some embodiments, the ophthalmic infection is bacterial conjunctivitis. In some embodiments, the bacterial conjunctivitis is caused by one or more of the following microorganisms: CDC coryneform group G, *Haemophilus influenzae, Staphylococcus aureus, Streptococcus mitis* group, and *Streptococcus pneumoniae*. In some embodiments, the microorganisms are susceptible isolates. In some embodiments, the bicarbonate and antimicrobial agent are present in a composition. In some embodiments, the composition further comprises a pharmaceutically acceptable carrier or vehicle. In some embodiments, the methods comprise instilling 1 drop of the composition in the affected eye or eyes three times a day, 4 to 12 hours apart, for seven days. In some embodiments, the ophthalmic infection is bacterial conjunctivitis. In some embodiments, the antimicrobial agent is present in the composition in an amount from about 5 mg to about 25 mg of antimicrobial agent/mL of composition. In some embodiments, the antimicrobial agent is present in the composition in an amount from about 5 mg to about 25 mg of antimicrobial agent/g of composition. In some embodiments, the antibacterial agent is a macrolide. In some embodiments, the macrolide is azithromycin.

Further provided herein are methods for treating or preventing an ophthalmic infection, comprising administering to a subject in need thereof a an effective amount of (i) bicarbonate and (ii) an antimicrobial agent. In some embodiments, the ophthalmic infection is bacterial conjunctivitis. In some embodiments, the bacterial conjunctivitis is caused by one or more of the following microorganisms: CDC coryneform group G, *Haemophilus influenzae, Staphylococcus aureus, Streptococcus mitis* group, and *Streptococcus pneumoniae*. In some embodiments, the microorganisms are susceptible isolates. In some embodiments, the bicarbonate and antimicrobial agent are present in a composition. In some embodiments, the composition further comprises a pharmaceutically acceptable carrier or vehicle. In some embodiments, the methods comprise instilling 4 drops of the composition in the affected eye or eyes daily, for seven to 10 days. In some embodiments, the antimicrobial agent is present in the composition in an amount from about 5 mg to about 25 mg of antimicrobial agent/mL of composition. In some embodiments, the antimicrobial agent is present in the composition in an amount from about 5 mg to about 25 mg of antimicrobial agent/g of composition. In some embodiments, the antibacterial agent is a macrolide. In some embodiments, the macrolide is azithromycin.

Also provided herein are methods for treating or preventing a skin infection, comprising administering to a subject in need thereof an effective amount of (i) bicarbonate and (ii) an antimicrobial agent. In some embodiments, the bicarbonate and antimicrobial agent are present in a composition. In some embodiments, the composition further comprises a pharmaceutically acceptable carrier or vehicle. In some embodiments, the methods comprise applying the composition to the affected skin area 2-3 times a day for up to 10 days. In some embodiments, a skin infection is impetigo, folliculitis, furunculosis or ecthyma. In some embodiments, the skin infection is a diabetic foot infection. In some embodiments, the antimicrobial agent is present in the composition in an amount from about 5 mg to about 25 mg of antimicrobial agent/mL of composition. In some embodiments, the antimicrobial agent is present in the composition in an amount from about 5 mg to about 25 mg of antimicrobial agent/g of composition. In some embodiments, the antibacterial agent is a macrolide. In some embodiments, the macrolide is azithromycin.

Also provided herein are methods for treating or preventing an otic infection, comprising administering to a subject in need thereof an effective amount of (i) bicarbonate and (ii) an antimicrobial agent. In some embodiments, the bicarbonate and antimicrobial agent are present in a composition. In some embodiments, the composition further comprises a pharmaceutically acceptable carrier or vehicle. In some embodiments, the methods comprise instilling four drops into the affected ear or ears twice daily, for seven days. In some embodiments, the otic infection is acute otitis media or acute otitis externa. In some embodiments, the antimicrobial agent is present in the composition in an amount from about 5 mg to about 25 mg of antimicrobial agent/mL of composition. In some embodiments, the antimicrobial agent is present in the composition in an amount from about 5 mg to about 25 mg of antimicrobial agent/g of composition. In some embodiments, the antibacterial agent is a macrolide. In some embodiments, the macrolide is azithromycin.

In some embodiments, the methods of the invention further comprise administering to a subject in need thereof another pharmaceutically active agent. In some embodiments, the other pharmaceutically active agent is a steroid. In some embodiments, a steroid is dexamethasone, fluocinolone acetonide, prednisone, prednisolone acetate, triamcinolone or hydrocortisone, or a pharmaceutically acceptable salt thereof.

In some embodiments, the methods described herein do not inhibit the growth of natural or beneficial microbiota of a subject.

In some embodiments, the microbe is present in a biofilm. In some embodiments, the infection is a biofilm infection.

In some embodiments, the invention encompasses use of an effective amount of (i) bicarbonate and (ii) an antimicrobial agent for treating or preventing a microbial infection. In some embodiments, the invention encompasses use of an effective amount of (i) bicarbonate and (ii) an antimicrobial agent for inhibiting growth of a microbe.

Compositions, Pharmaceutical Uses and Routes of Administration

In some embodiments, provided herein are compositions comprising: an effective amount of (i) bicarbonate and (ii) an antimicrobial agent.

Provided herein are compositions comprising: an effective amount of (i) bicarbonate and (ii) an antimicrobial agent; wherein the antimicrobial agent is azithromycin, amikacin, clarithromycin, clindamycin, dirithromycin, erythromycin, polymyxin B, vancomycin, colistin, daptomycin, fusidic acid, lincomycin, metronidazole, mupirocin, roxithromycin, sparfloxacin, spiramycin, streptomycin, teicoplanin, telithromycin, tobramycin, troleandomycin, tulathromycin, apramycin, gentamicin, kanamycin, neomycin, paromycin, spectinomycin, ampicillin, amoxicillin, cloxacillin, nafcillin, piperacillin, oxacillin, ciprofloxacin, besifloxacin, enoxacin, gatifloxacin, gemifloxacin, grepafloxacin, levofloxacin, lomefloxacin, moxifloxacin, nalidixic acid, norfloxacin, ofloxacin, pefloxacin, pefloxin, sparfloxacin, temafloxacin, trovafloxacin, ceftriaxone, cefoperazone, chloramphenicol, linezolid, posizolid, radezolid, tedizolid (formerly torezolid), bacitracin, fosfomycin, fosmidomycin, novobiocin, pentamidine, rifampicin, trimethoprim, sulfamethoxazole, sulfasalazine, paromomycin, ertapenem, doripenem, imipenem/cilastatin, meropenem, telavancin, lipopeptide, aztreonam, mafenide, benzamide, furadinozoline, gramicidin, hygromycin B, nadifloxacin, nisin, pleuromutilin, thiostrepton, triclosan, bromocriptine mesylate, aminacrine, acrisorcin, mitoxantrone hydrochloride, amsacrine, homidium bromide, sulfamethazine, sulfaphenazole, chloroxine, acriflavinium hydrochloride, diminazene (e.g., diminazene aceturate or diminazene diaceturate), sulfapyridine, ropinirole hydrochloride, sulfaguanidine, metergoline, closantel, sulfameter, cefalonium, sulfadoxine, doxorubicin, cetrimonium bromide, phenylmercuric acetate, dequalinium chloride, clioquinol, amiodarone hydrochloride, monobenzone, proflavine hemisulfate, nisoldipine, methylbenzethonium chloride, cephalothin sodium, fluvoxamine maleate, tacrine hydrochloride, guanabenz acetate, ramoplanin, orlistat, clofoctol, puromycin hydrochloride, broxaldine, sanguinarine sulfate, dihydrostreptomycin sulfate, octisalate, ethacridine lactate, bithionate sodium, montelukast sodium, oltipraz, ipratropium bromide, ipriflavone, enalapril maleate, flopropione, sulfaquinoxaline sodium, bisoctrizole, azathioprine, enalaprilat, exalamide, benzalkonium chloride, benzethonium chloride, cetrimonium bromide, cetylpyridinium chloride, chlorhexidine, dibrompropamidine diisetionate, hexadecyltrimethylammonium bromide, p-hydroxybenzoate, polyhexanide, a polyvinylpyrrolidone iodine complex, or a pharmaceutically acceptable salt thereof.

Also provided herein are compositions comprising: an effective amount of (i) bicarbonate and (ii) an antimicrobial agent, wherein the bicarbonate is sodium bicarbonate and the antimicrobial agent is diminazene (e.g., diminazene aceturate or diminazene diaceturate), cetylpyridinium chloride, dequalinium chloride, aminacrine, amsacrine or mitoxanthrone, or a pharmaceutically acceptable salt thereof.

Also provided herein are compositions comprising: an effective amount of (i) bicarbonate and (ii) an antimicrobial agent; wherein the antimicrobial agent is amikacin, azithromycin, clarithromycin, clindamycin, polymyxin B, colistin, daptomycin, fusidic acid, gatifloxacin, lincomycin, lomefloxacin, metronidazole, mupirocin, roxithromycin, sparfloxacin, spiramycin, streptomycin, teicoplanin, telithromycin or tobramycin, or a pharmaceutically acceptable salt thereof; and (a) wherein the bicarbonate is present in the composition at a concentration of about 1 millimoles to about 900 millimoles/L of the composition; or (b) wherein the bicarbonate is present in the composition in an amount of about 0.01 wt % to about 8.4 wt % of the composition.

Also provided herein are compositions comprising: an effective amount of (i) bicarbonate and (ii) an antimicrobial agent, wherein the bicarbonate is sodium bicarbonate and the antimicrobial agent is azithromycin, clarithromycin, roxithromycin, spiramycin, telithromycin, moxifloxacin, besifloxacin, streptomycin, spectinomycin, polymyxin B or pentamidine (e.g., pentamidine isethionate), or a pharmaceutically acceptable salt thereof; and (a) wherein the bicarbonate is present in the composition at a concentration of about 1 millimoles to about 900 millimoles/L of the composition; or (b) wherein the bicarbonate is present in the composition in an amount of about 0.01 wt % to about 8.4 wt % of the composition. In some embodiments, the bicarbonate is present at a concentration of about 175 millimoles to about 900 millimoles/L of the composition. In some embodiments of this composition, the bicarbonate is present at a concentration of about 175 millimoles to about 225 millimoles, about 200 millimoles to about 300 millimoles, about 300 millimoles to about 400 millimoles, about 400 millimoles to about 500 millimoles, about 500 millimoles to about 600 millimoles, about 600 millimoles to about 700 millimoles, about 700 millimoles to about 800 millimoles or about 800 millimoles to about 900 millimoles/L of the composition.

Also provided herein are compositions comprising: an effective amount of (i) bicarbonate and (ii) an antimicrobial agent, wherein the bicarbonate is sodium bicarbonate, and wherein the antimicrobial agent is present in the composition in an amount of about 0.01 mg antimicrobial agent/mL of composition; about 0.02 mg antimicrobial agent/mL of composition; about 0.03 mg antimicrobial agent/mL of composition; about 0.04 mg antimicrobial agent/mL of composition; about 0.05 mg antimicrobial agent/mL of composition; about 0.1 mg antimicrobial agent/mL of composition; about 0.2 mg antimicrobial agent/mL of composition; about 0.3 mg antimicrobial agent/mL of composition; about 0.4 mg antimicrobial agent/mL of composition; about 0.5 mg antimicrobial agent/mL of composition; about 1 mg antimicrobial agent/mL of composition; about 1.5 mg antimicrobial agent/mL of composition; about 2.0 mg antimicrobial agent/mL of composition; about 3.0 mg antimicrobial agent/mL of composition; about 4.0 mg antimicrobial agent/mL of composition; about 5.0 mg antimicrobial agent/mL of composition; about 6.0 mg antimicrobial agent/mL of composition; about 7.0 mg antimicrobial agent/mL of composition; about 8.0 mg antimicrobial agent/mL of composition; about 9.0 mg antimicrobial agent/mL of composition; about 10.0 mg antimicrobial agent/mL of composition; about 12.5 mg antimicrobial agent/mL of composition; about 15.0 mg antimicrobial agent/mL of composition; about 20.0 mg antimicrobial agent/mL of composition; or about 25.0 mg antimicrobial agent/mL of composition. In some embodiments, the antimicrobial agent is azithromycin. In some embodiments, a composition comprises sodium bicarbonate at a concentration of about 30 millimoles to about 100 millimoles of sodium bicarbonate/L of composition.

Further provided herein are compositions comprising: an effective amount of (i) bicarbonate and (ii) an antimicrobial agent, wherein the bicarbonate is sodium bicarbonate, and wherein the antimicrobial agent is present in a composition in an amount of about 0.01 mg antimicrobial agent/g of composition; about 0.02 mg antimicrobial agent/g of composition; about 0.03 mg antimicrobial agent/g of composition; about 0.04 mg antimicrobial agent/g of composition; about 0.05 mg antimicrobial agent/g of composition; about 0.1 mg antimicrobial agent/g of composition; about 0.2 mg antimicrobial agent/g of composition; about 0.3 mg antimicrobial agent/g of composition; about 0.4 mg antimicrobial agent/g of composition; about 0.5 mg antimicrobial agent/g of composition; about 1 mg antimicrobial agent/g of composition; about 1.5 antimicrobial agent/g of composition; about 2.0 mg antimicrobial agent/g of composition; about 3.0 mg antimicrobial agent/g of composition; about 4.0 mg antimicrobial agent/g of composition; about 5.0 mg antimicrobial agent/g of composition; about 6.0 mg antimicrobial agent/g of composition; about 7.0 mg antimicrobial agent/g of composition; about 8.0 mg antimicrobial agent/g of composition; about 9.0 mg antimicrobial agent/g of composition; about 10.0 mg antimicrobial agent/g of composition; about 12.5 mg antimicrobial agent/g of composition; about 15.0 mg antimicrobial agent/g of composition; about 20.0 mg antimicrobial agent/g of composition; or about 25.0 mg antimicrobial agent/g of composition. In some embodiments, the antimicrobial agent is azithromycin. In some embodiments, a composition comprises sodium bicarbonate at a concentration of about 30 millimoles to about 100 millimoles/L of composition.

The compositions of the invention can comprise any one or more of the antimicrobial agents described herein.

In some embodiments, the compositions described herein further comprise a pharmaceutically acceptable carrier, diluent or excipient. In some embodiments, a pharmaceutically acceptable carrier is a non-toxic solvent, dispersant, excipient, adjuvant or other material which is mixed with the active ingredient (e.g., the bicarbonate or the antimicrobial agent) in order to permit the formation of a pharmaceutical composition, i.e., a dosage form capable of administration to a subject. In some embodiments, pharmaceutically acceptable carriers, diluents or excipients, include, but are not limited to, preservatives, viscosity agents, buffering agents, binders, fillers, disintegrants, wetting agents, lubricants, glidants, coloring agents, dye-migration inhibitors, sweetening agents, and flavoring agents.

In some embodiments, the compositions of the invention further comprise a preservative. In some embodiments, the preservative is benzalkonium chloride, chlorobutanol, thimerosal, benzyl alcohol, glycerin, methylparaben, propylparaben, benzoic acid, sodium benzoate or alcohol. In some embodiments, the compositions comprise about 0.003% to about 0.01% of benzalkonium chloride as a preservative.

In some embodiments, the compositions of the invention further comprise a viscosity agent. In some embodiments, the viscosity agent is methylcellulose, hyaluronic acid, propylene glycol, polycarbophil, mannitol or poloxamer 407.

In some embodiments, the compositions of the invention further comprise a buffering agent. In some embodiments, a buffering agent is citrate buffer, borate buffer, HCl/NaOH, distilled or purified water, or sodium chloride.

In some embodiments, provided herein is a composition comprising: an effective amount of (i) bicarbonate and (ii) an antimicrobial agent, and further comprising benzalkonium chloride, mannitol, citric acid, sodium citrate, poloxamer 407, polycarbophil, edetate disodium (EDTA), sodium chloride, water for injection, and sodium hydroxide to adjust pH to 6.3. In some embodiments, the benzalkonium chloride is present at about 0.003 wt % of the compositions.

In some embodiments, the compositions of the invention are sterile.

In some embodiments, the compositions of the invention have a pH of about 6.5, about 6.6, about 6.7, about 6.8, about 6.9, about 7.0, about 7.1, about 7.2, about 7.3, about 7.4 or about 7.5.

In some embodiments, a composition of the invention is a tablet. In some instances, the tablet comprises one or more excipients. An excipient may be a diluent, a disintegrant, a wetting agent, a swellable agent, a binder, a glidant, a lubricant, a coating vehicle (e.g., a film coating vehicle), an anti-foaming agent, a stabilizing agent or any combination thereof. For example, the tablet comprises a binder (e.g., microcrystalline cellulose, dibasic calcium phosphate, sucrose, corn starch, polyvinylpyrridone, hydroxyporopyl cellulose, hydroxymethyl cellulose, or any combination thereof). In another example, the tablet comprises a disintegrant. The tablet may comprise a disintegrant such as sodium croscarmellose or sodium starch glycolate, or combinations of disintegrants. In other embodiments, the tablet comprises a lubricant (e.g., stearic acid as free acid or as a salt, magnesium stearate, sodium stearyl fumarate, hydrogenated oils, or colloidal silicon dioxide, or any combination thereof).

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, Panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof.

Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The binder or filler may be present from about 5 to about 49% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as various types of sodium starch glycolate; polacrilin potassium; starches, such as corn starch, potato starch, tapioca starch, and pre-gelatinized starch; clays; aligns; and mixtures thereof. The amount of disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include colloidal silicon dioxide, CAB-O-SIL® (Cabot Co. of Boston, Mass.), and asbestos-free talc.

Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye.

Flavoring agents include natural flavors extracted from plants, such as fruits, and synthetic blends of compounds which produce a pleasant taste sensation, such as peppermint and methyl salicylate.

Sweetening agents include sucrose, lactose, mannitol, syrups, glycerin, sucralose, and artificial sweeteners, such as saccharin and aspartame.

Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrolidone. Preservatives include glycerin, methyl and propylparaben, benzoic acid, sodium benzoate and alcohol. Wetting agents include propylene glycol monostearate, sorbitan monooleate, diethylene glycol monolaurate, and polyoxyethylene lauryl ether.

Solvents include glycerin, sorbitol, ethyl alcohol, and syrup.

Examples of non-aqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The compositions provided herein may be provided as compressed tablets, tablet triturates, chewable lozenges, rapidly dissolving tablets, multiple compressed tablets, enteric-coating tablets, sugar-coated tablets, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, methacrylic acid copolymers, methacrylic and methacrylate acid copolymers, fatty acids, fats, phenylsalicylate, waxes, shellac, ammoniated shellac, cellulose acetate phthalates, cellulose acetate butyrate, hydroxypropylmethylcellulose phthalate (HPMCP), and algenic acid salts such as sodium or potassium alginate. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The compositions provided herein may be soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent growth of microbes. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquids or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde (the term "lower" means an alkyl having between 1 and 6 carbon atoms), e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

The compositions provided herein for oral administration may be also provided in the forms of liposomes, micelles, microspheres, multiparticulate-filled capsules (enterically-coated microbeads in a capsule) or nanosystems. Micellar dosage forms can be prepared as described in U.S. Pat. No. 6,350,458.

The compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms. And, flavoring and sweetening agents are especially useful in the formation of chewable tablets and lozenges.

The compositions provided herein may be formulated as immediate or modified release dosage forms, including delayed-, extended, pulsed-, controlled, targeted-, and programmed-release forms.

The compositions provided herein may be co-formulated with other active ingredients which do not impair the desired therapeutic action, or with substances that supplement the desired action.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants.

The bicarbonate or antimicrobial agent can be administered to a subject, or used, in a variety of forms depending on the selected route of administration, as will be understood by those skilled in the art. In some embodiments, the bicarbonate or antimicrobial agent is administered to a subject systemically.

In some embodiments, the composition is suitable for administration intraocularly. In some embodiments, the composition is useful as a topical ophthalmic solution or suspension, or is for topical, subconjunctival, periocular, retrobulbar, sub-tenon, intracameral, intravitreal, intraocular, subretinal, juxtascleral or suprachoroidal administration.

In some embodiments, the bicarbonate or antimicrobial agent is administered to a subject, or used, by oral (including sublingual and buccal) or parenteral (including intravenous, intraperitoneal, subcutaneous, intramuscular, transepithelial, nasal, intrapulmonary, intrathecal, rectal, topical, patch, pump, intraocular and transdermal) administration and the compound(s) formulated accordingly. In some embodiments, both the bicarbonate and the antimicrobial agent are administered orally. In some embodiments, both the bicarbonate and the antimicrobial agent are administered parenterally. In some embodiments, the bicarbonate and the antimicrobial agent are administrated via different modes of administration. In some embodiments, the bicarbonate is administered parenterally and the antimicrobial agent is administered orally. In some embodiments, the bicarbonate is administered orally and the antimicrobial agent is administered parenterally.

In some embodiments, the bicarbonate or an antimicrobial agent is administered to the subject orally. In another embodiments, the bicarbonate or an antimicrobial agent is administered to the subject intravenously. In some embodiments, the bicarbonate is administered to a subject as an about 8.4% w/v (weight/volume percent) solution.

In some embodiments, the bicarbonate or the antimicrobial agent is administered to a subject as a topical ophthalmic solution or suspension, or by topical, dermal, transdermal, subconjunctival, periocular, retrobulbar, sub-tenon, intracameral, intravitreal, intraocular, subretinal, juxtascleral or suprachoroidal administration.

The pharmaceutical forms suitable for injectable use can include sterile aqueous solutions or dispersions and sterile powders for the extemporaneous preparation of sterile injectable solutions or dispersions. In some embodiments, the form is sterile and fluid to the extent that easy syringability exists.

In some embodiments, parenteral administration can be by continuous infusion over a selected period of time. Solutions suitable for parenteral administration can be prepared by known methods by a person skilled in the art. For example, the bicarbonate or an antimicrobial agent can be prepared in water optionally mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations can contain a preservative to prevent growth of microbes. A pharmaceutically acceptable oil may be used as a carrier for parenteral administration.

Compositions for nasal administration can be conveniently formulated as aerosols, drops, suspensions, gels or powders. Aerosol formulations typically comprise a solution or fine suspension of the active substance in a physiologically acceptable aqueous or non-aqueous solvent and are can be prepared in single or multidose quantities in sterile form in a sealed container, which take the form of a cartridge or refill for use with an atomising device. Alternatively, the sealed container can be a unitary dispensing device such as a single dose nasal inhaler or an aerosol dispenser fitted with a metering valve which is intended for disposal after use. Where the dosage form comprises an aerosol dispenser, it can contain a propellant which is, for example, a compressed gas such as compressed air or an organic propellant such as fluorochlorohydrocarbon. In some embodiments, the aerosol dosage forms can take the form of a pump-atomizer. In some embodiments, the bicarbonate can be administered to a subject as an about 8.4% w/v aerosolized solution.

In some embodiments, the bicarbonate or the antimicrobial agent can be nebulized. In some embodiments, the bicarbonate or the antimicrobial agent can be administered via an inhaler. In some embodiments, the bicarbonate can be administered to a subject as an about 5% w/v nebulized solution. In some embodiments, the bicarbonate is administered to a subject in nebulized form, for example, as an about 50 mM to about 225 mM nebulized solution or suspension.

Compositions suitable for buccal or sublingual administration can include tablets, lozenges, and pastilles, wherein the active ingredient is formulated with a carrier such as sugar, acacia, tragacanth, gelatin or glycerine. Compositions for rectal administration can conveniently be in the form of suppositories containing a conventional suppository base such as cocoa butter.

In some embodiments provided herein, a composition useful for treating an ophthalmic infection is provided. In some embodiments, the composition contains an effective amount (i) bicarbonate and (ii) an antimicrobial agent as provided herein and a pharmaceutical excipient suitable for ocular administration. In some embodiments, pharmaceutical compositions suitable for ocular administration can be presented as discrete dosage forms, such as drops or sprays each containing a predetermined amount of the active ingredient(s) in a solution, or a suspension in an aqueous or non-aqueous liquid, an oil-in-water emulsion, or a water-in-oil liquid emulsion. Other administration forms can include intraocular injection, intravitreal injection, topically, or through the use of a drug eluting device, microcapsule, implant, or microfluidic device. In some embodiments, the compounds as provided herein can be administered with a carrier or excipient that increases the intraocular penetrance of the compound such as an oil and water emulsion with colloid particles having an oily core surrounded by an interfacial film. The compositions of the invention can be administered to the eye via topical, subconjunctival, periocular, retrobulbar, subtenon, intracameral, intravitreal, intraocular, subretinal, juxtascleral or suprachoroidal administration.

In some embodiments, eye drops can be prepared by dissolving the active ingredient(s) in a sterile aqueous solution such as physiological saline, buffering solution, etc., or by combining powder compositions to be dissolved before use. Other vehicles can be chosen, as is known in the art, including, but not limited to: balance salt solution, saline solution, water soluble polyethers such as polyethylene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. In some embodiments, additives ordinarily used in the eye drops can be added. Such additives can include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc.; e.g., mucopolysaccharide such as chondroitin sulfate, etc.; e.g., sodium polyacrylate, carboxyvinyl polymer, crosslinked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

In another embodiment, bicarbonate or an antimicrobial agent can be orally administered, for example, with an inert diluent or with an assimilable edible carrier, or they can be enclosed in hard or soft shell gelatin capsules, or compressed into tablets, or incorporated directly with the food of a diet. For oral administration, the bicarbonate and an antimicrobial agent can be incorporated with excipients and used in the form of, for example, ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., molecular sieving type particles, or, a fine hollow permeable fiber bundle, or chopped hollow permeable fibers, agglomerated or held in a fibrous packet. In some embodiments, timed-release compositions can be, formulated, as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of lipids, such as cholesterol, stearylamine or phosphatidylcholines.

It is also possible to freeze-dry the bicarbonate or an antimicrobial agent and use the lyophilizate obtained, for example, for the preparation of products for injection.

In some embodiments, the bicarbonate or an antimicrobial agent can be coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. In a further embodiment, the bicarbonate and antimicrobial agent can be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

In some embodiments, the compositions of the invention are not suitable for oral administration. In some embodiments, the compositions are suitable for only topical administration. In some embodiments, the compositions are suitable for only ocular administration. In some embodiments, the compositions do not comprise an adhesive. In some embodiments, the compositions do not comprise a polycarbophil adhesive. In some embodiments, the compositions do not comprise a gel matrix. In some embodiments, the compositions do not comprise a carbomer, poloxamer (e.g., poloxamer 407), hydroxypropyl methylcellulose or methylcellulose gel matrix. In some embodiments, the compositions do not comprise an adhesive or a gel matrix. In some embodiments, the compositions do not comprise an adhesive and a gel matrix.

In some embodiments, the bicarbonate or antimicrobial agent, or a composition comprising bicarbonate and an antimicrobial agent, is contained in the interior of a container. In some embodiments, the interior of the container is sterile. In some embodiments, a container is a dropper bottle or a vial. In some embodiments, a container contains about 0.3 mL, 0.5 mL, 0.75 mL, 1.0 mL, 2.0 mL, 2.5 mL, 3.0 mL, 3.5 mL, 4.0 mL, 5.0 mL, 6.0 mL, 7.0 mL, 8.0 mL, 9.0 mL, 10 mL, 11 mL, 12 mL, 13 mL, 14 mL or 15 mL of a composition. In some embodiments a container contains about 0.9 g, about 1.0 g, about 2.5 g, about 5.0 g, about 7.5 g, about 10 g, about 15 g, about 20 g, about 25 g or about 30 g of a composition. In some embodiments a container contains about 200 g of a composition that is suitable for veterinary use. In some embodiments, a container is a single-use container. In some embodiments, a container contains a unit dose of a composition.

In some embodiments, the bicarbonate and an antimicrobial agent are effective for treating a systemic, pulmonary, lung, otic, oral, nasal, sinus, ophthalmic, intraocular, dermal, cardiovascular, kidney, urinary, gastrointestinal, rectal, vaginal or neurological infection, and the compounds formulated accordingly. In some embodiments, the methods and compositions described herein are useful to treat a systemic, pulmonary, lung, otic, oral, nasal, sinus, ophthalmic, intraocular, dermal, cardiovascular, kidney, urinary, gastrointestinal, rectal, vaginal or neurological infection. In some embodiments, the methods and compositions described herein are useful to treat an infection of a mucous membrane.

In some embodiments, the bicarbonate or an antimicrobial agent can be administered as a topical composition, such as a solution, gel, cream, lotion, suspension, aerosol, nebulized spray, ointment, drops or patch.

Accordingly, in some embodiments, the bicarbonate or an antimicrobial agent can be administered intraocularly, for example, as a topical ophthalmic solution or suspension (pulsed or sustained released delivery), or by topical, subconjunctival, periocular, retrobulbar, sub-tenon, intracameral, intravitreal, intraocular, subretinal, juxtascleral or suprachoroidal administration.

The bicarbonate and an antimicrobial agent can be used with each other. The bicarbonate and an antimicrobial agent can be either used or administered separately in time or in mode of administration (i.e., different administration routes) or they can be administered together in the same pharmaceutical preparation.

In some embodiments, bicarbonate and an antimicrobial agent can be used or administered separately in time or in mode of administration. For example, the bicarbonate can be administered by injection and the antimicrobial agent can be administered orally. In another example, the bicarbonate can be administered orally and the antimicrobial agent can be administered by injection. In a further example, both the bicarbonate and the antimicrobial agent can be administered by injection. In another example, the bicarbonate can be administered as a nebulized solution and the antimicrobial agent can be administered intraperitoneally. When the bicarbonate and the antimicrobial agent are used or administered separately in time or in mode of administration, the bicarbonate can be administered, or used, either before or after administration, or use, of the antimicrobial agent. In some embodiments, the bicarbonate and the antimicrobial agent can be administered to a body orifice of the subject.

The exact details of the administration will depend on the pharmacokinetics of the bicarbonate and the antimicrobial agent in the presence of each other, and can include administering bicarbonate and the antimicrobial agent within a few hours of each other, or even administering the bicarbonate and the antimicrobial agent within about 6 hours, about 10 hours, about 12 hours, about 18 hours, about 24 hours or greater of administration of the other, if the pharmacokinetics are suitable. Design of suitable dosing regimens is routine for one skilled in the art.

In some embodiments, bicarbonate and an antimicrobial agent are administered to a subject in a single composition or formulation. In some embodiments, a single composition or formulation may comprise bicarbonate and one, two, three or more antimicrobial agents.

Methods for treatment or prevention can comprise administering to a subject the bicarbonate and an antimicrobial agent as a single administration, or alternatively two or more administrations. The length of the treatment period can depend on a variety of factors, such as the severity of the infection, disease, disorder or condition, the age of the subject, the dosage of the bicarbonate or antimicrobial agent, or the activity of the bicarbonate or antimicrobial agent.

In some embodiments, the antimicrobial agent can be administered or used according to treatment protocol that is known for the antimicrobial agent in the treatment in microbial infections.

In some embodiments, the bicarbonate and an antimicrobial agent can be administered or used as soon as practicable after exposure to the microbe. In some embodiments, the bicarbonate and an antimicrobial agent can be administered or used until treatment of the microbial infection is achieved. For example, the bicarbonate and an antimicrobial agent can be administered or used until complete elimination of the microbe is achieved, or until the number of microbes has been reduced to the point where the subject's defenses are no longer overwhelmed and can kill any remaining microbes.

The dosage of the bicarbonate and an antimicrobial agent can vary depending on many factors such as the pharmacodynamic properties thereof, the mode of administration, the age, health and weight of the subject, the nature and extent of the symptoms, the frequency of the treatment and the type of concurrent treatment, if any, and the clearance rate in the subject to be treated. One of skill in the art can determine the appropriate dosage based on the above factors. In some embodiments, the bicarbonate and an antimicrobial agent are administered initially in a suitable dosage that may be adjusted as required, depending on the clinical response.

In some embodiments, the dosage, or effective amount, of the antimicrobial agent is be equal to or less than the dosage of such agents when used alone.

In some embodiments, the compositions of the invention comprise another pharmaceutically active agent. In some embodiments, the other pharmaceutically active agent is a steroid. In some embodiments, a steroid is dexamethasone, fluocinolone acetonide, prednisone, prednisolone acetate, triamcinolone or hydrocortisone, or a pharmaceutically acceptable salt thereof. In some embodiments, a steroid is present in the composition in an amount of about 0.025 wt % to about 1 wt % of the composition.

Screening for Antimicrobial Agents

Provided herein are methods of screening for antimicrobial agents or compounds.

In some embodiments, the methods for screening for an antimicrobial agent comprises (1) contacting a microbe with a test compound in the presence of bicarbonate; and (2) observing growth of the microbe, wherein a decrease in the growth of the microbe in the presence of the test compound compared to in the absence of the test compound indicates that the test compound is an antimicrobial agent.

In other embodiments, provided herein are methods for screening for antimicrobial compounds that can be modulated by bicarbonate comprising: (1) contacting a microbe with a test compound in the absence of bicarbonate, (2) contacting the microbe with a test compound in the presence of bicarbonate; and (3) observing growth of the microbe, wherein a greater change in the growth of the microbe with the test compound in the presence of bicarbonate compared to the growth of the microbe in the absence of bicarbonate indicates that the test compound is an antimicrobial compound that is modulated by bicarbonate.

In some embodiments, a microbe is a virus, a bacterium, a fungus or a parasite.

In some embodiments, the concentration of bicarbonate is about 20 mM to about 75 mM, or about 25 mM to about 50 mM, or about 20 mM to about 100 mM, or about 20 mM to about 150 mM, or about 50 to about 150 mM, or about 50 mM to about 100 mM. In some embodiments, the bicarbonate is present at a concentration of about 1 mM, about 5 mM, about 10 mM, about 15 mM, about 20 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, about 105 mM, about 110 mM, about 115 mM, about 120 mM, about 125 mM, about 130 mM, about 135 mM, about 140 mM, about 145 mM or about 150 mM. In some embodiments, the bicarbonate is present at a concentration of about 175 mM to about 900 mM. In some embodiments, the bicarbonate is present at a concentration of about 175 mM to about 225 mM, about 200 mM to about 300 mM, about 300 mM to about 400 mM, about 400 mM to about 500 mM, about 500 mM to about 600 mM, about 600 mM to about 700 mM, about 700 mM to about 800 mM or about 800 mM to about 900 mM.

In some embodiments two or more test compounds may be tested. In some embodiments, two or more microbes may be tested.

In some embodiments, the methods for screening can be performed at different concentrations of the test compound and an MIC of the test compound is determined. In some embodiments, the MIC is the lowest concentration of a test compound that prevents detectable growth of the microbe, in some embodiments, visible growth of the microbe after overnight incubation.

In some embodiments, an FIC index calculation (shown below) is used to screen for an antimicrobial agent. In some embodiments, a FIC index value of less than or equal to 0.5 indicates synergy between a test compound and bicarbonate.

$$\text{FIC index} = \text{FIC}_{bicarbonate\ salt} + \text{FIC}_{test\ compound}$$

Fractional Inhibitory Concentration (FIC)=[X]/MIC$_X$, where [X] is the lowest inhibitory concentration of drug in the presence of the co-drug.

EXAMPLES

Materials and Methods.

In the following experiments, bacterial cells were cultured in 96-well microtiter plates in cation-adjusted Mueller-Hinton Broth (MHB) for 18 h at 37° C. The main strains used were *E. coli* (K-12 BW25113) (placed in stationary incubator) and *S. aureus* (Newman Strain) (incubated at 250 r.p.m). Knockout strains (ΔtolcC and ΔychM) were used from the Keio knockout collection (Baba et al., Construction of *Escherichia coli* K-12 in-frame, single-gene knockout mutants: the Keio collection. Mol Syst Biol 2, 2006 0008, doi:10.1038/msb4100050 (2006)). For MIC determination and checkerboard analyses, Clinical & Laboratory Standards Institute (CLSI) protocol was used. Tetracycline uptake was assayed as previously described (Ejim et al., Combinations of antibiotics and nonantibiotic drugs enhance antimicrobial efficacy. *Nature chemical biology* 7, 348-350, doi:10.1038/nchembio.559 (2011)). DiSC$_3$ loading of *S. aureus* cells was performed as previously described (Farha et al., Collapsing the proton motive force to identify synergistic combinations against *Staphylococcus aureus*. *Chemistry & biology* 20, 1168-1178, doi:10.1016/j.chembiol.2013.07.006 (2013)). CCCP concentration of 20 μM was used. pH adjustments were made by addition of HCl or NaOH. INT assay and ATP bioluminescence assays were performed as previously described (Farha et al., Collapsing the proton motive force to identify synergistic combinations against *Staphylococcus aureus. Chemistry & biology* 20, 1168-1178, doi:10.1016/j.chembiol.2013.07.006 (2013)). For chemical-genomic studies, the Keio library was grown overnight in cation-adjusted MHB broth, in 384-well plates. From these, treatment plates (25 mM sodium bicarbonate, or a sterile water control) were inoculated and grown for 15 hours at 37° C., in a stationary incubator. Data was normalized according to Mangat et al (Mangat et al., Rank ordering plate data facilitates data visualization and normalization in high-throughput screening. *J Biomol Screen* 19, 1314-1320, doi: 10.1177/1087057114534298 (2014)), with gene products and GO terms mined from EcoCyc. The GFP promoter library (Keseler et al., EcoCyc: fusing model organism databases with systems biology. *Nucleic Acids Res* 41, D605-612, doi:10.1093/nar/gks1027 (2013)) was grown for 18 hours at ambient temperature with the same inoculation strategy as with the Keio collection. The analysis pipeline of Zaslaver et al (Zaslaver et al., A comprehensive library of fluorescent transcriptional reporters for *Escherichia coli*. *Nat Methods* 3, 623-628, doi:10.1038/nmeth895 (2006)) was used to generate maps of promoter activity, from which lists of promoters with increased or decreased activity were compiled.

Example 1: Pentamidine Isethionate Possesses Monotherapy Activity in a Murine Model of Systemic *A. baumannii* Infection

*A. baumannii* was injected into mice intraperitoneally ($1.5 \times 10^6$ CFU *A. baumannii*) and after two hours mice were treated intraperitoneally ("IP") with a single dose of PBS (n=10), novobiocin at 5 mg/kg (n=10), pentamidine isethionate at 10 mg/kg (n=10), pentamidine isethionate at 50 mg/kg (n=10) or a combination of pentamidine at 10 mg/kg and novobiocin at 5 mg/kg (n=10). Mice were treated two-hours post-infection to allow complete organ occupancy by the injected cells.

Figure 1A:
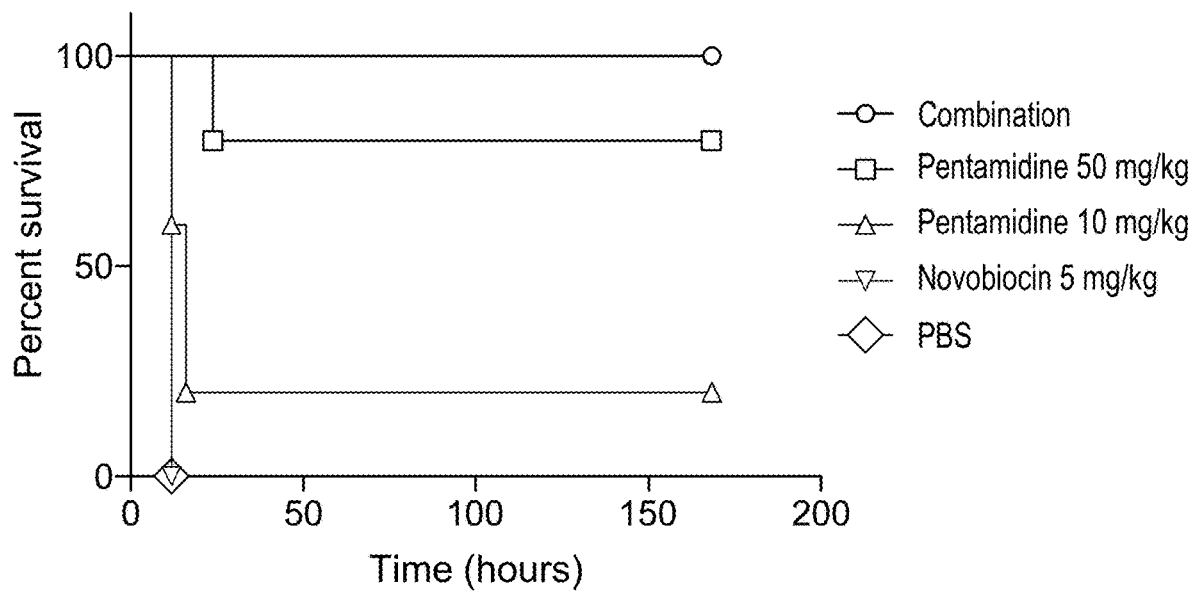
FIG. 1A shows graphically that pentamidine possesses antibacterial activity in the absence or presence of novobiocin.
Figure 1B:
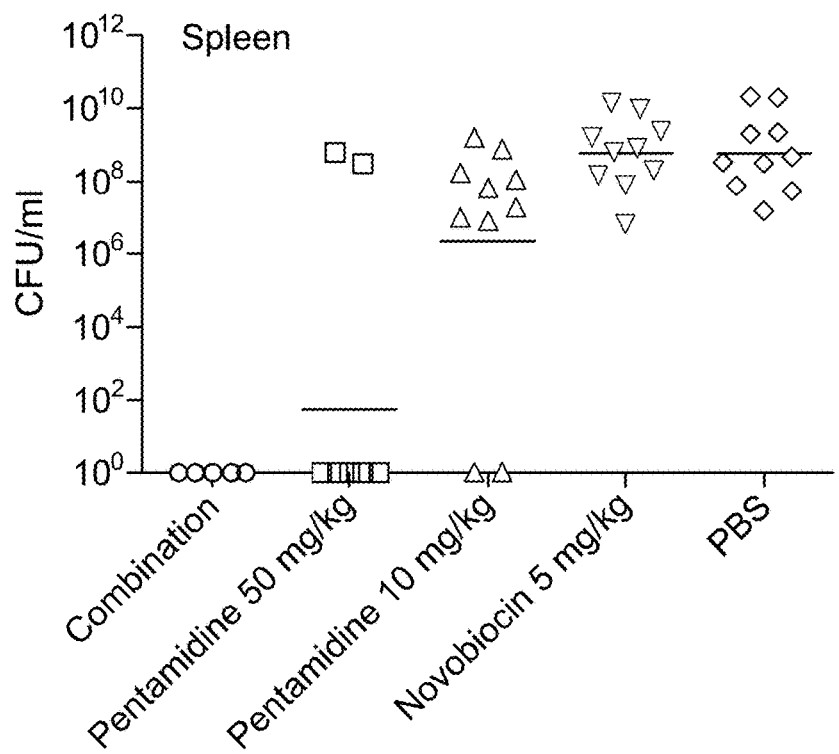
FIG. 1B shows graphically that pentamidine in the absence or presence of novobiocin causes clearance of bacteria from murine spleen.

FIG. 1A shows that when mice were treated IP with 50 mg/kg pentamidine in the absence of novobiocin, rescue in 80% of the animals was observed. FIG. 1B shows that *A. baumannii* organ load (e.g., spleen) was found to decrease seven logs as a result of pentamidine alone and found to be cleared completely as a result of the combination of pentamidene and novobiocin.

Example 2: Pentamidine Activity in Different Culture Media

Although pentamidine had relatively little or no in vitro activity in standard microbiological media against the Gram-negative organisms, *E. coli, A. baumannii, K pneumoniae, P. aeruginosa* and *B. cenocepacia*, these bacteria were highly susceptible to pentamidine when grown in a tissue culture media formulated to mimic the natural environment (Table 1). For instance, the minimum inhibitory concentration (MIC) of pentamidine isethionate against *E. coli* in the standard microbiological media Mueller Hinton Broth (MHB) of 200 µg/mL was significantly reduced in the tissue culture media formulated to mimic the natural environment to 1 µg/mL. Against *A. baumannii*, a >50-fold enhanced potency in tissue culture media formulated to mimic the natural environment was observed. Potent activity was also observed against Gram-positive organisms, such as *S. aureus*.

TABLE 1

Effects of pentamidine isethionate

|  | MHB (µg/mL) | Tissue culture media formulated to mimic the natural environment (µg/mL) |
|---|---|---|
| *Escherichia coli* | 200 | 1.5 |
| *Acinetobacter baumannii* | 100 | 12.5 |
| *Klebsiella pneumoniae* | >200 | 12.5 |
| *Pseudomonas aeruginosa* | >200 | 12.5 |
| *Burkhloderia cenocepacia* | >200 | 12.5 |
| *Burkhloderia multivorans* | >200 | 12.5 |
| *Enterococcus faecalis* | 25 | 3.1 |
| *Staphylococcus aureus* | 12.5 | <0.1 |

Example 3: Sodium Bicarbonate Potentiated the Activity of Pentamidine, in a Dose-Dependent Manner, Against *E. coli*

Figure 2:
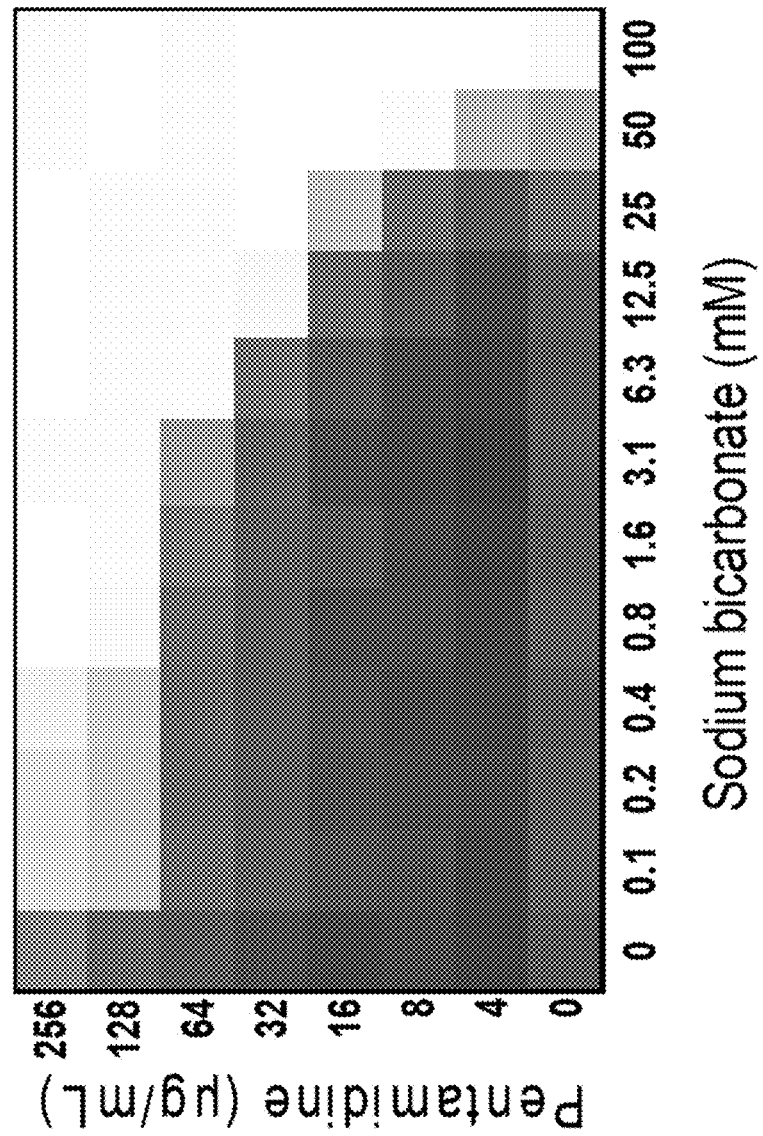
FIG. 2 shows results of checkerboard microdilution assays and demonstrates, in an illustrative embodiment, the effect of added sodium bicarbonate on pentamidine activity against *E. coli*. A synergistic interaction is observed. The extent of inhibition of bacterial growth in the checkerboard is shown as a heat plot, such that the darkest checkerboard square represents full bacterial growth.

The components of the tissue culture media formulated to mimic the natural environment were deconvoluted and tested at varying concentrations to assess their individual effects on the antibacterial activity of pentamidine. Most notably, sodium bicarbonate, which is present at physiological concentrations (25 mM) in the tissue culture media formulated to mimic the natural environment, and absent in standard microbiological media, greatly potentiated the activity of pentamidine isethionate, in a dose-dependent manner, against *E. coli* (FIG. 2). The ability of bicarbonate to potentiate the activity of pentamidine largely reconciled the paradox between the lack of activity observed in standard media in vitro and the significant in vivo activity of pentamidine as a single agent. Importantly, bicarbonate plays a central position in mammalian physiology and is ubiquitously present in the body.

Table 2 shows the effect of various salts on the antibacterial activity of pentamidine against *S. aureus*. Shown are the Fractional Inhibitory Concentration (FIC) indexes from the combination of pentamidine with each salt where FICI≤0.5 represents synergy, =1-2 additivity and >4 antagonism. Through the testing of various salts, with differing ionic strengths and other differing properties, on the activity of pentamidine, it was observed that sodium bicarbonate, was unique and provided the greatest influence on the activity of pentamidine. The sodium counterion did not contribute to the potentiation of pentamidine, as equally potent synergy was observed with varying salts of bicarbonate.

TABLE 2

Effects of various salts on the antibacterial activity of pentamidine isethionate against *S. aureus*

|  | FIC Index (with pentamidine in *S. aureus*) |
|---|---|
| Sodium bicarbonate ($NaHCO_3$) | 0.31 |
| Ammonium bicarbonate ($NH_4HCO_3$) | 0.28 |
| Sodium bromide (NaBr) | 2 |
| Sodium fluoride (NaF) | 1 |
| Sodium acetate ($C_2H_3NaO_2$) | 2 |
| Sodium sulfate ($Na_2SO_4$) | 2 |
| Sodium chloride (NaCl) | 2 |
| Isethionic acid ($C_2H_6O_4S$) | 2 |
| Boric acid ($H_3BO_3$) | 1 |
| Sodium nitrate ($NaNO_3$) | 2 |

TABLE 2-continued

Effects of various salts on the antibacterial activity of pentamidine isethionate against S. aureus

| | FIC Index (with pentamidine in S. aureus) |
|---|---|
| Sodium phosphate (NaH$_2$PO$_4$) | >8 |
| Potassium phosphate (KH$_2$PO$_4$) | >8 |

FIC index = FIC$_{salt}$ + FIC$_{pentamidine}$
Fractional Inhibitory Concentration (FIC) = [Y]/MIC$_X$, where [Y] is the lowest inhibitory concentration of drug in the presence of the co-drug.

Example 4: The Impact of Pentamidine Isethionate on the Proton Motive Force of E. coli MC1061

Fluorescence spectroscopy using the membrane-potential sensitive dye 3,3'-dipropylthiadicarbocyanine iodide was used to measure pentamidine's ability to dissipate transmembrane potential. E. coli MC1061 cells were washed twice and suspended in a buffer containing 20 mM glucose and 5 mM HEPES (pH 7.2). Final resuspension was diluted to an optical density at 600 nm of 0.085. DiSC$_3$(5) was added at a final concentration of 1 and the dye was left to stabilize (1 hr at 37° C.). Compounds were then injected at concentrations equivalent to their MIC. Fluorescent traces were measured in a fluorimeter (Photon Technology International) at the excitation and emission wavelengths of 622 and 660 nm, respectively.

Figure 3B:
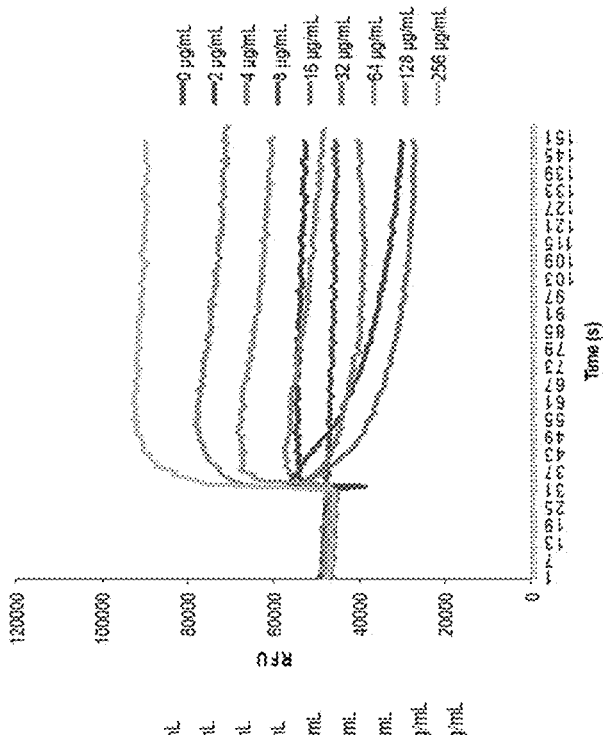
FIG. 3A and FIG. 3B show the dissipation of bacterial membrane potential by pentamidine without (FIG. 3A) or with (FIG. 3B) the addition of sodium bicarbonate.
Figure 3A:
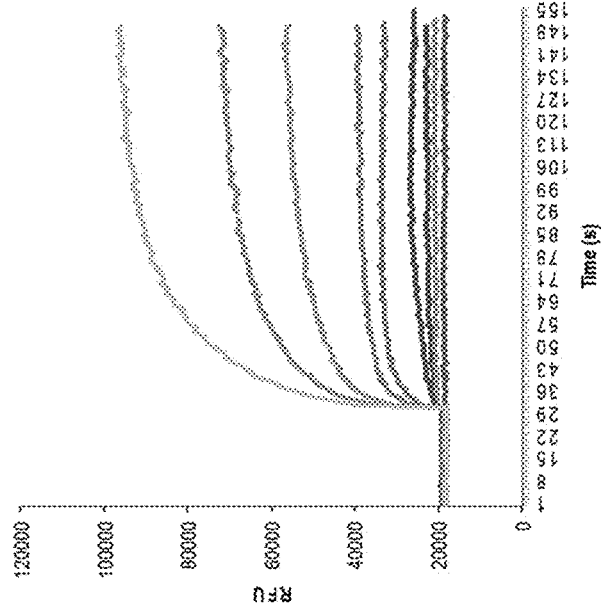

It was reasoned that the much-reduced MIC of pentamidine in the presence of an ionic milieu reminiscent of the in vivo environment might indicate an alternate mode of action than observed in standard media. Recognizing that the ability of pentamidine to perturb the outer membrane was retained in standard microbiological media, it was queried whether the ionic environment of the host might confer on pentamidine additional activity against the cytoplasmic membrane. To test this, the impact of pentamidine on the proton motive force (PMF) of E. coli was investigated. Fluorescence spectroscopy using the membrane-potential sensitive dye 3,3'-dipropylthiadicarbocyanine iodide revealed that pentamidine dissipates transmembrane potential. Briefly, due to the potential gradient, the dye is taken up by bacteria and accumulation in the membrane leads to a decrease in fluorescence intensity due to self-quenching. A subsequent increase in fluorescence intensity is observed only if the dye is displaced into the solution as a result of dissipation of the membrane potential. Pentamidine dissipated the membrane potential of E. coli whether grown in standard growth media or when supplemented with 25 mM sodium bicarbonate (FIG. 3A, FIG. 3B). While not wishing to be limited by theory, the observation that pentamidine is synergistic with sodium bicarbonate may be related to its ability to dissipate the psi component of PMF ($\Delta\psi$), whereas sodium bicarbonate can dissipate the pH gradient leading to a complete collapse of PMF.

Figure 4B:
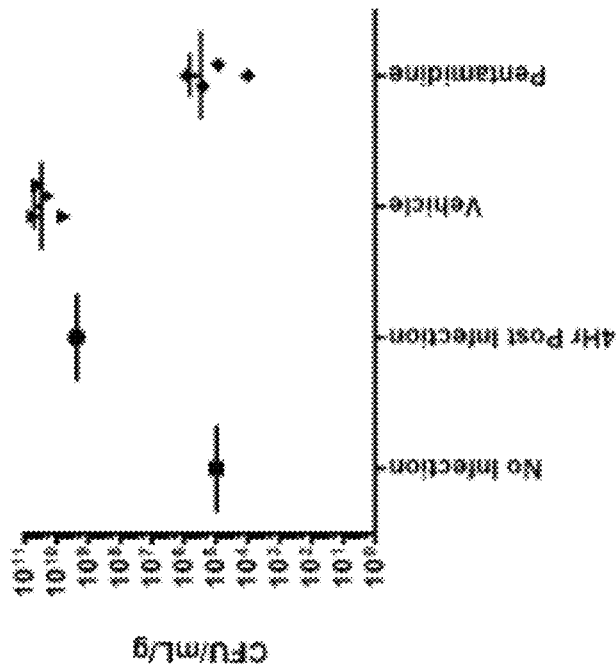
FIG. 4A and FIG. 4B graphically demonstrate bacterial load following *A. baumannii* (FIG. 4A) or MRSA (FIG. 4B) infection in tape-stripped mice, with and without pentamidine topical treatment.
Figure 4A:
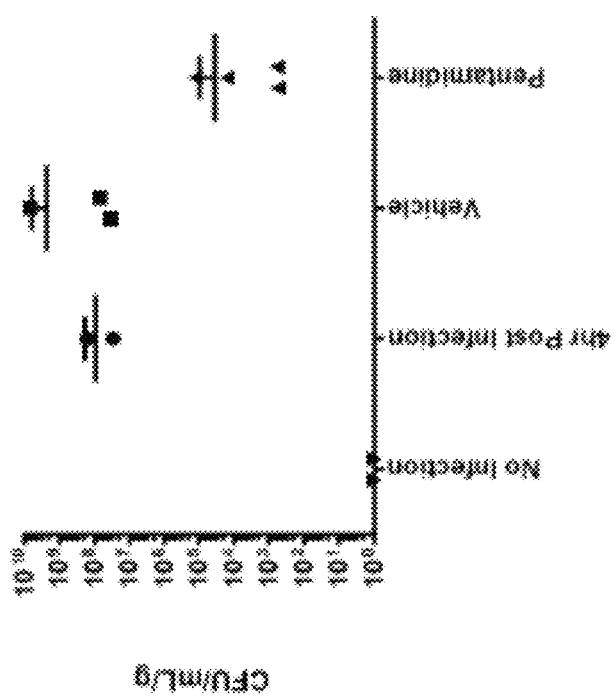
Figure 5:
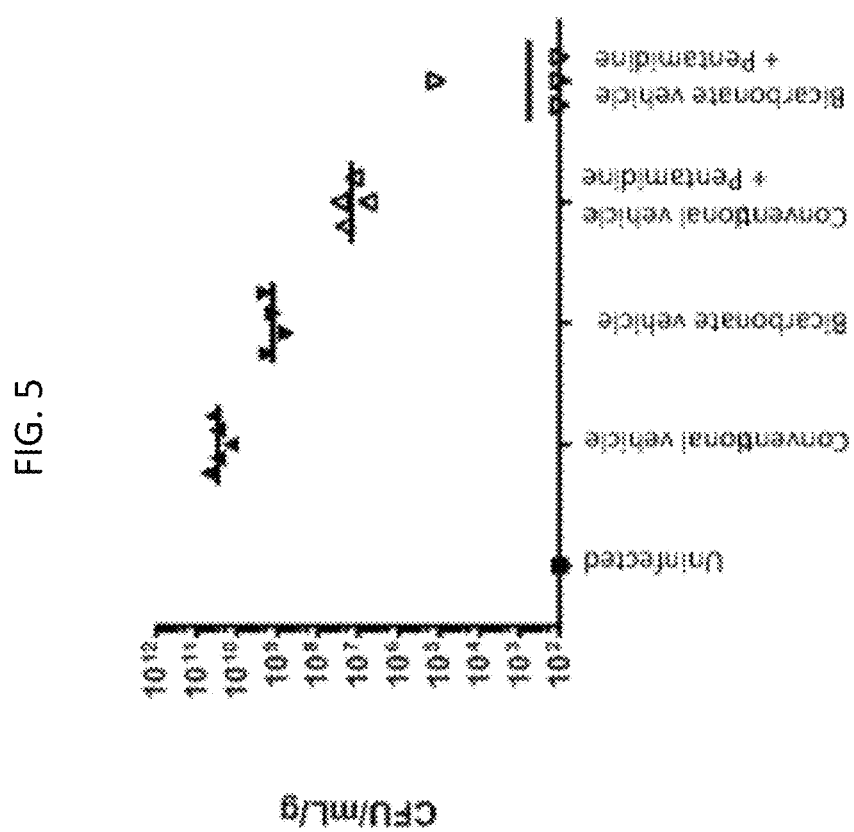
FIG. 5 graphically shows the effect of a topical pentamidine-sodium bicarbonate formulation on bacterial load following MRSA infection in tape-stripped mice.

Example 5: Pentamidine Isethionate is Effective for Inhibiting the Growth of Both Gram-Negative and Gram-Positive Bacteria The efficacy of pentamidine as a prophylactic or therapeutic agent was demonstrated in a variety of superficial skin infection models. In this model, an infection is established by disrupting the skin barrier through partial removal of the epidermal layer by stripping with adhesive tape and with subsequent application of the pathogen. Tape-stripped mice infected with 4×10$^6$ CFU/mL A. baumannii (FIG. 4A) or 4×10$^6$ CFU/mL methicillin-resistant Staphylococcus aureus (MRSA) USA-300 (FIG. 4B). The No Infection group (n=1) shows the natural bacterial load after tape-stripping with no inoculum applied. Twenty µL of 0.5% Pentamidine in 1.9% Boric Acid, pH 7.0 was applied to the wound area 4,5,6,7,8,9, and 19,20,21,22,23,24 hours post infection (n=4). This treatment regime was also conducted for the Vehicle (1.9% Boric Acid, pH 7) as a control (n=4). Tissue samples were collected at 25 hr post-infection (FIG. 4A) and 28 hr post-infection (FIG. 4B). In the A. baumannii skin infection model, where mice were treated with 0.5% pentamidine, a 4-log reduction in CFU/mL compared to vehicle-treated mice was observed (FIG. 4A). In a S. aureus skin infection model, 0.5% pentamidine treatment caused a 5-log reduction in CFU/mL (FIG. 4B). Further, addition of bicarbonate in the solution increased the antibacterial efficacy of pentamidine in clearing an MRSA infection (pentamidine was applied as a topical 0.5% aqueous solution on skin with or without bicarbonate (50 mM)). (FIG. 5). Overall, pentamidine offers an effective, localized and well-tolerated topical approach for both Gram-negative and Gram-positive bacteria.

Figure 6A:
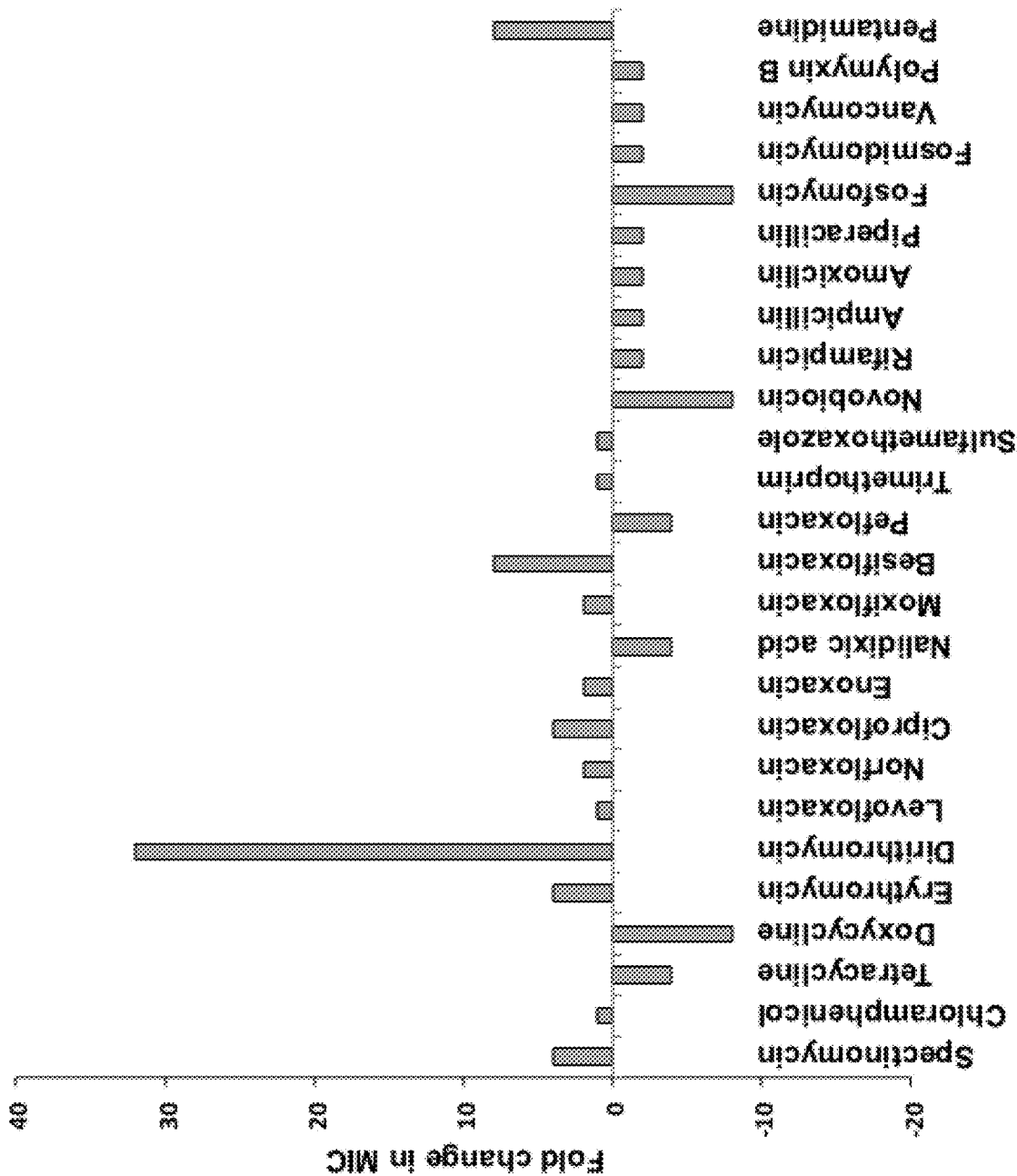
FIG. 6A graphically shows potentiation or suppression of illustrative antibiotic agents against *E. coli* in the presence of 25 mM sodium bicarbonate.
Figure 6B:
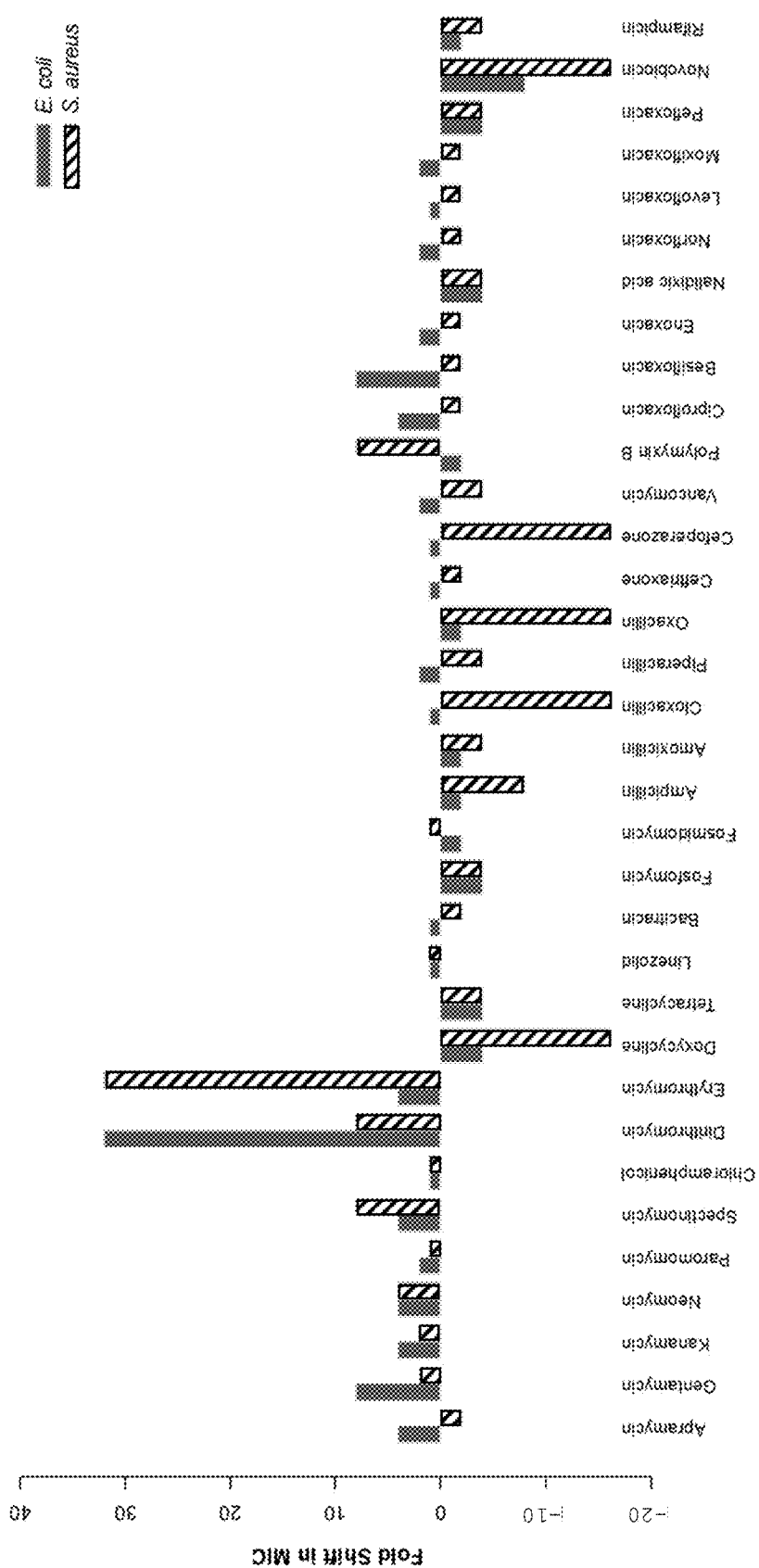
FIG. 6B shows that bicarbonate affects the activity of illustrative antibiotic agents against *E. coli* and *S. aureus*.

Example 6: The Effect of Addition of Sodium Bicarbonate on Conventional Antibiotic Agents The MICs of the antibiotic agents listed in FIG. 6A were determined in MHB media and compared to the MIC in MHB supplemented with physiological concentrations of sodium bicarbonate (25 mM) (MHB+25 mM Sodium bicarbonate). Results of different experiments are shown in FIG. 6A and FIG. 6B. Fold enhancement in MICs in the media supplemented with sodium bicarbonate is represented by a positive fold, whereas suppression of activity is represented by a negative fold.

FIG. 6A shows the fold changes in Escherichia coli in one experiment. The trends were similar in the Gram-positive Staphylococcus aureus. Additional data are shown in FIG. 6B and Table 3: the fold enhancement in the MIC for a variety of antibiotic agents in standard microbiological media relative to media supplemented with 25 mM sodium bicarbonate is shown for E. coli and S. aureus. As shown in FIG. 6B, eight classes of antibiotic agents investigated had appreciably altered activities in the presence of 25 mM sodium bicarbonate. In FIG. 6B, the MICs of the listed antibiotic agents were determined in MHB media and compared to the MIC in MHB supplemented with physiological concentrations of sodium bicarbonate (25 mM). Fold enhancement in MICs in the media supplemented with sodium bicarbonate is represented by a positive value, whereas suppression of activity is represented by a negative value. Shown are the fold changes in E. coli (solid) and fold changes in S. aureus (checkered).

With a few exceptions, these Gram-negative and Gram-positive bacteria behaved similarly. Of the antibiotic agents tested, the antibacterial activity of some fluoroquinolones, macrolides, and aminoglycosides was enhanced. The activity of polymyxin B was enhanced strictly in S. aureus. In contrast, the antibacterial activity of other fluoroquinolones, various cell wall active drugs, tetracyclines, fosfomycin and novobiocin was suppressed in the presence of bicarbonate. The antibacterial effect on other classes such as chloramphenicol, linezolid, the antifolate drugs, trimethoprim and sulfamethoxazole, remained largely unchanged.

TABLE 3

MIC of various antibiotic agents against *E. coli* and *S. aureus* in MHB in the absence of sodium bicarbonate ("MHB−") vs MHB in the presence of 25 mM sodium bicarbonate ("MHB+").

Figure 6C:
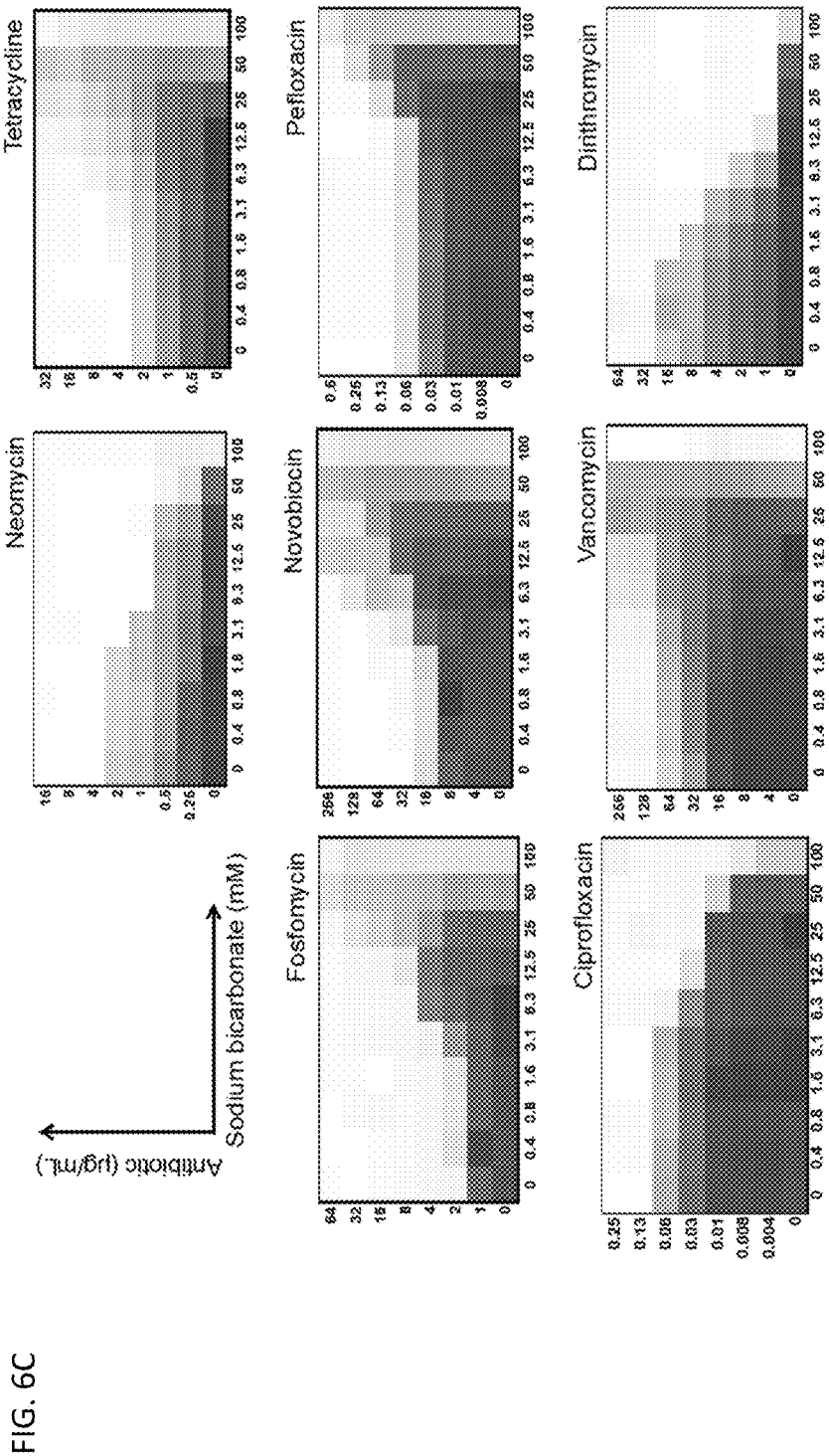
FIG. 6C shows microdilution checkerboard analyses for illustrative antibiotic agents in the presence of sodium bicarbonate against *E. coli*. The extent of inhibition of bacterial growth in each checkerboard is shown as a heat plot, such that the darkest checkerboard square represents full bacterial growth.

|  | *E. coli* | | | *S. aureus* | | |
| --- | --- | --- | --- | --- | --- | --- |
|  | MHB− | MHB+ | Fold | MHB− | MHB+ | Fold |
| Apramycin | 32 | 8 | 4 | 16 | 32 | −2 |
| Gentamicin | 2 | 0.25 | 8 | 2 | 1 | 2 |
| Kanamycin | 4 | 1 | 4 | 8 | 4 | 2 |
| Neomycin | 1 | 0.25 | 4 | 2 | 0.5 | 4 |
| Paromomycin | 2 | 1 | 2 | 2 | 2 | 1 |
| Spectinomycin | 16 | 4 | 4 | 64 | 8 | 8 |
| Chloramphenicol | 8 | 8 | 1 | 8 | 8 | 1 |
| Dirithromycin | 128 | 4 | 32 | 4 | 0.5 | 8 |
| Erythromycin | 128 | 32 | 4 | 32 | 1 | 32 |
| Doxycycline | 1 | 4 | −4 | 0.125 | 2 | −16 |
| Tetracycline | 1 | 4 | −4 | 0.5 | 2 | −4 |
| Linezolid | 256 | 256 | 1 | 0.625 | 0.625 | 1 |
| Bacitracin | >256 | >256 | 1 | 32 | 64 | −2 |
| Fosfomycin | 4 | 16 | −4 | 16 | 64 | −4 |
| Fosmidomycin | 16 | 32 | −2 | >64 | >64 | 1 |
| Ampicillin | 16 | 32 | −2 | 1 | 8 | −8 |
| Amoxicillin | 8 | 16 | −2 | 0.25 | 1 | −4 |
| Cloxacillin | 256 | 256 | 1 | 0.031 | 0.5 | −16 |
| Piperacillin | 2 | 1 | 2 | 0.25 | 1 | −4 |
| Oxacillin | 256 | >256 | −2 | 0.0625 | 1 | −16 |
| Ceftriaxone | 0.625 | 0.625 | 1 | 4 | 16 | −4 |
| Cefoperazone | 0.125 | 0.125 | 1 | 0.25 | 4 | −16 |
| Vancomycin | 256 | 256 | 1 | 1 | 4 | −4 |
| Polymyxin B | 0.25 | 0.5 | −2 | 256 | 32 | 8 |
| Ciprofloxacin | 0.0625 | 0.0156 | 4 | 0.5 | 1 | −2 |
| Besifloxacin | 0.25 | 0.0313 | 8 | 0.125 | 0.25 | −2 |
| Enoxacin | 0.25 | 0.125 | 2 | 1 | 2 | −2 |
| Nalidixic acid | 2 | 8 | −4 | >8 | 32 | −4 |
| Norfloxacin | 0.125 | 0.0625 | 2 | 0.5 | 1 | −2 |
| Levofloxacin | 0.0313 | 0.0313 | 1 | 0.5 | 1 | −2 |
| Moxifloxacin | 0.0313 | 0.0156 | 2 | 0.125 | 0.0625 | 2 |
| Pefloxacin | 0.125 | 0.5 | −4 | 0.5 | 2 | −4 |
| Novobiocin | 32 | >256 | −8 | 0.031 | 0.5 | −16 |
| Rifampicin | 32 | 64 | −2 | 0.0078 | 0.031 | −4 |

Where antibiotic agents were potentiated or suppressed, follow-up studies using systematic microbroth checkerboard techniques were completed to assess the dose-dependence of the interaction (FIG. 6C). Indeed, in all cases, enhancement or suppression was further pronounced with increasing concentrations of sodium bicarbonate. FIG. 6C shows representative antibiotic agents whose activity was altered in the presence of 25 mM sodium bicarbonate. The extent of inhibition is shown as a heat plot, such that the darkest checkerboard square represents full bacterial growth.

Example 7: Sodium Bicarbonate Diminishes the Uptake of Tetracycline in *E. coli*

Figure 7:
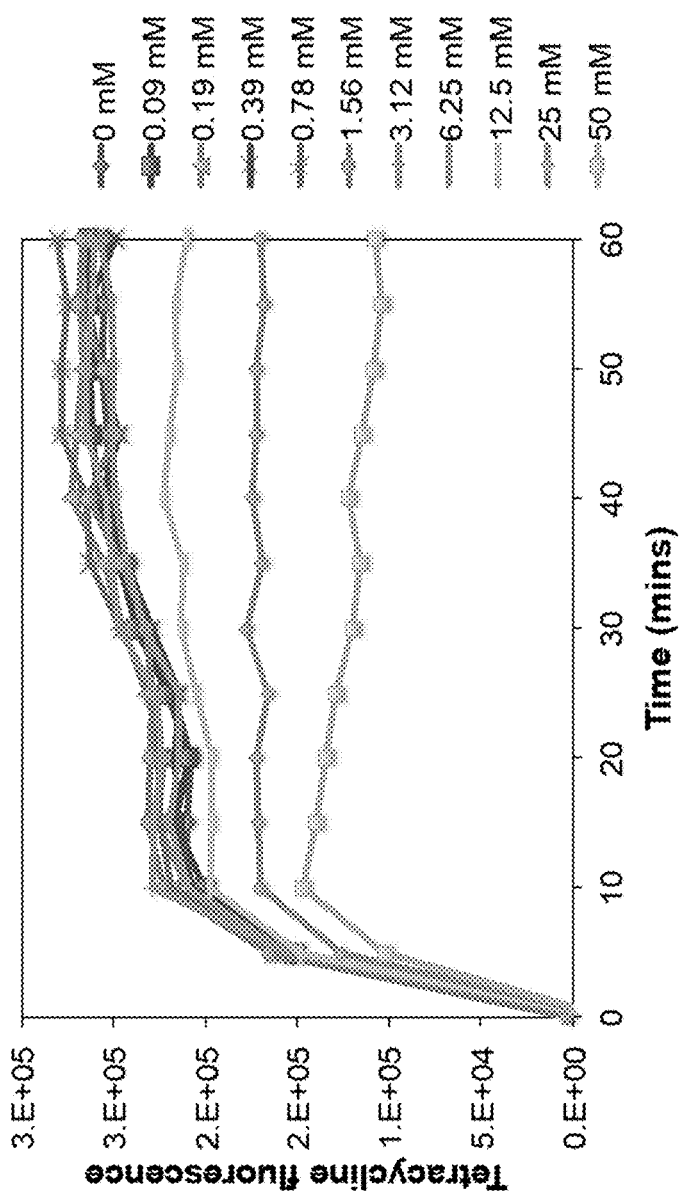
FIG. 7 is a line graph showing suppression of tetracycline entry in *E. coli* in the presence of varying concentrations of sodium bicarbonate.
Figure 11A:
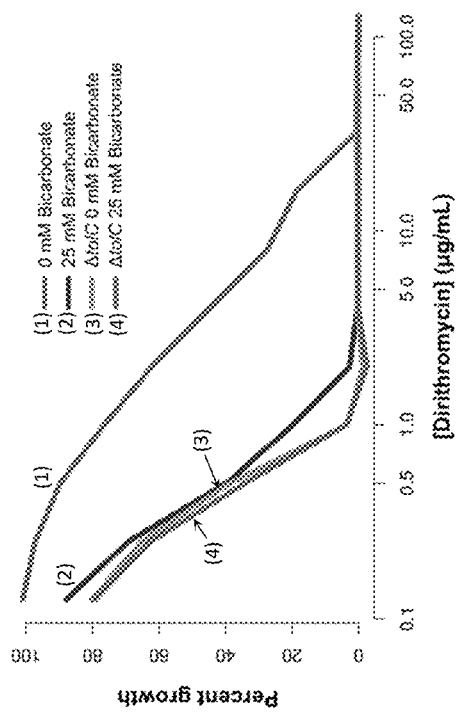
FIGS. 11A-11C are line graphs showing that bicarbonate dissipates pH gradient across the cytoplasmic membrane affecting the activity of antibiotic agents on *E. coli* (FIGS. 11A-11B) or *E. coli* ΔtolcC (FIG. 11C).

The concentration of tetracycline was 125 µg/ml, and concentration of sodium bicarbonate was as indicated in FIG. 7. Tetracycline uptake was assayed by monitoring the fluorescence enhancement of tetracycline when it enters the cell. Averages of duplicate experiments are shown in FIG. 7. In a similar experiment, a direct test of the cellular uptake of tetracycline revealed that that suppression observed was due to inhibition of tetracycline uptake on addition of bicarbonate (FIG. 11A). In FIG. 11A, sodium bicarbonate diminished the uptake of tetracycline in *E. coli*. Concentration of tetracycline was 125 µg/ml, and concentration of sodium bicarbonate was as indicated. Tetracycline uptake was assayed by monitoring the fluorescence enhancement of tetracycline when it enters the cell. Averages of triplicate experiments are shown.

Example 8: Bicarbonate Potentiates the Action of Dirithromycin

Figure 8A:
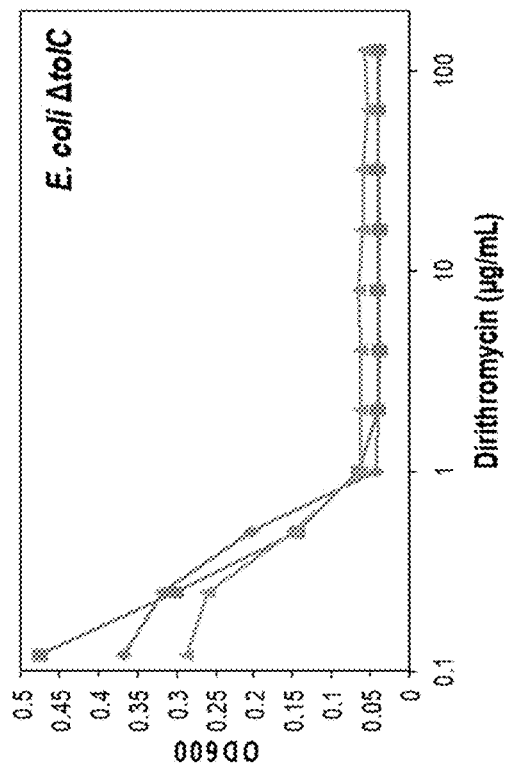
FIG. 8A is a line graph showing potentiation of dirithromycin in the presence of 25 mM sodium bicarbonate.
Figure 8B:
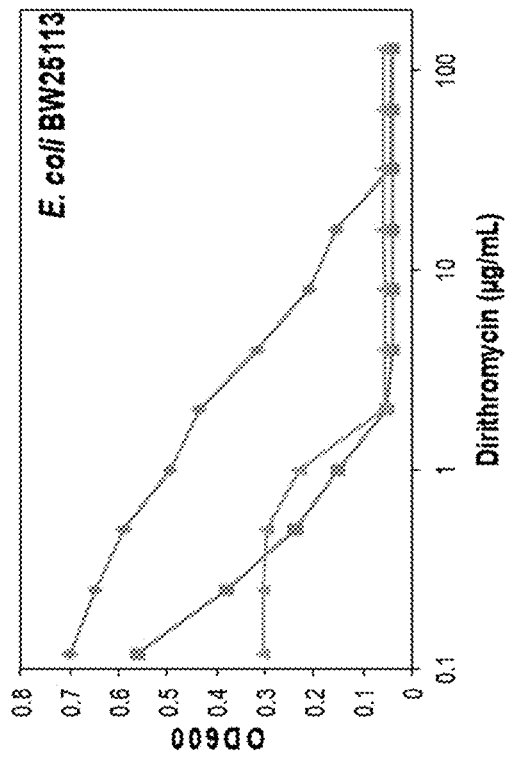
FIG. 8B shows disappearance of potentiation in an *E. coli* mutant lacking efflux pump to/C.

Results shown in FIG. 8A show that a growth inhibitory concentration of the macrolide dirithromycin is potentiated in the presence of sodium bicarbonate in wild-type *E. coli* and in FIG. 8B, show potentiation by sodium bicarbonate disappears in a strain deficient for the main efflux pumps *E. coli* ΔtolC.

The enhancement of dirithromycin by sodium bicarbonate was further assessed for the pathogens *Acinetobacter baumannii*, *Klebsiella pneumoniae* and *Pseudomonas aeruginosa* (FIG. 8C, Panels a-c). FIG. 8C, Panels a-c show the combination of the macrolide, dirithromycin, and sodium bicarbonate against multi-drug resistant clinical isolates of (a) *Acinetobacter baumannii* (b) *Klebsiella pneumoniae* and (c) *Pseudomonas aeruginosa*. In all cases, bicarbonate was a potentiator of the action of this macrolide antibiotic.

Example 9: Bicarbonate is Responsible for the Enhancements Observed

Whether the chemical bicarbonate was responsible for the enhancements observed in the above examples was assessed. It was observed that the activity was not due to simply an effect on pH. Test media were pH-adjusted upon addition of sodium bicarbonate for all studies reported herein. Of note, sodium bicarbonate at physiological concentration (25 mM) produced media with a pH typical of standard susceptibility testing conditions (Table 4).

TABLE 4 pH of MHB media amended with various concentrations of sodium bicarbonate, prior to pH-adjusting to 7.4.

| Concentration (mM) | pH |
| --- | --- |
| 0 | 7.42 |
| 1.56 | 7.42 |
| 3.12 | 7.42 |
| 6.25 | 7.43 |
| 12.5 | 7.47 |
| 25 | 7.53 |
| 50 | 7.61 |
| 100 | 7.71 |

Further, using dirithromycin, many equimolar organic salts were tested, with differing ionic strengths and steric properties, and none had impact on antibacterial activity, ruling out osmotic-mediated mechanisms (Table 5). Lastly, sodium did not contribute to the potentiation of dirithromycin, as equally potent synergy was observed with other salts of bicarbonate (Table 5).

TABLE 5

Minimum inhibitory concentration of dirithromycin in the presence of various salts at 25 mM against *E. coli*. In all cases, pH was adjusted to 7.4.

| Salt | Formula | MIC (µg/mL) |
| --- | --- | --- |
| Control | — | 128 |
| Sodium bicarbonate | $NaHCO_3$ | 4 |
| Sodium bromide | NaBr | 128 |
| Sodium chloride | NaCl | 128 |
| Sodium fluoride | NaF | 128 |
| Sodium nitrate | $NaNO_3$ | 128 |
| Sodium acetate | $C_2H_3NaO_2$ | 64 |
| Sodium sulfate | $Na_2SO_4$ | 128 |

TABLE 5-continued

Minimum inhibitory concentration of dirithromycin in the presence of various salts at 25 mM against *E. coli*. In all cases, pH was adjusted to 7.4.

| Salt | Formula | MIC (μg/mL) |
|---|---|---|
| Isethionic acid | $C_2H_6O_4S$ | 128 |
| Boric acid | $H_3BO_3$ | 128 |
| Sodium phosphate | $NaH_2PO_4$ | >128 |
| Potassium phosphate | $KH_2PO_4$ | >128 |
| Ammonium bicarbonate | $KHCO_3$ | 8 |
| Potassium bicarbonate | $NH_4HCO_3$ | 4 |

Example 10: Minimum Inhibitory Concentration of Pentamidine Isethionate Against *Saccharomyces cerevisiae*

Figure 9:
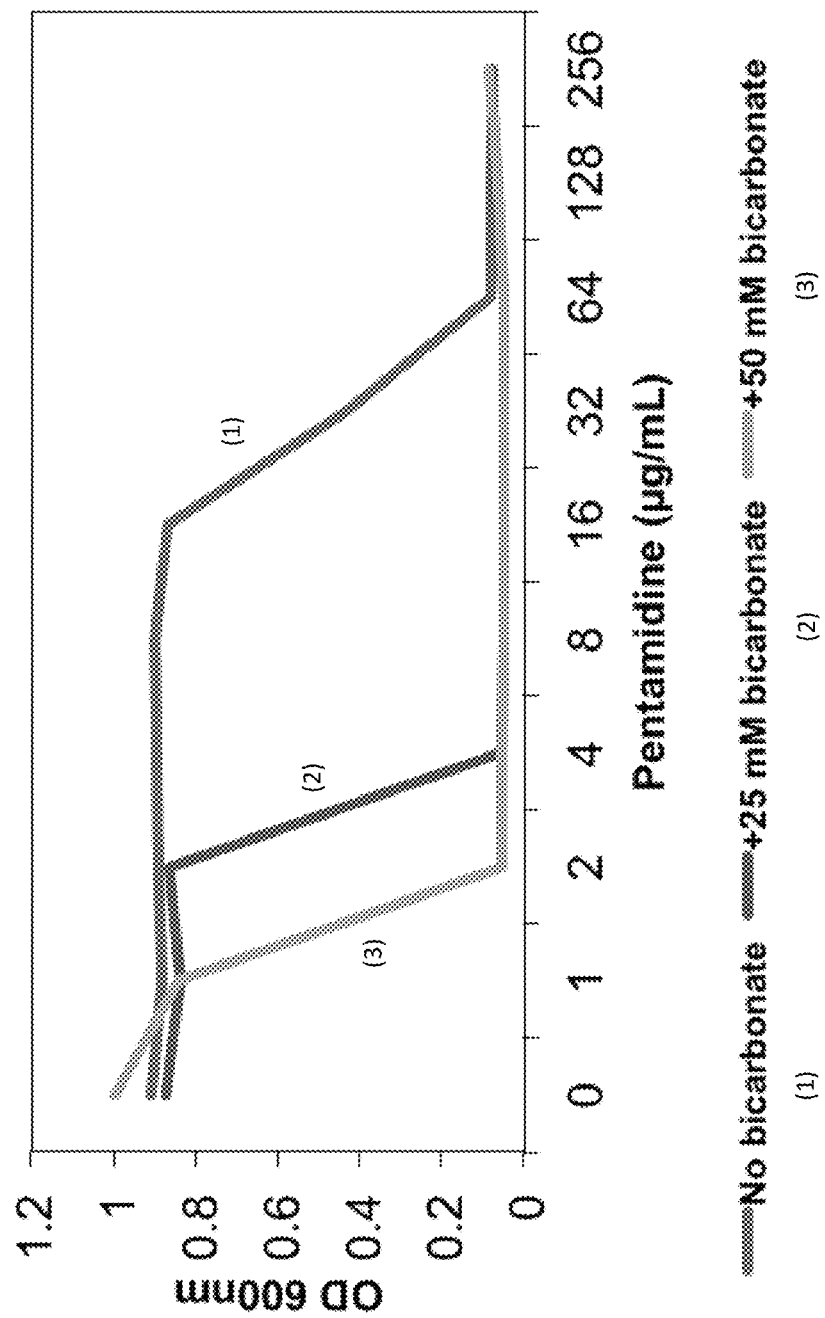
FIG. 9 is a line graph showing that the MIC of pentamidine against *Saccharomyces cerevisiae* is reduced from 256 µg/mL to 4 µg/mL in the presence of 25 mM sodium bicarbonate and to 2 µg/mL in the presence of 50 mM sodium bicarbonate.

An overnight culture of *Saccharomyces cerevisiae* was diluted 1:5,000 into fresh YPD medium, supplemented with 0, 25 mM or 50 mM sodium bicarbonate and tested against two-fold serial dilutions of pentamidine. Plates were incubated 24 hours and optical density read at 600 nm FIG. 9 shows that the MIC of pentamidine is reduced from 256 μg/mL to 4 μg/mL in the presence of 25 mM sodium bicarbonate and to 2 μg/mL in the presence of 50 mM sodium bicarbonate.

Example 11: Physiological Concentrations of Bicarbonate Enhance the Antibacterial Activity of Various Chemical Factors Involved in Innate Immunity The influence of sodium bicarbonate (pH 7.4) on the in vitro antibacterial activity of various secretory molecules and cellular components that make up innate immunity against bacterial pathogens was investigated. Specifically, the ability of sodium bicarbonate, at the sub-MIC but physiological concentration of 25 mM, to potentiate the activity of various mediators of host defense, including defensins and cathelicidins, whose family members make up the principal components of innate immunity in vertebrates (Zasloff, M. N Engl J Med 2002, 347: 1199-1200), was assessed.

Sodium bicarbonate itself exhibited antibacterial activity against *E. coli*, *Staphylococcus aureus*, and other clinically relevant pathogens, with minimum inhibitory concentration (MIC) values ranging from 50-100 mM (Table 6).

TABLE 6

MIC of sodium bicarbonate against various pathogens.

| Organism | MIC (mM) |
|---|---|
| *Escherichia coli* | 100 |
| *Staphylococcus aureus* | 50-100 |
| *Klebsiella pneumoniae* | 100 |
| *Acinetobacter baumannii* | 50 |
| *Pseudomonas aeruginosa* | >100 |
| *Enterococcus faecium* | 50-100 |

Figure 10:
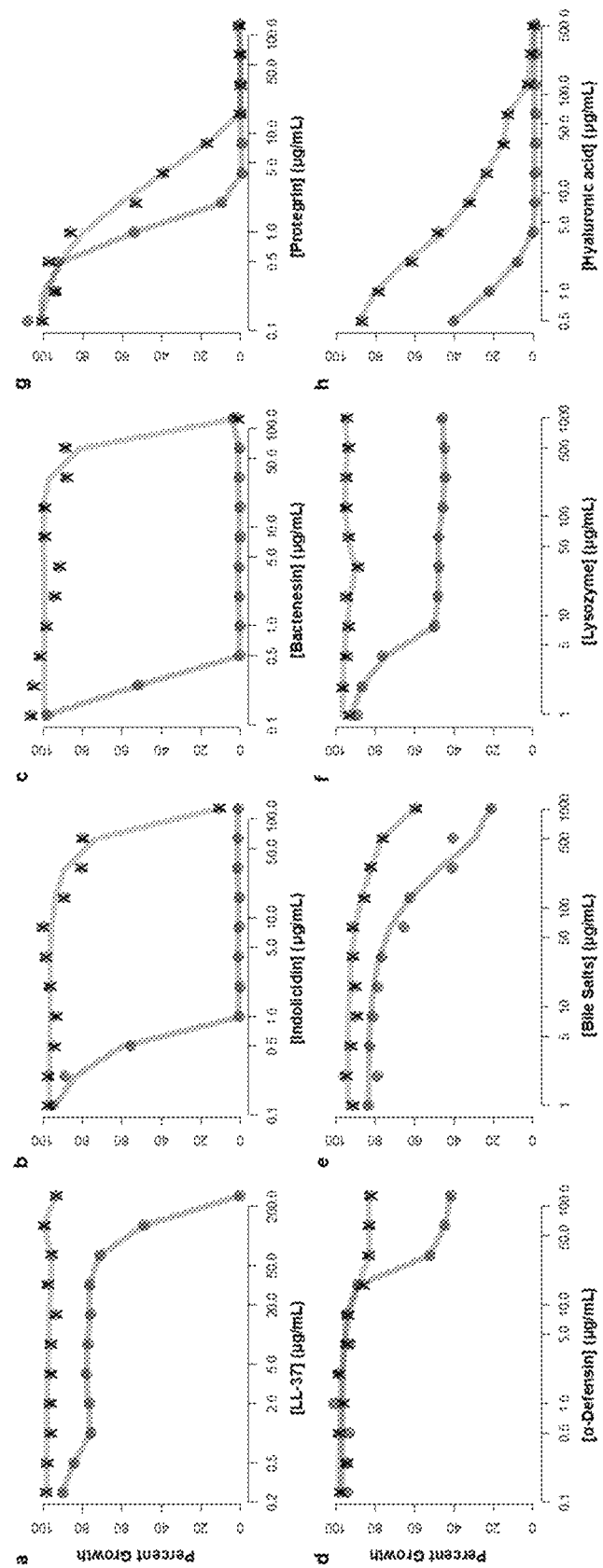
FIG. 10, Panels a-h, are line graphs showing that physiological concentrations of bicarbonate enhance the antibacterial activity of various chemical factors involved in innate immunity. Shown are potency analyses of various components against *E. coli* in MHB (line with Xs) and MHB supplemented with 25 mM sodium bicarbonate (line with circles) for Panel a, LL-37; Panel b, indolicidin; Panel c, bactenesin; Panel d, alpha-defensin; Panel e, bile salts; Panel f, lysozyme; Panel g, protegrin; and Panel h, hyaluronic acid.

Shown in FIG. 10, Panels a-h are potency analyses of various components against *E. coli* in MHB (line with Xs) and MEM supplemented with 25 mM sodium bicarbonate (line with circles) for a, LL-37; b, indolicidin; c, bactenesin; d, alpha-defensin; e, bile salts; f, lysozyme; g, protegrin; and h, hyaluronic acid. Averages of triplicate experiments are shown.

The antimicrobial activity of alpha-defensin and LL-37 were enhanced on average 4 to 8-fold against *E. coli* (FIG. 10, Panels a,e) and *S. aureus* (Table 7). Other antimicrobial peptides, such as indolicidin and bactenesin, were also potentiated in the presence of bicarbonate, 128- and 256-fold, respectively against *E. coli* (FIG. 10, Panels b,c), and 16- and 256-fold, respectively against *S. aureus* (Table 7). Also enhanced in the presence of bicarbonate, was the activity of the porcine leukocyte protegrin (8-fold in both *E. coli* and *S. aureus*) (FIG. 10, Panel d; Table 7). Additionally, a physiological concentration of sodium bicarbonate enhanced the inhibitory activity of other innate immunity chemical factors such as lysozyme and bile salts against *E. coli* (FIG. 1, Panels f,g). The innate immunity chemical barrier, hyaluronic acid, which is ubiquitously expressed in the extracellular matrix of all vertebrate tissues was also potentiated in the presence of sodium bicarbonate, 64-fold in both *E. coli* and *S. aureus* (FIG. 10, Panel h; Table 7). It is noted that common among these components of innate immunity is their ultimate action on the cytoplasmic membrane causing membrane depolarization.

TABLE 7

MIC of various components of innate immunity in MHB vs MHB + 25 mM sodium bicarbonate against *S. aureus* (Newman strain) (MSSA)

| Component | MIC (μg/mL) in MHB | MIC (μg/mL) in MHB + 25 mM bicarbonate |
|---|---|---|
| LL-37 | 128 | 32 |
| Indolicidin | 128 | 8 |
| Bactenesin | 128 | 0.5 |
| α-defensin | ND* | ND* |
| Protegrin | 32 | 4 |
| Lysozyme | >256** | >256** |
| Bile salts | 512 | 512 |
| Hyaluronic acid | 4 | 0.0625 |

*ND: not determined;
**S. aureus* is intrinsically resistant to lysozyme

Example 12: The Effects of Proton Motive Force (PMF) Perturbations on the Activity of Antibacterial Agents The proton motive force (PMF) describes the electrochemical potential at the cytoplasmic membrane that is composed of an electrical potential ($\Delta\psi$, negative inside) and a proton gradient ($\Delta pH$, acidic outside). It is known that tetracyclines penetrate bacterial cells in a $\Delta pH$-dependent manner, while positively charged aminoglycosides utilize the $\Delta\psi$ component for transport. Agents that selectively perturb either $\Delta\psi$ or $\Delta pH$ are known to prompt a compensatory increase in the other component in order to maintain PMF. The role of bicarbonate in perturbing PMF of bacteria was further assessed.

Figure 12:
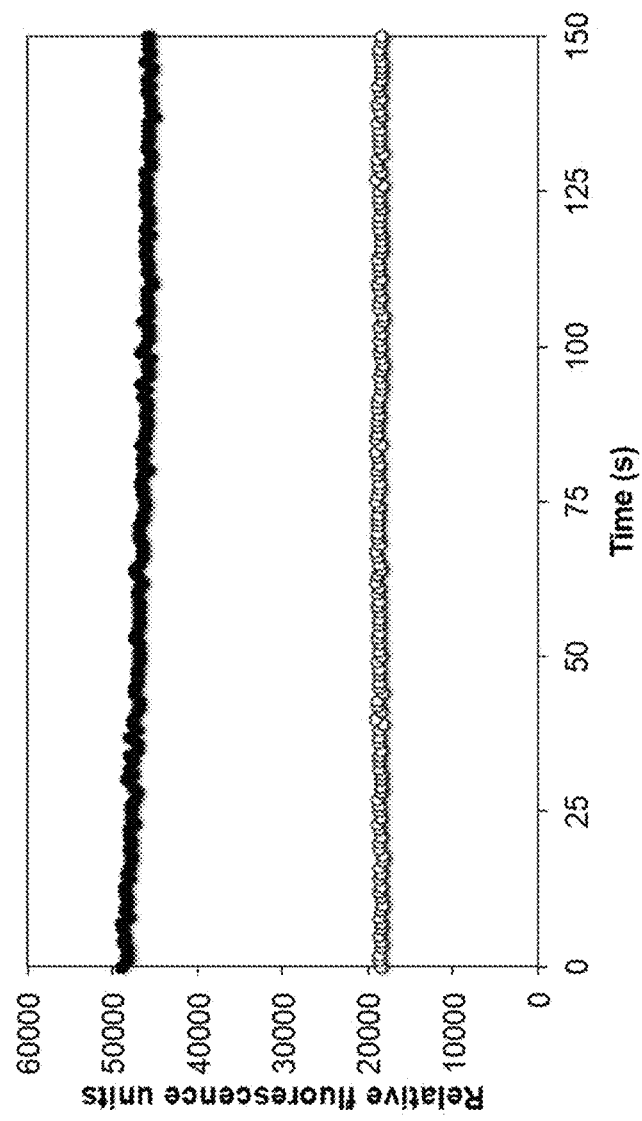
FIG. 12 is a graph showing uptake of 3,3'-dipropylthiacarbocyanine iodide, a membrane-potential sensitive dye, in *S. aureus* cells in the absence (untreated, white circles) or presence of 25 mM sodium bicarbonate (treated, black circles).

Treatment of *E. coli* with 25 mM bicarbonate led to a higher transmembrane distribution of 3,3'-dipropylthiadicarbocyanine iodide ($DiSC_3(5)$), a fluorescent probe that exhibits $\Delta\psi$-dependent membrane accumulation (FIG. 12). Without being bound to theory, this is consistent that with the observed increase in aminoglycoside activity, selective dissipation of $\Delta pH$ by sodium bicarbonate is compensated for by an increase in $\Delta\psi$ that in turn drives uptake of aminoglycosides.

Specifically, FIG. 12 shows uptake of 3,3'-Dipropylthiacarbocyanine iodide, a membrane-potential sensitive dye. *S. aureus* cells were grown to exponential phase in the absence (untreated) or presence of 25 mM sodium bicarbonate (treated), washed and loaded with 1 µM $DiSC_3(5)$. *S. aureus* treated with 25 mM sodium bicarbonate exhibited an increased uptake in the levels of $DiSC_3(5)$ as measured by fluorescence (black circles) and compared to uptake levels of untreated cells (white circles). Uptake and fluorescence was stable over time as shown in the graph.

Figure 11B:
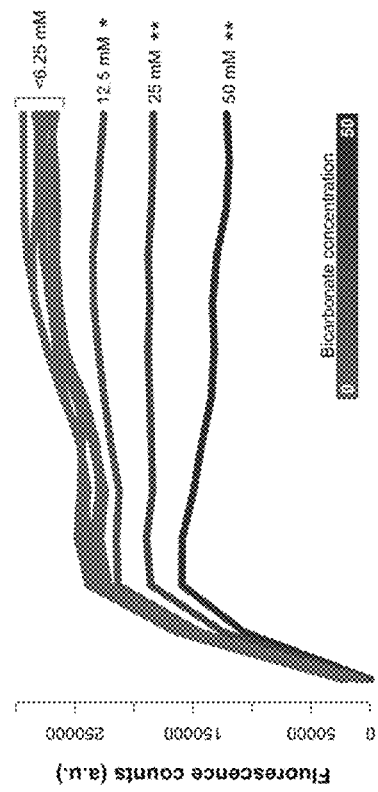
Figure 11C:
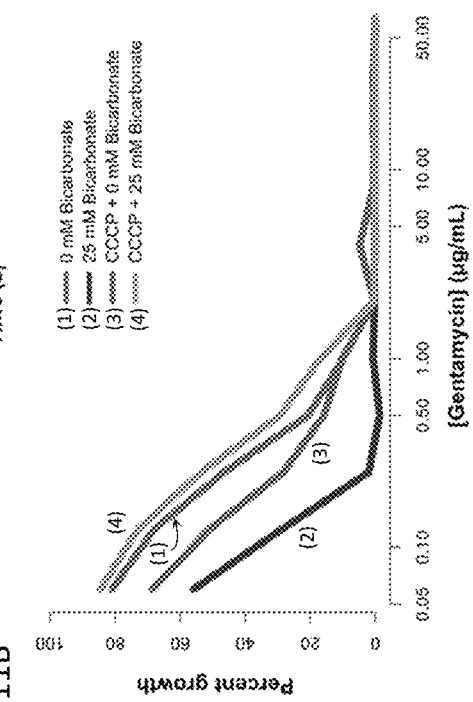

Pre-incubation of *E. coli* with the proton ionophore, carbonyl cyanide m-chlorophenyl hydrazone (CCCP; selectively targets the pH gradient of cells), prior to treatment with sodium bicarbonate and gentamicin, reversed the potentiation observed (FIG. 11, Panel b). Panel b shows that pre-treatment with CCCP abolishes the potentiation of gentamicin by sodium bicarbonate. Shown are potency analyses of gentamicin in MHB against *E. coli* (1); MHB supplemented with 25 mM sodium bicarbonate (2); CCCP pre-treated cells in MHB (3); CCCP pre-treated cells in MHB supplemented with 25 mM sodium bicarbonate (4). Averages of triplicate experiments are shown.

Taken together, these data show that sodium bicarbonate influences the entry of antibacterial agents that are driven by PMF, suppressing those that require an intact pH gradient across the cytoplasmic membrane, and enhancing those that are driven by $\Delta\psi$, such as the polycationic aminoglycosides.

Example 13: Effects of Bicarbonate on Cellular Respiration of Bacterial in the Context of Antibiotic Agents Other antibiotic agents that rely on cellular energetics for entry include fosfomycin and novobiocin. Fosfomycin is actively transported via a glycerol-3-phosphate permease where transport activity has been shown to be dependent on $\Delta pH$. Uptake of novobiocin is similarly an active transport mechanism supported by $\Delta pH$ such that uncouplers and inhibitors of respiration have been shown to reduce its cellular accumulation. Sodium bicarbonate suppressed the activity of fosfomycin and novobiocin (FIG. 6C).

Figure 13A:
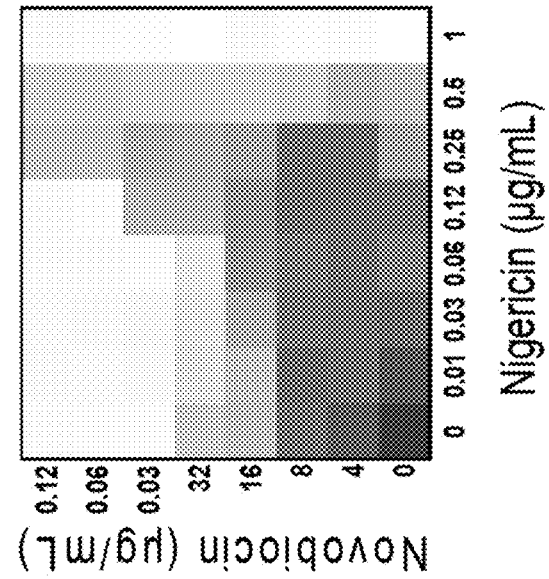
FIGS. 13A-13B show microdilution checkerboard analyses of nigericin, a protonophore, in the presence of fosfomycin (FIG. 13A) or novobiocin (FIG. 13B) leads to an antagonistic interaction with *S. aureus*. The extent of inhibition of bacterial growth in each checkerboard is shown as a heat plot, such that the darkest checkerboard square represents full bacterial growth.
Figure 13B:
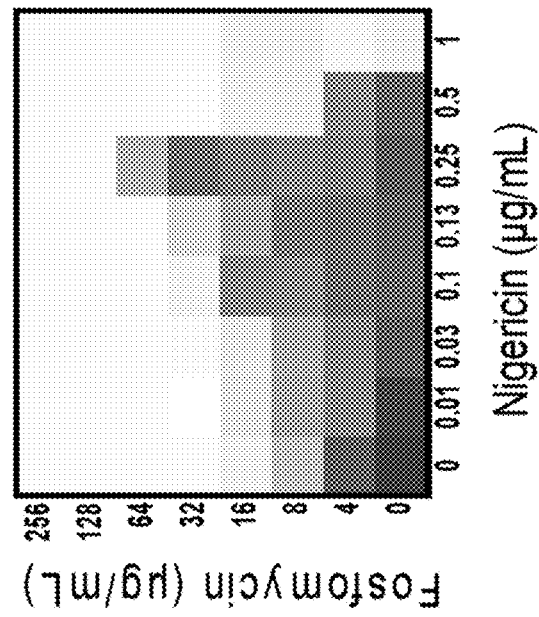

Nigericin, an ionophore that selectively dissipates the pH gradient, also suppressed the activity of fosfomycin and novobiocin (FIGS. 13A-13B). Specifically, FIG. 13A and FIG. 13B show that a combination of nigericin, a protonophore, with fosfomycin (FIG. 13A) or novobiocin (FIG. 13B) leads to antagonistic interactions against *S. aureus* (sensitive to nigericin). Shown are microdilution checkerboard analyses, where the extent of inhibition is shown as a heat plot, such that the darkest checkerboard square represents full bacterial growth.

Fluoroquinolone (FQ) antibiotic agents show a variety of responses in the presence of 25 mM sodium bicarbonate depending on their physicochemical properties and the organism in question. While convention holds that FQ uptake is a passive process, previous studies have noted that the addition of the protonophore CCCP results in increased uptake of some FQs, suggesting a role for the $\Delta\psi$ component of the proton motive force (Piddock et al., Quinolone accumulation by *Pseudomonas aeruginosa, Staphylococcus aureus* and *Escherichia coli*. J Antimicrob Chemother 43, 61-70 (1999); and Diver et al., The accumulation of five quinolone antibacterial agents by *Escherichia coli*. J Antimicrob Chemother 25, 319-333 (1990)). Consistent with this, a potentiation of various FQs by bicarbonate was observed. The activity of FQs in the presence of bicarbonate against *E. coli* correlated with the nature of the substituents at the C-7 position of the quinolone nucleus (Table 8). The activities of FQs containing more basic substituents at C-7 (e.g., ciprofloxacin and besifloxacin) increased in the presence of bicarbonate, while those with more acidic substituents (e.g., nalidixic acid and pefloxacin) were suppressed (FIG. 6B, Table 8). These results indicate that the electrochemical component ($\Delta\psi$) of the proton motive force has a role in FQ uptake. Compensatory increases in $\Delta\psi$ associated with dissipation of $\Delta pH$ by bicarbonate would favor the uptake of positively charged species. In *S. aureus*, however, there was no enhancement by bicarbonate of FQs; instead, a small suppression was observed for the antibacterial activity of this chemical class.

TABLE 8

Structural formula and physicochemical properties of fluoroquinolones. Listed are the pKa values for the acidic and basic functions of the fluoroquinolones, generated from ChemAxon, a physico-chemical property predictor.

| Structure | | pKa (Strongest Acidic) | pKa (Strongest Basic) |
|---|---|---|---|
| Besifloxacin | *[chemical structure]* | 5.64 | 9.67 |
| Ciprofloxacin | *[chemical structure]* | 5.76 | 8.68 |

TABLE 8-continued

Structural formula and physicochemical properties of fluoroquinolones. Listed are the pKa values for the acidic and basic functions of the fluoroquinolones, generated from ChemAxon, a physico-chemical property predictor.

| Structure | | pKa (Strongest Acidic) | pKa (Strongest Basic) |
|---|---|---|---|
| Enoxacin | 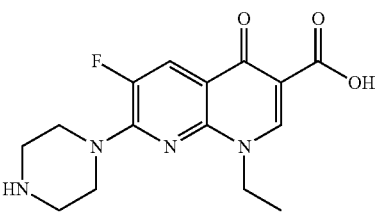 [SMILES: CCn1cc(C(=O)O)c(=O)c2cc(F)c(N3CCNCC3)nc21] | 5.5 | 8.59 |
| Levofloxacin | 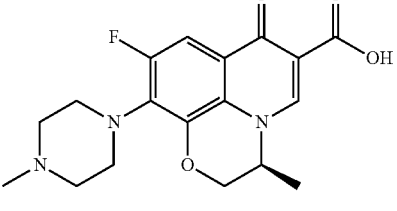 | 5.45 | 6.2 |
| Moxifloxacin | 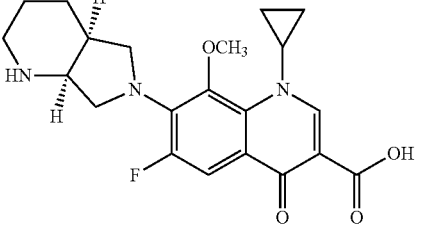 | 5.69 | 9.42 |
| Nalidixic acid | 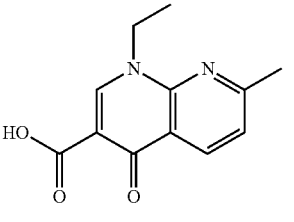 [SMILES: CCn1cc(C(=O)O)c(=O)c2ccc(C)nc21] | 5.95 | 4.68 |
| Norfloxacin | 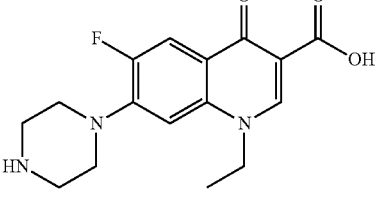 | 5.77 | 8.68 |
| Pefloxacin | 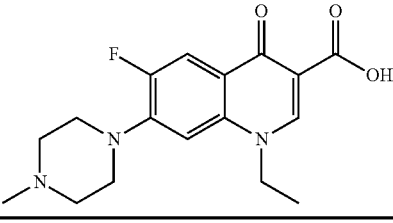 | 5.66 | 6.47 |

It is noted that antibiotic uptake is a complex function of permeability and efflux. The impact of bicarbonate on the pH gradient likely also impacts drug efflux, particularly in Gram-negative bacteria. Many multidrug efflux pumps depend on the PMF, where energy from the proton gradient is harnessed to expel drugs from the cell, such as the Resistance-Nodulation-Division (RND)-system AcrAB-TolC in *E. coli*. It was assessed whether consistent with a role in dissipating ΔpH, bicarbonate would reduce efflux activity. The potentiation of dirithromycin, for example, by bicarbonate was lost in a strain lacking the outer membrane channel of this tripartite efflux system (ΔtolC) (FIG. 11, Panel c), indicating it was inhibition of efflux by sodium bicarbonate that led to its enhanced activity. Although macrolide antibiotic agents are thought to be of little value for the treatment of Gram-negative bacteria due to their diminished accumulation these studies show that in the bicarbonate-rich environment of the host, energy-depended efflux systems may be less effective than predicted by conventional in vitro MIC determinations. Panel c shows that lack of the outer membrane tripartite pump, to/C, causes a loss of potentiation of sodium bicarbonate towards dirithromycin in *E. coli*. Shown are potency analyses of dirithromycin against: wild-type *E. coli* in MHB (1); wild-type *E. coli* in MHB supplemented with 25 mM sodium bicarbonate (2); ΔtolC in MHB (3); ΔtolC in MHB supplemented with 25 mM sodium bicarbonate (4). Averages of triplicate experiments are shown.

Figure 14:
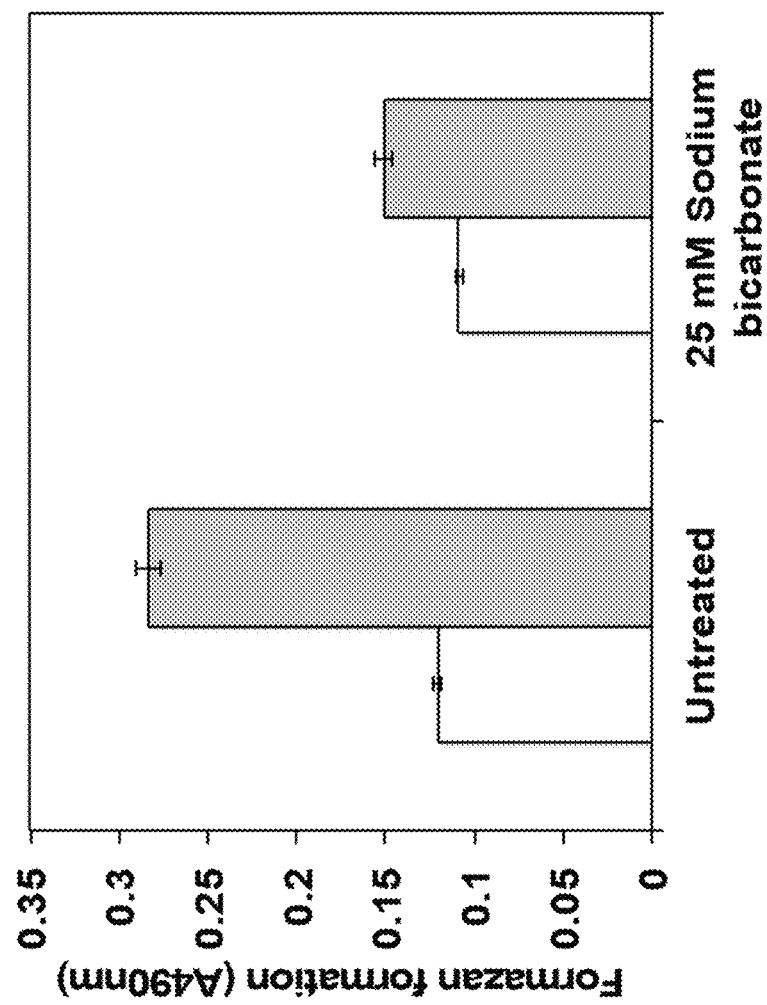
FIG. 14 is a bar graph showing that sodium bicarbonate inhibits cellular respiration in *E. coli*.

Inhibition of cell wall synthesis was attenuated in the presence of sodium bicarbonate in *E. coli* only 2-4 fold on average, but this suppression was more pronounced in *S. aureus*, which is generally more susceptible to cell wall synthesis inhibitors than Gram-negative bacteria. Where cell wall-active compounds are most effective on actively dividing bacteria, suppression of the action of the cidal antibiotic agents, β-lactams and cephalosporins, for example, may be due to reduced respiratory energy production to fuel growth in the presence of PMF-altering concentrations of bicarbonate (Lobritz, M. A. et al. Antibiotic efficacy is linked to bacterial cellular respiration. *Proc Natl Acad Sci USA* 112, 8173-8180, doi:10.1073/pnas.1509743112 (2015)). Accordingly, a significant effect on cellular respiration (70% reduction) in *E. coli* was observed, when treated with 25 mM sodium bicarbonate (FIG. 14). Specifically shown in FIG. 14 is the effect of 25 mM sodium bicarbonate on the reduction of 2-(p-iodophenyl)-3-(p-nitrophenyl)-5-phenyl tetrazolium chloride (INT) to INT-formazan. Open bars indicate the formation of formazan at t=0 as read at 490 nm. Grey bars represent the formation of formazan following 60 min incubation.

Figure 15:
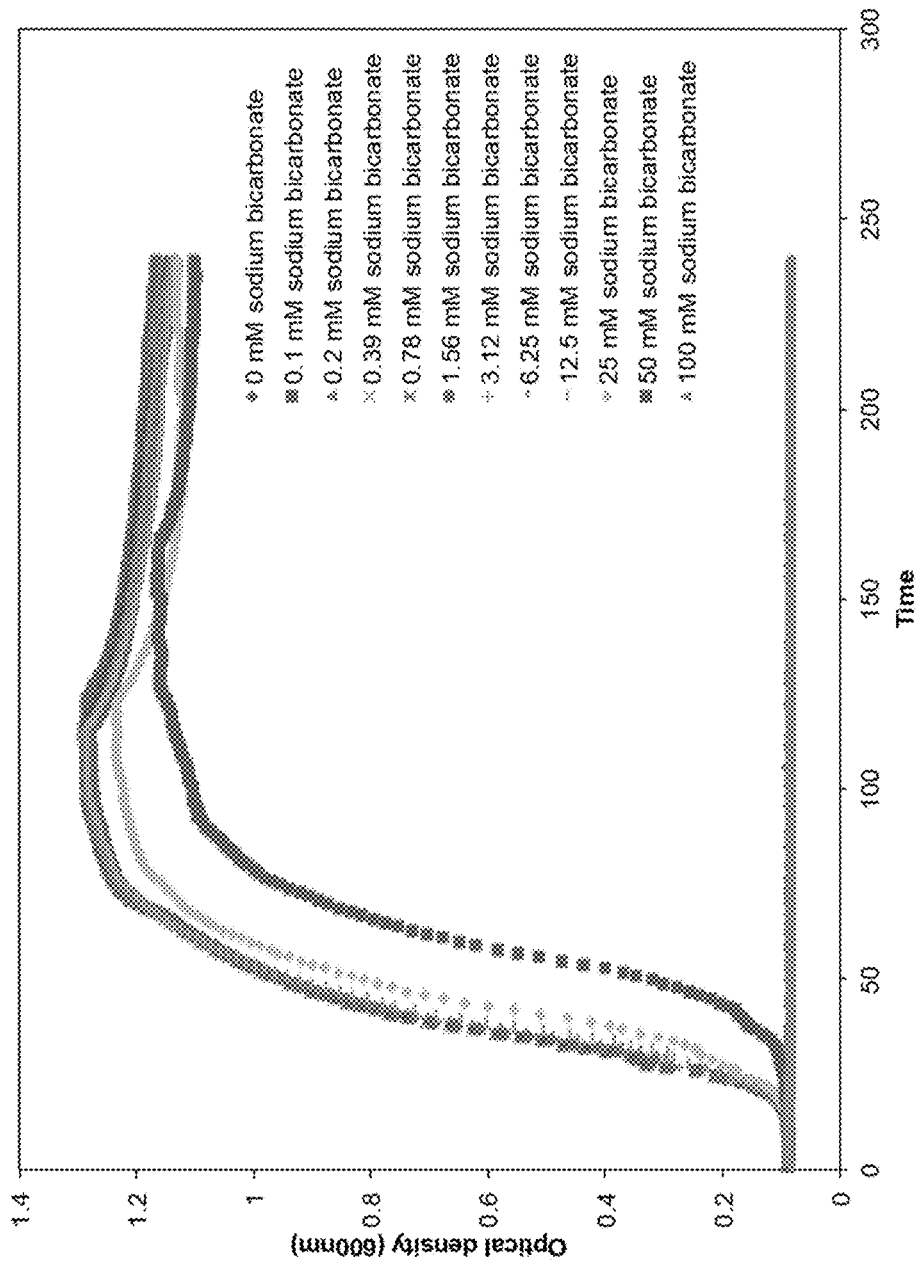
FIG. 15 is a line graph showing a growth curve of *E. coli* grown in the presence of varying concentrations of sodium bicarbonate.

Consistent with this finding, *E. coli* grown in high concentrations of sodium bicarbonate exhibited a delayed lag phase, indicating lowered metabolic resources (FIG. 15). FIG. 15 shows the growth curve of *E. coli* grown in the presence of varying concentrations of sodium bicarbonate. Growth curve measurements were performed in a microtiter plate and optical density read every 10 mins in a Tecan infinite M1000 Pro with shaking intervals before readings.

Figure 16:
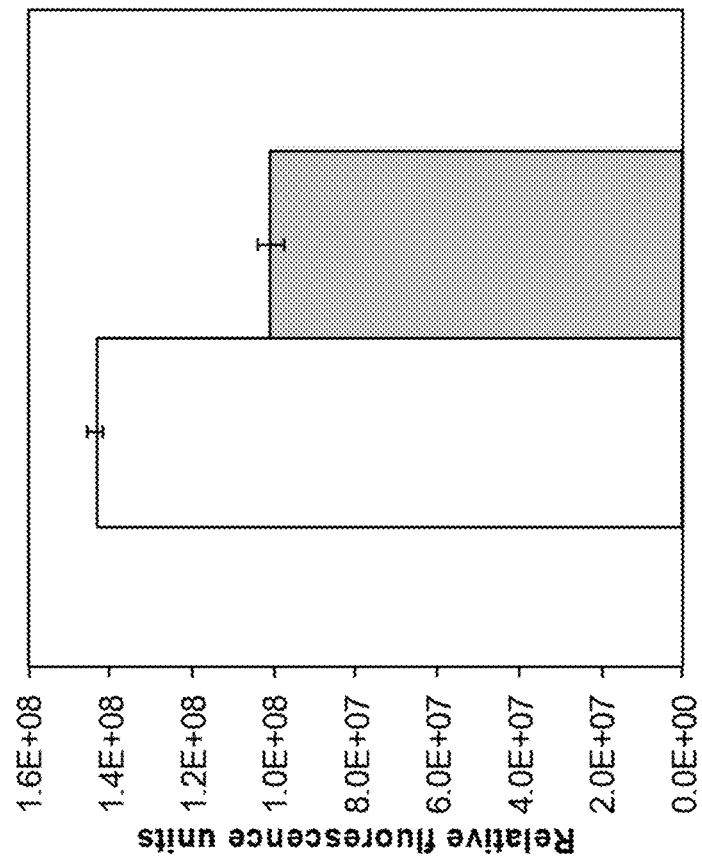
FIG. 16 is a bar graph showing the effect of 25 mM sodium bicarbonate on intracellular ATP levels in untreated

Further, intracellular ATP levels, which are produced via the $F_0F_1$-ATPase utilizing PMF, were reduced by ~30% in sodium bicarbonate-treated *E. coli* compared to the untreated control (FIG. 16). FIG. 16 shows the effect of 25 mM sodium bicarbonate on intracellular ATP levels, measured by a luciferin-luciferase bioluminescence assay. Shown is the relative fluorescence units for untreated *S. aureus* cells (white bar) and for 25 mM bicarbonate treated *S. aureus* cells (grey).

Overall, these experiments indicate that bicarbonate is a bacteriostatic compound that perturbs cellular respiration and reduces the activity of bactericidal antibiotic agents that require actively growing bacteria for activity.

Example 14: Effects of Gene Deletions in *E. coli* on the Ability of Bicarbonate to Reduce Growth The mode of action of bicarbonate on *E. coli* physiology was further investigated. The impact of 25 mM sodium bicarbonate on an ordered *E. coli* gene-deletion collection of ~4,000 strains was assessed. Sodium bicarbonate reduced the growth of 28 deletion strains. The missing genes encoded proteins involved in redox reactions and oxidative stress responses (FIG. 17A, Table 9). Among them was dsbB, whose gene product is required to maintain disulfide bonds in periplasmic enzymes at extreme pHs, and the gene encoding the sigma factor RpoS that regulates several components of resistance to both acid and base. Deletion in the gene cydX, coding for a cytochrome oxidase, caused sensitization to bicarbonate. Deletion in the gene nhaA, which encodes a $Na^+:NH^+$ antiporter that has a major role in sodium ion and alkaline pH homeostasis in *E. coli* and many enterobacteria, sensitized cells to bicarbonate. It was observed that a defect in proton expulsion enhanced the growth inhibition by bicarbonate. Deletion of cya was also sensitized to bicarbonate. Overall, it was observed that gene deletions sensitized to bicarbonate involved pH-related processes, through proton expulsion or stress responses, that when deleted amplify bicarbonate's action on the pH gradient across the inner membrane.

FIG. 17A: Keio collection was exposed to 25 mM bicarbonate for 15 hours at 37° C., and sick/lethal interactions were assessed using a multiplicative approach (French et al., A robust platform for chemical genomics in bacterial systems. *Mol Biol Cell* 27, 1015-1025, doi:10.1091/mbc.E15-08-0573 (2016)). Shown alongside an index plot of the chemical-genetic interactions are the 15 mutations that most strongly enhanced the activity of bicarbonate (displayed as 1-interaction score).

TABLE 9

Genetic enhancers (Keio collection) of growth inhibition by 25 mM bicarbonate. Strains were exposed to bicarbonate for 15 hours in cation-adjusted MHB broth, and a multiplicative approach was used to determine the sick or lethal effects on each strain. Shown here are the outliers from FIG. 17A, alongside their gene products, as annotated from EcoCyc.

| Deletion strain | Gene description |
|---|---|
| appX | small outer membrane protein |
| cyaA | adenylate cyclase |
| cydX | cytochrome bd I terminal oxidase - CydX subunit |
| degP | serine protease Do |
| dnaT | primosomal protein DnaT |
| dsbB | protein disulfide oxidoreductase |
| envC | EnvC divisome associated factor, activator of peptidoglycan hydrolases |
| fur | Fur transcriptional dual regulator |
| galE | UDP-glucose 4-epimerase |
| glnA | adenylyl-[glutamine synthetase], glutamine synthetase |
| hfq | RNA-binding protein that affects many cellular processes; homolog of mammalian Sm/Sm-like proteins |
| lpoB | outer membrane lipoprotein - activator of MrcB activity |
| mgrB | negative feedback regulator of the PhoQP system |
| nhaA | $Na^+:H^+$ antiporter NhaA |
| pgi | phosphoglucose isomerase |
| recB | RecB |
| rodZ | transmembrane component of cytoskeleton |
| rplA | 50S ribosomal subunit protein L1 |
| rpmF | 50S ribosomal subunit protein L32 |
| rpoS | RNA polymerase, sigma S (sigma 38) factor |
| rpsT | 30S ribosomal subunit protein S20 |
| rsgA | ribosome small subunit-dependent GTPase A |
| sapA | periplasmic binding protein SapA of predicted ABC transporter |
| treA | periplasmic trehalase |
| ubiF | 2-octaprenyl-3-methyl-6-methoxy-1,4-benzoquinone hydroxylase |
| ubiH | 2-octaprenyl-6-methoxyphenol hydroxylase |

TABLE 9-continued

Genetic enhancers (Keio collection) of growth inhibition by 25 mM bicarbonate. Strains were exposed to bicarbonate for 15 hours in cation-adjusted MHB broth, and a multiplicative approach was used to determine the sick or lethal effects on each strain. Shown here are the outliers from FIG. 17A, alongside their gene products, as annotated from EcoCyc.

| Deletion strain | Gene description |
|---|---|
| ybbY | putative transport protein, nucleobase:cation symporter-2 (NCS2) family |
| ybcO | DLP12 prophage; predicted protein |
| yciB | inner membrane protein |

Example 15: Adaptive Strategies by *E. coli* in Response to Sodium Bicarbonate The action of sodium bicarbonate on *E. coli* was further assessed by analyzing promoter activity in response to 25 mM sodium bicarbonate using a genome-scale, promoter-reporter library where nearly all of the promoters in *E. coli* have been transcriptionally fused to gfp (FIG. 17B, Table 10).

Shown in FIG. 17B are the responses of a genome-scale GFP promoter library (Zaslaver et al., A comprehensive library of fluorescent transcriptional reporters for *Escherichia coli*. Nat Methods 3, 623-628, doi:10.1038/nmeth895 (2006)), to 25 mM bicarbonate. Highlighted are promoters with increased and decreased expression. Of note are the genes nhaA and hfq, that were strong enhancers of growth inhibition by bicarbonate and were differentially expressed in bicarbonate containing medium.

TABLE 10

List of promoters from the GFP promoter-fusion library that demonstrated increased or decreased promoter activity in the presence of 25 mM bicarbonate. Activity was assessed using the pipeline of Zaslaver et al. Shown here are the promoters from FIG. 17B, alongside their gene products, as annotated from EcoCyc.

| Increased promoter activity | |
|---|---|
| Name | Product |
| ais | Predicted lipopolysaccharide core heptose(II)-phosphate phosphatase |
| alsB | D-allose ABC transporter - periplasmic binding protein |
| asd | Aspartate semialdehyde dehydrogenase |
| cspI | Qin prophage; cold shock protein |
| dinG | ATP-dependent helicase |
| dmlA | D-malate/3-isopropylmalate dehydrogenase (decarboxylating) |
| dusA | tRNA-dihydrouridine synthase A |
| dusB | tRNA-dihydrouridine synthase B |
| entD | Phosphopantetheinyl transferase |
| erpA | Essential respiratory protein A |
| fetA | ABC transporter with a role in iron homeostasis - ATP-binding subunit |
| glyU | tRNA-glyU |
| htrL | Involved in lipopolysaccharide biosynthesis |
| iscR | IscR DNA-binding transcriptional dual regulator |
| kefF | Regulator of KefC-mediated potassium transport and quinone oxidoreductase |
| lpxC | UDP-3-O-acyl-N-acetylglucosamine deacetylase |
| mltC | Membrane-bound lytic murein transglycosylase C |
| murJ | Lipid II flippase |
| mutY | Adenine glycosylase; G.C --> T.A transversions |
| nhaA | Na+:H+ antiporter NhaA |
| potF | Putrescine ABC transporter - periplasmic binding protein |
| rcsC | RcsC sensory histidine kinase - asp875 phosphorylated |
| rfaH | RfaH transcriptional antiterminator |
| rplN | 50S ribosomal subunit protein L14 |
| rplY | 50S ribosomal subunit protein L25 |
| rpsJ | 30S ribosomal subunit protein S10 |
| rpsM | 30S ribosomal subunit protein S13 |
| rpsO | 30S ribosomal subunit protein S15 |
| rpsP | 30S ribosomal subunit protein S16 |
| rsfS | Ribosomal silencing factor |
| smpB | Small protein B |
| sppA | Protease IV, a signal peptide peptidase |
| tig | Chaperone protein Tig; trigger factor |
| trxA | Oxidized thioredoxin, thioredoxin 1 |
| ttcA | tRNA C32 thiolase |
| waaZ | Protein involved in KdoIII attachment during lipopolysaccharide core biosynthesis |
| yacG | DNA gyrase inhibitor YacG |
| ybaA | Conserved protein |
| ybaB | Conserved DNA-binding protein |
| ybfE | LexA-regulated protein |
| ycgM | Predicted isomerase/hydrolase |
| ydeA | Arabinose exporter |
| yeiE | LYSR-type transcriptional regulator |
| yejL | Conserved protein |
| yidH | Conserved inner membrane protein |
| yjdI | Conserved protein |
| yncE | Conserved protein |

TABLE 10-continued

List of promoters from the GFP promoter-fusion library that demonstrated increased or decreased promoter activity in the presence of 25 mM bicarbonate. Activity was assessed using the pipeline of Zaslaver et al. Shown here are the promoters from FIG. 17B, alongside their gene products, as annotated from EcoCyc.

| | |
|---|---|
| yphG | Conserved protein |
| zraP | Zinc responsive, periplasmic protein with chaperone activity |

Decreased promoter activity

| Name | Product |
|---|---|
| aspU | tRNA-aspU |
| bioB | Biotin synthase |
| deaD | DeaD, DEAD-box RNA helicase |
| fadE | Acyl-CoA dehydrogenase |
| folD | Bifunctional 5,10-methylene-tetrahydrofolate dehydrogenase/5,10-methylene-tetrahydrofolate cyclohydrolase |
| fpr | Flavodoxin-NADP + reductase/ferredoxin-NADP + reductase |
| ftp | Flavin transferase |
| ftsZ | Essential cell division protein FtsZ |
| gcvA | GcvA DNA-binding transcriptional dual regulator |
| glnA | Adenylyl-[glutamine synthetase], glutamine synthetase |
| glrK | GlrK sensory histidine kinase - phosphorylated, GlrK sensory histidine kinase |
| hemA | Glutamyl-tRNA reductase |
| hfq | RNA-binding protein that affects many cellular processes; homolog of mammalian Sm/Sm-like proteins |
| hofM | Protein involved in utilization of DNA as a carbon source |
| hscC | Hsc62, Hsp70 family chaperone, binds to RpoD and inhibits transcription |
| lysO | L-lysine exporter |
| metZ | TRNA-fMet1 |
| pepQ | Xaa-Pro dipeptidase |
| polB | DNA polymerase II |
| prlF | PrlF antitoxin |
| radD | Predicted ATP-dependent helicase; implicated in DNA repair |
| rapA | RNA polymerase-binding ATPase and RNAP recycling factor |
| rhaD | Rhamnulose-1-phosphate aldolase |
| rpmI | 50S ribosomal subunit protein L35 |
| rrfG | rrfG 5S ribosomal RNA |
| rrlH | rrlH 23S ribosomal RNA |
| sbcB | Exonuclease I, 3' --> 5' specific; deoxyribophosphodiesterase |
| tcdA | tRNA threonylcarbamoyladenosine dehydratase |
| yahK | Aldehyde reductase, NADPH-dependent |
| ybiO | Mechanosensitive channel YbiO |
| ydbC | Predicted oxidoreductase, NAD(P)-binding |
| yegW | Predicted DNA-binding transcriptional regulator |
| ygbI | Predicted DNA-binding transcriptional regulator, DEOR-type |
| yiaT | Outer membrane protein YiaT |
| yieH | 6-Phosphogluconate phosphatase |
| yjbF | Predicted lipoprotein |
| YifY | Putative protein |
| ykgF | Predicted amino acid dehydrogenase with NAD(P)-binding domain and ferridoxin-like domain |
| ykgJ | Predicted ferredoxin |
| ynfC | YnfC lipoprotein |
| yodB | Predicted cytochrome |
| ypdA | YbdA sensory histidine kinase - his371 phosphorylated |

Changes in promoter activity that reflected adaptive strategies by the bacterium to maintain pH homeostasis were observed. Promoter activity for a large number of substrate/proton antiporters was repressed in the presence of bicarbonate. Promoter activity for nhaA was enhanced in the presence of bicarbonate.

Upon treatment with bicarbonate, cytoplasmic pH, which began at ~7.5, endured a rapid cytoplasmic alkalinization, as measured by BCECF-AM (FIG. 20). FIG. 20 shows changes in intracellular pH upon treatment with bicarbonate. S. aureus cells were loaded with the pH sensitive dye BCECF-AM and were washed and resuspended in PBS. Following baseline readings, PBS (grey circles) or 25 mM sodium bicarbonate (black circles) were added at the arrow and fluorescence measured over time. A standard curve for intracellular pH calibration was used to calculate intracellular pH.

The expression of a number of inner membrane protein/transporters was differentially regulated in the presence of bicarbonate. Decreased promoter activity was also observed for many ATP-dependent processes, likely as an adaptive effort to conserve energy.

These data indicate that overall, E. coli adaptation to bicarbonate involved strategies to respond to periplasmic pH changes, increase membrane potential and preserve energy.

Example 16: The Effect of Bicarbonate on the Activity of Molecules that Selectively Perturb $\Delta\psi$ It was assessed whether bicarbonate enhances the activity of molecules that selectively perturb $\Delta\psi$. To test this, the following $\Delta\psi$ dissipaters were combined with sodium bicarbonate: valinomycin, a selective potassium ionophore, as well as compounds that have previously characterized as dissipaters of Δψ, namely I1, I2 and I3 (Farha, M. A., Verschoor, C. P., Bowdish, D. & Brown, E. D. Collapsing the proton motive force to identify synergistic combinations against *Staphylococcus aureus*. Chemistry & biology 20, 1168-1178, doi:10.1016/j.chembiol.2013.07.006 (2013)) and loperamide (Ejim, L. et al. Combinations of antibiotics and nonantibiotic drugs enhance antimicrobial efficacy. *Nature chemical biology* 7, 348-350, doi:10.1038/nchembio.559 (2011).

All combinations yielded synergistic interactions, consistent with the role of bicarbonate as a selective dissipater of ΔpH (FIGS. 18A-18E). FIGS. 18A-18E show a microdilution checkerboard analyses for sodium bicarbonate and molecules shown to dissipate ΔΨ; FIG. 18A) valinomycin in *S. aureus*; FIG. 18B) loperamide in *E. coli*; and FIGS. 18C-18E) molecules I1 (FIG. 18C), I2 (FIG. 18D) and I3 (FIG. 18E) in *S. aureus*. All checkerboards display synergistic interactions.

This indicates that membrane active agents that target Δψ, while frequently eschewed in drug discovery efforts for potential cytotoxicity, can have superior activity in the bicarbonate-rich environment of the host.

Example 17: The Effect of Bicarbonate is not an Effect of Changes in pH

PMF is driven in part by a transmembrane gradient where the periplasmic side of the membrane has a greater concentration of protons. Thus, the addition of buffering agents to alter the external pH can have a significant effect on PMF. To assess the impact of such a perturbation, trisodium phosphate ($Na_3PO_4$) was added, which increased the pH of the media by 3 units and also potentiated the activity of dirithromycin. Adjusting the pH back to neutrality, however, led to a loss of synergy (FIGS. 19A-19B). FIGS. 19A-19B show the effect of pH-adjusting media on the combination of dirithromycin with trisodium phosphate. Shown are microdilution checkerboard analyses for dirithromycin and trisodium phosphate when FIG. 19A) pH is not adjusted to 7.2 (pH~10) and when FIG. 19B) pH of the medium is adjusted to 7.2. Conversely, supplementation with sodium bicarbonate has little impact on the pH. Steps were taken throughout the studies to confirm that bicarbonate supplemented media were at pH 7.4, and adjusted where necessary. The bicarbonate effect is not a trivial consequence of the pH of the media. Supplementation of the media with a variety of buffer systems indicated that potentiation was unique to bicarbonate.

Consistent with the idea that bicarbonate is acting extracytoplasmically, presumably in the periplasmic space, no difference in bicarbonate's ability to potentiate dirithromycin in a bicarbonate transporter-deficient strain (ΔychM) and in a wild-type strain was observed (FIGS. 21A-21B). FIGS. 21A-21B show the growth inhibition by dirithromycin and sodium bicarbonate. Bacterial strains were wild type *E. coli* in FIG. 21A; and *E. coli* ΔychM in FIG. 21B.

Example 18: The Effect of Bicarbonate on the Activity of Pentamidine

The enhanced antibacterial activity of pentamidine depended on the presence of an ionic milieu that is comparable to the conditions found in mammalian tissues and specifically on the presence of bicarbonate. Indeed, the antibacterial activity of pentamidine was potentiated with increasing concentrations of sodium bicarbonate. Pentamidine activity was found to be antagonized in the presence of NaCl, which is present in high concentrations in standard microbiological media. In the presence of bicarbonate, however, the antibacterial activity of pentamidine was potentiated on average 40-fold against Gram-negative organisms and 50-fold against Gram-positive organisms.

Consistently, an unforeseeable efficacy for pentamidine in clearing an *A. baumannii* systemic infection in mice was observed for the first time. The consequence of secondary factors affecting pentamidine's antibacterial activity is consistent with the significant in vivo activity observed.

In addition to diamidines, like pentamidine, many conventional antibiotic agents also displayed an interaction with bicarbonate. Remarkably, varying classes of conventional antibiotic agents displayed significant potentiation (macrolides, and some fluoroquinolones) in the presence of physiological concentrations of bicarbonate (25 mM). Significantly, not all conventional antibiotic agents displayed a synergistic interaction with bicarbonate as some antibiotic agents resulted in significant suppression of activity (e.g. tetracyclines, some fluoroquinolones, cell wall active antibiotic agents, amino-coumarins) in the presence of physiological concentrations of bicarbonate (25 mM).

The investigations into the mode of action of bicarbonate revealed an ability to dissipate the pH gradient of the proton motive force across the cytoplasmic membrane. In doing so, bicarbonate suppresses the entry of antibiotic agents that are driven by the pH gradient and enhances the entry of antibiotic agents that are driven by the opposing and compensatory component, the membrane potential. Further, by disrupting the energetics across the membrane, bicarbonate also disrupts energy-dependent efflux systems thus further enhancing the accumulation of antibiotic agents that are actively effluxed. In the case of pentamidine, the latter disrupts the membrane potential across the membrane, thus when used with bicarbonate, both components that make up the proton motive force are synergistically targeted. This phenomenon was also observed with other various small molecules that dissipate membrane potential when used with bicarbonate.

Like bacterial cells, yeast and fungal cells have a cytoplasm and a membrane surrounded by a cell wall. Within the plasma membrane is a chemiosmotic mechanism that is very similar to that of bacteria. In fact, these energetics mechanisms underlie the function of nearly all living organisms. Indeed, energetics via components of proton motive force in yeast and fungi is very similar to that of bacteria and runs at similar values (−150 to −200 mV).

Many classes of conventional antibiotic agents displayed significant potentiation or suppression in the presence of physiological concentrations of bicarbonate. All interactions pointed to a mechanism whereby the bicarbonate ion causes perturbation of the pH gradient of proton motive force (PMF) across the cytoplasmic membrane. The product of cellular respiration, PMF, describes the electrochemical potential at the cytoplasmic membrane that is composed of an electrical potential (Δψ, negative inside) and a proton gradient (ΔpH, acidic outside). This electrochemical potential crucially underpins energy production so that bacterial cells work to maintain a constant PMF (Bakker, E. P. & Mangerich, W. E. J Bacteriol 1981, 147: 820-826). Agents that perturb either Δψ or ΔpH are growth inhibitory and prompt a compensatory increase in the other component in order to maintain PMF. Further, synergy in growth inhibition is observed when an agent active on the electrical potential is combined with an agent that targets the proton gradient (Farha et al, Chemistry and Biology 2013, 20:1168-78).

Thus, in dissipating the pH gradient, bicarbonate had enhancing effects on other antibacterial compounds through distinct mechanisms: (a) Bicarbonate dissipated the pH gradient across the cytoplasmic membrane and led to an increase in the compensatory component, the membrane potential. For antibiotic agents whose entries are dependent on the membrane potential, an enhancement of growth inhibition was observed in the presence of sodium bicarbonate, consistent with an increase in antibiotic entry. Further, by disrupting the energetics across the membrane, bicarbonate also disrupts energy-dependent efflux thus potentiating the activity of efflux substrates (e.g. macrolides). In these instances, it was observed that bicarbonate led to an increase in intracellular concentration of the antibiotic. (b) In an alternate mechanism, bicarbonate enhanced those compounds that disrupt membrane potential component as a primary mechanism of action. These activities were potentiated via a synergistic collapse of both components of PMF, $\Delta\psi$ by the antibiotic and $\Delta$pH by bicarbonate. In all, by altering the cell's transmembrane pH gradient, bicarbonate potentiates antibiotic activity by increasing the effective intracellular levels of various antibiotic agents or enhancing their ability to collapse PMF, including pentamidine, an overlooked antibacterial thought to lack in vivo antibacterial activity. Furthermore, it was observed that bicarbonate works together with components of innate immunity (innate immunity factors) to inhibit the growth of bacterial pathogens. In sum, these data implicate bicarbonate as an overlooked potentiator of host immunity in the defense against pathogens. This study suggests that bicarbonate is an overlooked immune factor that may lead to unrecognized in vivo activities of clinically useful antibiotic agents and a potential natural and innocuous additive in the design of novel therapeutic strategies.

Example 19: The Effect of Bicarbonate on the Activity of Antibiotic Agents

The effect of sodium bicarbonate on the activity of various antibacterial agents was investigated. Clinical isolates of various bacteria were obtained from the American Type Culture Collection ("ATCC") and the International Health Management Associates ("IHMA"). Fractional inhibitory concentration indices (FICIs) were determined by setting up standard checkerboard broth microdilution assays in 96-well microtiter plates with serially diluted 8 (or 10) concentrations of each drug (sodium bicarbonate and the antibacterial agent). The protocol for checkerboard analyses was based on the CLSI guidelines. Plates were incubated at 37° C. for 18 hours, and optical density was read at 600 nm. At least 3 replicates were done for each query compound. Graphical results of these assays are shown in FIGS. 22-25.

The MIC for each drug was the lowest drug concentration showing <10% growth. The FIC for each drug was calculated as the concentration of drug in the presence of the co-drug for a well showing <10% growth, divided by the MIC for that drug, as shown in the equation below. The FIC index (FICI) is the sum of the two FICs. Chemical-chemical interactions with $\Sigma$FIC of less or equal to 0.5 were deemed synergistic.

Fractional Inhibitory Concentration (FIC)=[Y]/MIC$_X$, where [Y] is the lowest inhibitory concentration of drug in the presence of the bicarbonate.

Example 20: The Effect of Bicarbonate on the Activity of Antibiotic Agents

The effect of sodium bicarbonate on the activity of additional antibacterial agents was investigated. Clinical isolates of various bacteria were obtained from the ATCC and the IHMA. The MIC of the antibiotic agents were determined in Mueller-Hinton broth (MHB) media and compared to the MIC in MEM supplemented with physiological concentrations of sodium bicarbonate (25 mM). The results are shown in FIG. 26 and Table 11. Shown are the fold shifts in *E. coli* (black) and fold shifts in *S. aureus* (gray).

TABLE 11

MIC (µg of antimicrobial agent/mL of buffer) of antibiotic agents against *E. coli* and *S. aureus* in MHB in the absence of sodium bicarbonate ("MHB−") versus MHB in the presence of 25 mM sodium bicarbonate ("MHB+").

|  | *E. coli* | | | *S. aureus* | | |
| --- | --- | --- | --- | --- | --- | --- |
|  | MHB− | MHB+ | Fold | MHB− | MHB+ | Fold |
| Amikacin | 4 | 4 | 1 | 4 | 8 | −2 |
| Benzamide | >128 | >128 | 1 | >128 | >128 | 1 |
| Cefaclor | 4 | 4 | 1 | 2 | 8 | −4 |
| Cefotaxime | 4 | 8 | −2 | 0.5 | 2 | −4 |
| Clarithromycin | 64 | 8 | 8 | 0.5 | 0.062 | 8 |
| Clindamycin | 128 | 128 | 1 | 0.25 | 0.12 | 2 |
| Colistin | 0.5 | 0.5 | 1 | >128 | >128 | 1 |
| Daptomycin | >16 | >16 | 1 | 2 | 1 | 2 |
| Furadinozoline | 4 | 4 | 1 | 32 | 16 | 2 |
| Fusidic acid | >128 | >128 | 1 | 0.5 | 2 | −4 |
| Gatifloxacin | 16 | 4 | 4 | 4 | 8 | −2 |
| Gramicidin | >128 | >128 | 1 | 1 | 0.25 | 4 |
| Hygromycin B | 32 | 16 | 2 | >128 | 64 | 2 |
| Lincomycin | >128 | 32 | 4 | 0.25 | 0.0625 | 4 |
| Lomefloxacin | 0.5 | 0.125 | 4 | 4 | 8 | −2 |
| Metronidazole | >128 | >128 | 1 | >128 | >128 | 1 |
| Mupirocin | 128 | 128 | 1 | 0.5 | 2 | −4 |
| Nadifloxacin | 8 | 32 | −4 | 0.12 | 0.5 | −4 |
| Nafcillin | 16 | 32 | −2 | 0.25 | 1 | −4 |
| Nisin | >128 | >128 | 1 | >128 | >128 | 1 |
| Pleuromutilin | >128 | >128 | 1 | 1 | 1 | 1 |
| Roxithromycin | >128 | 16 | 8 | 4 | 0.5 | 16 |
| Sparfloxacin | 16 | 32 | 2 | 0.125 | 0.25 | −2 |
| Spiramycin | >128 | 64 | 8 | 16 | 0.5 | 16 |
| Streptomycin | 0.5 | 0.12 | 4 | 2 | 0.5 | 4 |
| Teicoplanin | 128 | 128 | 1 | 1 | 2 | −2 |
| Telithromycin | >128 | 16 | 8 | 4 | 0.5 | 8 |
| Thiostrepton | >128 | >128 | 1 | 0.5 | 0.12 | 4 |
| Ticarcillin | 32 | 64 | −2 | 8 | 32 | −4 |
| Tobramycin | 0.25 | 0.25 | 1 | 0.25 | 0.5 | −2 |
| Triclosan | 0.125 | 0.125 | 1 | 0.062 | 0.062 | 1 |

As validation, three of the antibiotic agents were further tested with checkerboard analyses. Checkerboard broth microdilution assays were set up in 96-well microtiter plates with serially diluted 8 (or 10) concentrations of each compound (sodium bicarbonate and the antibiotic). The protocol for checkerboard analyses was based on the CLSI guidelines. Plates were incubated at 37° C. for 18 hours, and optical density was read at 600 nm. At least 3 replicates were done for each query compound. FIG. 27 shows the results of these assays for the activity of spiramycin, roxithromycin and streptomycin against *E. coli* and *S. aureus*. The antibacterial activity of spiramycin, roxithromycin and streptomycin was enhanced by bicarbonate, showing synergistic interactions.

Example 21: The Effect of Bicarbonate on the Antibacterial Activity of Therapeutic Agents The effect of physiological concentrations of bicarbonate on the antibacterial activity of therapeutic agents previously approved by the United States Food and Drug Administration was investigated. A high-throughput screen of the Pharmakon library, a collection of 1,600 previously approved pharmaceutical agents, was conducted. The MIC of the agents against *E. coli* were determined in MHB media and compared to the MIC in MHB supplemented with physiological concentrations of sodium bicarbonate (25 mM). A hit cut-off was determined by calculating the mean and standard deviation of the full dataset. A statistical cutoff equal to the mean+2 standard deviations was established. Table 12 lists the agents having antibacterial activity that was enhanced in the presence of sodium bicarbonate. A variety of agents registered as hits, including known antibiotic agents found in the library.

TABLE 12

Pharmaceutical agents with antibacterial activity that was enhanced in the presence of sodium bicarbonate.

BROMOCRIPTINE MESYLATE
AMINACRINE
ZIDOVUDINE
ACRISORCIN
CHLORHEXIDINE HYDROCHLORIDE
CETYLPYRIDINIUM CHLORIDE
MITOXANTRONE HYDROCHLORIDE
AMSACRINE
HOMIDIUM BROMIDE
SPECTINOMYCIN HYDROCHLORIDE
SULFAMETHAZINE
BENZALKONIUM CHLORIDE
DIRITHROMYCIN
ERYTHROMYCIN ETHYLSUCCINATE
ROXITHROMYCIN
CLARITHROMYCIN
SULFAPHENAZOLE
ERYTHROMYCIN
SULFADIMETHOXINE
CHLOROXINE
ERYTHROMYCIN STEARATE
ACRIFLAVINIUM HYDROCHLORIDE
PENTAMIDINE ISETHIONATE
CEFDITORIN PIVOXIL
DIMINAZENE ACETURATE
SULFAPYRIDINE
ROPINIROLE HYDROCHLORIDE
SULFAGUANIDINE
METERGOLINE
CLOSANTEL
SULFAMETER
CEFALONIUM
SULFADOXINE
DOXORUBICIN
CETRIMONIUM BROMIDE
PHENYLMERCURIC ACETATE
DEQUALINIUM CHLORIDE
CLIOQUINOL
AMIODARONE HYDROCHLORIDE
MONOBENZONE
PROFLAVINE HEMISULFATE
NISOLDIPINE
METHYLBENZETHONIUM CHLORIDE
CEPHALOTHIN SODIUM
FLUVOXAMINE MALEATE
ITRACONAZOLE
TACRINE HYDROCHLORIDE
GUANABENZ ACETATE
RAMOPLANIN
ORLISTAT
CLOFOCTOL
PUROMYCIN HYDROCHLORIDE
BENZETHONIUM CHLORIDE
TELITHROMYCIN
BROXALDINE
SANGUINARINE SULFATE
DIHYDROSTREPTOMYCIN SULFATE
OCTISALATE
ETHACRIDINE LACTATE
STAVUDINE
MUPIROCIN

TABLE 12-continued

Pharmaceutical agents with antibacterial activity that was enhanced in the presence of sodium bicarbonate.

BITHIONATE SODIUM
VORICONAZOLE
MONTELUKAST SODIUM
OLTIPRAZ
IPRATROPIUM BROMIDE
IPRIFLAVONE
ENALAPRIL MALEATE
FLOPROPIONE
SULFAQUINOXALINE SODIUM
SPIRAMYCIN
BISOCTRIZOLE
AZATHIOPRINE
ENALAPRILAT
EXALAMIDE

As validation for the screen, nine of the therapeutic agents from Table 12 were tested via checkerboard analyses in the presence of sodium bicarbonate. Checkerboard broth microdilution assays were set up in 96-well microtiter plates with serially diluted 8 (or 10) concentrations of each compound (sodium bicarbonate and pharmaceutical agent). The protocol for checkerboard analyses was based on the CLSI guidelines. Plates were incubated at 37° C. for 18 hours, and optical density was read at 600 nm. At least 3 replicates were done for each query compound. FIG. 28 shows the results of these assays against *E. coli*. In all cases, synergistic interactions between the therapeutic agents and bicarbonate were observed.

Example 22: The Effect of Bicarbonate on the Activity of Antiseptic Agents

The effect of sodium bicarbonate on the activity of cationic antiseptic agents was investigated. Clinical isolates of various bacteria were obtained from the ATCC and the IHMA. The MIC of the antiseptic agents was determined in MHB media and compared to the MIC in MHB supplemented with physiological concentrations of sodium bicarbonate (25 mM). The results are shown in FIG. 29 and Table 13. Shown are the fold shifts in *E. coli* (black) and fold shifts in *S. aureus* (gray).

TABLE 13

MIC (µg of antimicrobial agent/mL of buffer) of antiseptic agents against *E. coli* and *S. aureus* in MHB in the absence of sodium bicarbonate ("MHB−") versus MHB in the presence of 25 mM sodium bicarbonate ("MHB+").

| | *E. coli* | | | *S. aureus* | | |
|---|---|---|---|---|---|---|
| | MHB | MHB+ | Fold | MHB | MHB+ | Fold |
| Benzalkonium chloride | 32 | 8 | 4 | 0.5 | 0.25 | 2 |
| Benzethonium chloride | 64 | 32 | 2 | 1 | 0.5 | 2 |
| Cetrimodium bromide | >128 | 32 | 4 | 16 | 4 | 4 |
| Cetylpyridinium chloride | 16 | 4 | 4 | 0.125 | 0.0156 | 8 |
| Chlorhexidine | 0.5 | 0.125 | 2 | 0.5 | 0.0625 | 4 |
| Dibrompropamidine diisetionate | 64 | 16 | 4 | 4 | 1 | 4 |
| Hexadecyltrimethyl-ammonium bromide | 32 | 8 | 4 | 0.5 | 0.25 | 2 |
| p-hydroxybenzoate | 64 | 64 | 1 | 16 | 16 | 1 |
| Polyhexanide | 1 | 0.5 | 2 | 0.5 | 0.25 | 2 |
| Polyvinylpyrrolidone iodine complex | >128 | >128 | 1 | >128 | >128 | 1 |

As validation, one of the antiseptic agents (cetylpyridinium chloride) was further tested with checkerboard analyses. Checkerboard broth microdilution assays were set up in 96-well microtiter plates with serially diluted 8 (or 10) concentrations of each drug (sodium bicarbonate and antiseptic agent). The protocol for checkerboard analyses was based on the CLSI guidelines. Plates were incubated at 37° C. for 18 hours, and optical density was read at 600 nm. At least 3 replicates were done for the query compound. FIG. 30 shows the results of these assays for the activity of cetylpyridinium chloride against *E. coli* and *S. aureus*. The antibacterial activity of cetylpyridinium chloride was enhanced by bicarbonate, showing synergistic interactions.

Example 23: The Effect of Bicarbonate on the Activity of Antimicrobial Agents in Animal Models of Infection The effectiveness of an antimicrobial agent in the absence or in the presence of sodium bicarbonate is tested in animal models of infection.

Skin infection: BALB/c mice are pretreated with 150 mg/kg (Day −4) and 100 mg/kg (Day −1) of cyclophosphamide to render mice neutropenic. Mice are anesthetized using isofluorane and administered the analgesic buprenorphine (0.1 mg/kg) intraperitoneally. A section of the mouse's back is tape-stripped to create a wound using approximately 20 pieces of autoclave tape. Mice are infected with approximately $1 \times 10^6$ CFU of *S. aureus* (MRSA) directly pipetted on the wounded skin. Infections are allowed to establish for two hours prior to treatment with (1) sodium bicarbonate (2) an antimicrobial agent or (3) both sodium bicarbonate and the antimicrobial agent. The sodium bicarbonate may be administered at 50-200 mM. The antimicrobial agent can be a polymyxin, azithromycin, or diminazene. The antimicrobial agent can be polymyxin B (1-2 mg/mL). The treatment is pipetted (50 µL volume) directly on the wound and is administered 8-12 times over the next 24 hours. Mice are euthanized, and the wound tissue collected 24 hours after infection. Colony forming units per mL (CFU/mL) of bacteria from the wound tissue is measured for each treatment.

Lung infection: Female CD-1 mice are pretreated with 150 mg/kg (Day −4) and 100 mg/kg (Day −1) of cyclophosphamide to render mice neutropenic. The lung infection is established through intranasal administration of 20-30 µL of inoculum to each nostril, administering a total inoculum of approximately $2 \times 10^7$ CFU of *K. pneumoniae* ATCC 43816. Infections are allowed to establish for two hours prior to treatment with (1) sodium bicarbonate (2) an antimicrobial agent or (3) both sodium bicarbonate and the antimicrobial agent. The sodium bicarbonate can be administered at 50-225 mM as a nebulized solution or suspension. The antimicrobial agent can be a polymyxin, azithromycin, or diminazene. The antimicrobial agent can be administered intraperitoneally. The antimicrobial agent can be azithromycin (0.25 mg/kg) administered intraperitoneally. For example, the mice can be exposed to nebulized bicarbonate solution or suspension (50-225 mM) for approximately 10 minutes at 2 hours and 12 hours post-infection. Azithromycin (0.25 mg/kg) can be administered intraperitoneally at 2 hours post-infection. Mice are euthanized after 36-48 hours and the bacterial load in the lungs measured.

Systemic infection: An antimicrobial agent in the absence or in the presence of sodium bicarbonate is tested against *K. pneumoniae* ATCC 43816 in an immunocompetent bacteremia infection model. Female CD-1 mice are infected intraperitoneally with approximately $2 \times 10^4$ CFU of *K. pneumoniae* ATCC 43816 with 5% porcine mucin (Sigma-Aldrich). Infections are allowed to establish for 1 hour prior to treatment with (1) sodium bicarbonate (2) the antimicrobial agent or (3) both sodium bicarbonate and the antimicrobial agent. All compounds are administered intraperitoneally. The sodium bicarbonate can be administered at 90 mM/kg. The antimicrobial agent can be a polymyxin, azithromycin, or diminazene. The antimicrobial agent can be azithromycin administered at 0.5-1 mg/kg. After 4 hours, Groups 1 and 3 are treated again with sodium bicarbonate (90 mM/kg). Experimental endpoint is defined as 8 hours post infection. The spleen is collected, homogenized, and plated on LB to enumerate the bacterial load.

Ophthalmic infection: An antimicrobial agent in the absence or in the presence of sodium bicarbonate is tested against *P. aeruginosa* or *S. aureus* in an animal model (e.g., rabbit, mouse or guinea pig model) of bacterial keratitis as described in Marquart, *J Biomed Biotechnol.* 2011; 2011: 680642. Infections are allowed to establish (as described in Marquart) prior to treatment with (1) sodium bicarbonate, (2) the antimicrobial agent or (3) both sodium bicarbonate and the antimicrobial agent. All compounds are administered topically to the animal's eye. The bacterial load in the eye is subsequently measured.

Example 24: The Effect of Bicarbonate on the Activity of Azithromycin and Other Topical Antibiotics The in vitro antibiotic susceptibilities of azithromycin in the absence or in the presence of bicarbonate against common ophthalmic drug-resistant pathogens were investigated. Specifically, the minimum concentrations required to inhibit the growth of 90% of clinical isolates ($MIC_{90}$) were determined against methicillin-resistant *Staphylococcus aureus* and *Pseudomonas aeruginosa*. About one hundred clinically sources strains of each pathogen were tested. Further, the antibiotic susceptibilities of 13 other topical antibiotics commonly used for treatment of ocular infection, particularly bacterial conjunctivitis, were determined and compared to those of azithromycin in the absence or presence of 25 mM, 50 mM or 100 mM bicarbonate. Similarly, a small number of *Streptococcus pneumonia* strains were investigated for bicarbonate enhancement. Finally, the concentration dependence of bicarbonate-enhancement was calculated for eight different macrolide antibiotics Materials and Methods Bacterial Isolates This study included one hundred (n=100) clinical isolates of methicillin-resistant *Staphylococcus aureus* (MRSA) and ninety-two (n=92) clinical isolates of *P. aeruginosa*. All samples were collected from patients at Hamilton Health Sciences hospitals (Hamilton, Ontario, Canada). Isolates, regardless of site of infection, were selected for study if they were resistant to three or more antibiotics. The isolates were cultured on plates and subsequently tested for antimicrobial susceptibility. Initial culture and antibiotic susceptibility testing were performed by Hamilton General Hospital General Microbiology Laboratory using a VITEK 2 Automated System and its Advanced Expert System (bioMerieux) and were compliant with Clinical & Laboratory Standards Institute (CLSI) antibiotic susceptibility testing formulations. Both quantitative minimum inhibitory concentration (MIC) and CLSI breakpoints were reported for each antibiotic. Additionally, a total of 7 conjunctival-sourced ocular isolates of *Streptococcus pneumoniae* collected by the International Health Management Associates (IHMA) from various locations in the United States were used in the study.

Susceptibility Tests

Antimicrobial sensitivity of the pathogenic strains was determined in compliance with the CLSI protocol. Mueller-Hinton agar plates were used to streak out bacterial species and the direct colony suspension method for inoculum preparation was used to make a suspension of the organism in saline to the density of a McFarland 0.5 turbidity standard. Cation-adjusted Mueller-Hinton broth (CA-MHB) manufactured according to ISO technical standard was used for susceptibility testing in standard 96-well microdilution plates. All antibiotics were purchased as powders from Sigma-Aldrich Canada Co. (Oakville, Canada) and dissolved in appropriate solvent to provide stock solutions as instructed by the manufacturer. Desired test antibiotic solutions were diluted in solvent at a highest test concentration resulting in 256 µg/mL. Where sodium bicarbonate was used, aqueous sterile-filtered sodium bicarbonate solution (7.5% stock) from Sigma-Aldrich Canada Co. (Oakville, Canada) was diluted to the desired concentration in CAMHB. Plates were incubated for 18 hours at 37° C. and read at 600 nm on a Tecan, infinite M1000 PRO plate reader. In accordance with CLSI, methods with appropriate medium supplements for fastidious streptococci (2.5% lysed horse blood, Innovative Research, Inc., Novi, Mich.) were used. MICs for S. pneumoniae were read visually by two independent observers with no discordant MIC readings. All MICs in the study were conducted in duplicate. Quality control of susceptibility testing was performed by testing S. aureus ATCC 29213 and P. aeruginosa ATCC 27853 with results within the CLSI expected ranges for all antimicrobials.

Checkerboards

Standard checkerboard broth microdilution assays were set-up in 96-well microtiter plates with serially diluted 8 (or 10) concentrations of each drug (or bicarbonate), using the conditions based on CLSI guidelines, as noted above. All checkerboards were conducted in duplicate.

Results

MIC Distributions for MRSA

Table 14 shows a summary of the MIC distribution for azithromycin in the absence or presence of various concentrations of bicarbonate against 100 isolates of MRSA collected from hospital patients. FIG. 36 shows a graph of $MIC_{90}$ measurements as a function of bicarbonate concentration. The corresponding frequency distributions of MICs for MRSA are presented in FIG. 31. Resistance to macrolides was high in this collection of isolates. Using the European Committee on Antimicrobial Susceptibility Testing EUCAST (Resistant>2 µg/mL) or the CLSI (Resistant≥8 µg/mL) resistance breakpoints, the rates of full resistance for the isolates were both 93%. MRSA isolates were very susceptible to azithromycin in the presence of bicarbonate, with $MIC_{50}$s and $MIC_{90}$s of 1 and 2 µg/ml, respectively (for 50 mM bicarbonate). Indeed, the strong impact of macrolide resistance in MRSA was largely overcome with the addition of bicarbonate, bringing the $MIC_{90}$ to a susceptible breakpoint. Specifically, the eradication rate increased from 7 to 90% when 50 mM bicarbonate was added.

TABLE 14

MIC distributions against MRSA for azithromycin in the absence or presence of bicarbonate (n = 100).

| | MIC (µg/mL) | | | |
|---|---|---|---|---|
| | Minimum MIC obtained | Maximum MIC obtained | $MIC_{50}$ | $MIC_{90}$ |
| Azithromycin in the absence of bicarbonate | 1 | >256 | 128 | >256 |
| Azithromycin + 25 mM bicarbonate | 0.0156 | >256 | 4 | 4 |
| Azithromycin + 50 mM bicarbonate | 0.00781 | >256 | 1 | 2 |
| Azithromycin + 100 mM bicarbonate | 0.00391 | 256 | 0.5 | 1 |

MIC Distributions for P. aeruginosa

Table 15 shows the MIC distribution for azithromycin in the absence or in the presence of various concentrations of bicarbonate against 92 isolates of P. aeruginosa collected from hospital patients. FIG. 37 shows a graph of $MIC_{90}$ measurements as a function of bicarbonate concentration. P. aeruginosa is considered intrinsically resistant to the entire macrolide class of antibiotics. This is usually ascribed to low permeability and constitutive expression of efflux systems. Resistance to azithromycin was high in this collection of isolates, with MICs well above the (Gram-positive) breakpoints. The corresponding frequency distributions of $MIC_{90}$ values for P. aeruginosa are depicted in FIG. 32. Similar to MRSA, addition of bicarbonate rendered P. aeruginosa highly susceptible to azithromycin.

TABLE 15

MIC distributions against P. aeruginosa for azithromycin in the absence or presence of bicarbonate (n = 92).

| | MIC (µg/mL) | | | |
|---|---|---|---|---|
| | Minimum MIC obtained | Maximum MIC obtained | $MIC_{50}$ | $MIC_{90}$ % |
| Azithromycin in the absence of bicarbonate | 0.5 | >256 | 64 | 256 |
| Azithromycin + 25 mM bicarbonate | 0.00781 | 16 | 2 | 4 |
| Azithromycin + 50 mM bicarbonate | 0.00391 | 8 | 1 | 2 |
| Azithromycin + 100 mM bicarbonate | 0.000977 | 2 | 0.125 | 1 |

Activity Against *Streptococcus pneumoniae*

S. pneumoniae is another common and often drug-resistant pathogen known to cause ocular infections. The ability of azithromycin in the absence or in the presence of bicarbonate to inhibit the growth of 7 strains of conjunctival isolates of S. pneumoniae was assessed. Two examples are shown in Table 16 below for a macrolide-susceptible (#117337 (S)) and macrolide-resistant (#1186282 (R)) strain of S. pneumoniae. The code number from the IHMA collection for the S. pneumoniae strains is provided in Table 16.

TABLE 16

MICs against *S. pneumoniae* for azithromycin in the absence or presence of bicarbonate.

| | MIC (µg/mL) | |
|---|---|---|
| | #1173373 (S) | #1186268 (R) |
| Azithromycin in the absence of bicarbonate | 0.25 | 32 |
| Azithromycin + 25 mM bicarbonate | 0.00391 | 1 |
| Azithromycin + 50 mM bicarbonate | 0.00195 | 0.25 |
| Azithromycin + 100 mM bicarbonate | 0.000244 | 0.0625 |

Comparative Study of Topical Antibiotics

The $MIC_{90}$ values of 14 commonly used topical ophthalmic antibiotics were assessed in the absence of bicarbonate. FIG. 33 shows a summary of the $MIC_{90}$ values against MRSA (n=100) and *P. aeruginosa* (n=92). MRSA and *P. aeruginosa* showed resistance to all topical ophthalmic antibiotics tested, including moxifloxacin. In contrast, a composition comprising azithromycin and 50 mM bicarbonate shows potent $MIC_{90}$ values against both problematic pathogens.

Dose-Dependence of the Interaction with Bicarbonate

To assess the dose-dependence of the interaction of azithromycin and bicarbonate, standard microbroth checkerboard techniques in MRSA and *P. aeruginosa* were used. For both pathogens, enhancement of the activity of azithromycin was further pronounced with increasing concentrations of sodium bicarbonate, as shown in FIG. 34A and FIG. 34B, respectively. This is consistent in various different isolates of the pathogens. Evident within these checkerboards is the inherent resistance of MRSA and *P. aeruginosa* to azithromycin in the absence of bicarbonate, where >64 µg/mL of azithromycin was required to inhibit growth to less than 10% growth.

Macrolide-Wide Potentiation by Bicarbonate

The ability of bicarbonate to potentiate the action of various macrolide antibiotics was assessed. Here, the model Gram-positive and Gram-negative organisms, *S. aureus* and *Escherichia coli*, respectively, were used. The effects are consistent in clinical pathogens, as further assessed in MRSA and *P. aeruginosa*. In all cases, macrolide activity was enhanced in the presence of bicarbonate, to varying degrees depending on particular macrolide. FIG. 35 shows a summary of the observed potentiation (fold shift in MIC value) of the macrolides in the presence of 25 mM sodium bicarbonate, the lowest tested concentration.

Effect of Bicarbonate on Cellular Accumulation of Azithromycin

A method to measure azithromycin accumulation into a macrolide-resistant strain of MRSA was adapted from a protocol described in Richter et al., *Nature* 545, pp. 299-304 (2017). Liquid chromatography with tandem mass spectroscopy (LC-MS/MS) was used to quantify accumulation of azithromycin in the absence or presence of 50 mM sodium bicarbonate. Azithromycin was used at 512 µg/mL (because the strain is macrolide-resistant). The azithromycin (in the absence or presence of bicarbonate) was in contact with the MRSA for 10 minutes. As shown in FIG. 38, the presence of 50 mM bicarbonate led to an approximately 2.5-fold increase in the accumulation of azithromycin into a macrolide-resistant strain of MRSA.

Effect of Bicarbonate on Bactericidal Activity of Azithromycin

Experiments to measure the effect of bicarbonate on bactericidal activity of azithromycin were completed according to a Clinical & Laboratory Standards Institute (CLSI) protocol. Briefly, the various treatments were added to logarithmic-phase culture of MRSA in CA-MHB at the concentrations indicated in FIG. 39 and incubated at 37° C. At time points indicated in FIG. 39, cell suspensions were 10-fold serially diluted using sterile PBS buffer and spread on plates of MHB agar. Bacterial colonies were counted after cultivation at 37° C. for 24 hours. Time kill curve analysis demonstrated enhanced bacterial killing in the presence of sodium bicarbonate. FIG. 39 shows a kill curve against MRSA over a period of 4 hours for the PBS control, bicarbonate at 50 mM, azithromycin at 256 µg/mL and the combination (50 mM bicarbonate and 256 µg/mL azithromycin). These data show that azithromycin in the presence of bicarbonate has superior bactericidal action toward MRSA than azithromycin in the absence of bicarbonate.

Example 25: Effect of Bicarbonate on Antimicrobial Activity of Azithromycin in Animal Model of Skin Infection The effect of bicarbonate on antimicrobial activity of azithromycin against *P. aeruginosa* was tested in a mouse model of skin infection. Balb/c mice (6-8 weeks old, female) were rendered neutropenic. Mice were treated with cyclophosphamide on day −4 (150 mg/kg) and day −1 (100 mg/kg). The following compositions were prepared: (1) Vehicle: 5 mg/mL MC, 1% DMSO; (2) Vehicle+Sodium Bicarbonate: 5 mg/mL MC, 1% DMSO, 40 mM sodium bicarbonate; (3) Azithromycin: 5 mg/mL MC, 200 ug/mL Azithromycin; and (4) Combination: 5 mg/mL MC, 200 ug/mL Azithromycin, 40 mM sodium bicarbonate. A 10 mg/mL methylcellulose (MC) solution was made from methylcellulose 4000 cp. 100 mL of sterile water was heated in a microwave for 30 seconds prior to adding to MC to improve solubility. The composition was shaken on a vortex for ~20 min to completely dissolve. The compositions for mouse treatments were prepared as follows: (1) Vehicle: 980 µL sterile water, 20 µL, DMSO, 1 mL MC (10 mg/mL); (2) Vehicle+Sodium Bicarbonate: 891 µL of sterile water, 20 uL DMSO, 894, of sodium bicarbonate stock solution, 1 mL MC (10 mg/mL); (3) Azithromycin: 980 µL, sterile water, 20 µL, Azithromycin (20 mg/mL), 1 mL MC (10 mg/mL); and (4) Combination: 891 µL sterile water, 204, Azithromycin (20 mg/mL), 89 µL, Sodium Bicarbonate Solution, 1 mL MC (10 mg/mL). Each composition was vortexed after preparation.

A single colony of *P. aeruginosa* CA1216 was picked from a streaked plate (<1 week old) to make an overnight culture (ON) of bacteria in Luria Broth (LB). 1 mL of ON was spun down and resuspended in phosphate buffered saline (PBS). The optical density (OD) was measured, and the culture was diluted to an OD of 1 with PBS. To make inoculum, OD 1 culture was diluted 1/20 into 1 mL of PBS. The inoculum was diluted and plated on LB to quantify colony-forming units (CFU).

The mice were weighed. Buprenorphine IP (0.025 mg/kg) was administered as an analgesic. To anaesthetize the mice, isoflurane (gaseous anesthetic) was administered. Each mouse was removed from the induction chamber and maintained at 2.5% isoflurane using a nose cone. The fur was stripped from the back of the neck using autoclave tape. An area of ~2 $cm^2$ was tape stripped by applying and removing the tape 25-30 times. Following this procedure, the skin appeared red and shiny; however, no bleeding was induced.

The infection was performed on an anesthetized mouse by placing a 10 µl droplet containing approximately $10^6$ CFU/ ml *P. aeruginosa* onto the stripped area and spreading over the wound. Mice were placed into a recovery cage and monitored until the righting reflex returned. Mice were singly housed and monitored after infection.

Treatment was administered 1, 4, 8, 12, 20, and 24 hours post-infection by applying 100 μL of (1) Vehicle; (2) Vehicle+Sodium Bicarbonate; (3) Azithromycin; or (4) Combination (compositions for mouse treatments described above) to the wounded area. Wounded area was completely covered by spreading with the side of the pipette tip.

Animals were sacrificed 25 hours post-infection by cervical dislocation. The wounded tissue was cut away and placed into sterile PBS for all mice. The tissue was placed into 2 mL round-bottom centrifuge tube cut thoroughly with sterile surgical scissors. 1 mL of PBS and a metal homogenizer bead were added to each tube. The tissue was homogenized for 13 minutes, serially diluted in PBS, and plated on LB. The plates were incubated overnight at 37° C. to enumerate CFU. Results are shown in FIG. 40. The presence of bicarbonate enhanced the antimicrobial activity of azithromycin.

Example 26: Ophthalmic Topical Azithromycin and Bicarbonate Formulation and Method for Application Azithromycin and sodium bicarbonate are formulated in the same composition for ophthalmic use as follows. A dosage form of 1% azithromycin (by wt.) is provided as 2.5 mL of a sterile topical ophthalmic solution. Sodium bicarbonate is present at a concentration of about 50 millimoles/L. The solution further contains benzalkonium chloride (0.003%) mannitol, citric acid, sodium citrate, poloxamer 407, polycarbophil, edetate disodium (EDTA), sodium chloride, water and sodium hydroxide to adjust pH to 6.3. Bacterial conjunctivitis is treated with the solution by instilling 1 drop in the affected eye(s) twice daily, eight to twelve hours apart for the first two days and then instilling 1 drop in the affected eye(s) once daily for the next five days.

Example 27: Dermatologic Topical Azithromycin and Bicarbonate Formulation and Method for Application Azithromycin and sodium bicarbonate are formulated in a cream ointment composition for dermatologic topical use as follows. The azithromycin is provided as a 2.15% w/w oil and water-based emulsion. The composition's inactive ingredients are benzyl alcohol, cetomacrogol 1000, cetyl alcohol, mineral oil, phenoxyethanol, purified water, stearyl alcohol, and xanthan gum. Sodium bicarbonate is present at a concentration of about 50 millimoles/L. Dermatologic conditions (for example, mild, superficial, and small diabetic foot infections) are treated with the composition by applying a small amount of the composition to the affected area 3 times daily for 10 days.

All publications, patents and patent applications are herein incorporated by reference in their entirety to the same extent as if each individual publication, patent or patent application was specifically and individually indicated to be incorporated by reference in its entirety.

The invention claimed is:

1. An antimicrobial composition comprising:
   an effective amount of (i) bicarbonate and (ii) an antimicrobial agent;
   wherein the antimicrobial agent is azithromycin or a pharmaceutically acceptable salt thereof; and
   wherein the bicarbonate is present in the composition in an amount of about 0.01 wt % to about 8.4 wt % of the composition.

2. The composition of claim 1, wherein the bicarbonate is present in the composition in an amount of about 1.75 wt % to about 8.4 wt % of the composition.

3. The composition of claim 1, wherein the antimicrobial agent is present in the composition
   (a) in an amount of about 0.01 mg to about 25.0 mg of antimicrobial agent/mL of the composition; or
   (b) in an amount of about 0.01 mg to about 25.0 mg antimicrobial agent/g of composition.

4. The composition of claim 1, further comprising a pharmaceutically acceptable carrier, diluent or excipient.

5. The composition of claim 1, wherein the bicarbonate is a component of a buffer.

6. The composition of claim 1, wherein the bicarbonate is sodium bicarbonate, ammonium bicarbonate, lithium bicarbonate, potassium bicarbonate, magnesium bicarbonate, calcium bicarbonate or zinc bicarbonate.

7. The composition of claim 1, wherein the composition is a topical composition.

8. The composition of claim 7, wherein the topical composition is a solution, gel, cream, lotion, suspension, aerosol, nebulized spray, ointment, drops or patch.

9. The composition of claim 1, wherein the composition has a pH of about 7.4.

10. The composition of claim 1, wherein the bicarbonate decreases the growth of a bacterium in response to the azithromycin.

11. A method for treating or preventing a microbial infection, comprising administering to a subject in need thereof an effective amount of the composition of claim 1.

12. The method of claim 11, wherein the bicarbonate is present in the composition in an amount of about 1.75 wt % to about 8.4 wt % of the composition.

13. The method of claim 11, wherein the antimicrobial agent is present in the composition:
   (a) in an amount of about 0.01 mg to about 25.0 mg of antimicrobial agent/mL of the composition; or
   (b) in an amount of about 0.01 mg to about 25.0 mg antimicrobial agent/g of composition.

14. The method of claim 11, wherein the bicarbonate is sodium bicarbonate, ammonium bicarbonate, lithium bicarbonate, potassium bicarbonate, magnesium bicarbonate, calcium bicarbonate or zinc bicarbonate.

15. The method of claim 11, wherein the composition is a topical composition.

16. The method of claim 15, wherein the topical composition is a solution, gel, cream, lotion, suspension, aerosol, nebulized spray, ointment, drops or patch.

17. The method of claim 11, wherein the composition has a pH of about 7.4.

* * * * *